(12) United States Patent
Ben-Haim et al.

(10) Patent No.: US 6,330,476 B1
(45) Date of Patent: Dec. 11, 2001

(54) ELECTRICAL MUSCLE CONTROLLER USING A NON-EXCITATORY ELECTRIC FIELD

(75) Inventors: Shlomo Ben-Haim; Nissim Darvish, both of Haifa; Maier Fenster, Petach Tikva; Mike Yuval, Haifa, all of (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/723,989

(22) Filed: Nov. 28, 2000

Related U.S. Application Data

(63) Continuation of application No. 09/101,723, filed as application No. PCT/IL97/00012 on Jan. 8, 1997, and a continuation of application No. 08/595,365, filed on Feb. 1, 1996, now Pat. No. 5,738,096.

(60) Provisional application No. 60/009,769, filed on Jan. 11, 1996, provisional application No. 60/011,117, filed on Feb. 5, 1996, and provisional application No. 60/026,392, filed on Sep. 16, 1996.

(30) Foreign Application Priority Data

Jan. 8, 1996 (IL) .......................................................... 116699
Sep. 17, 1996 (IL) .......................................................... 119261

(51) Int. Cl.[7] .................................................. A61N 1/362
(52) U.S. Cl. .................................................... 607/9; 607/14
(58) Field of Search .............................................. 607/9, 14

(56) References Cited

U.S. PATENT DOCUMENTS

| | | |
|---|---|---|
| 4,559,947 | 12/1985 | Renger et al. . |
| 4,971,058 | 11/1990 | Pless et al. . |
| 5,154,501 | 10/1992 | Svenson et al. . |
| 5,172,699 | 12/1992 | Svenson et al. . |
| 5,184,620 | 2/1993 | Cudahy et al. . |
| 5,281,219 | 1/1994 | Kallok . |
| 5,443,489 | 8/1995 | Ben-Haim . |
| 5,549,646 | 8/1996 | Katz et al. . |
| 5,749,906 | 5/1998 | Kieval et al. . |
| 5,800,464 | 9/1998 | Kieval . |
| 5,814,079 | 9/1998 | Kieval . |

*Primary Examiner*—Carl Layno
(74) *Attorney, Agent, or Firm*—William H. Dippert; Cowan, Liebowitz & Latman, P.C.

(57) ABSTRACT

A method of modifying the force of contraction of at least a portion of a heart chamber, including providing a subject having a heart, comprising at least a portion having an activation, and applying a non-excitatory electric field having a given duration, at a delay after the activation, to the portion, which causes the force of contraction to be increased by at least 5%.

32 Claims, 25 Drawing Sheets

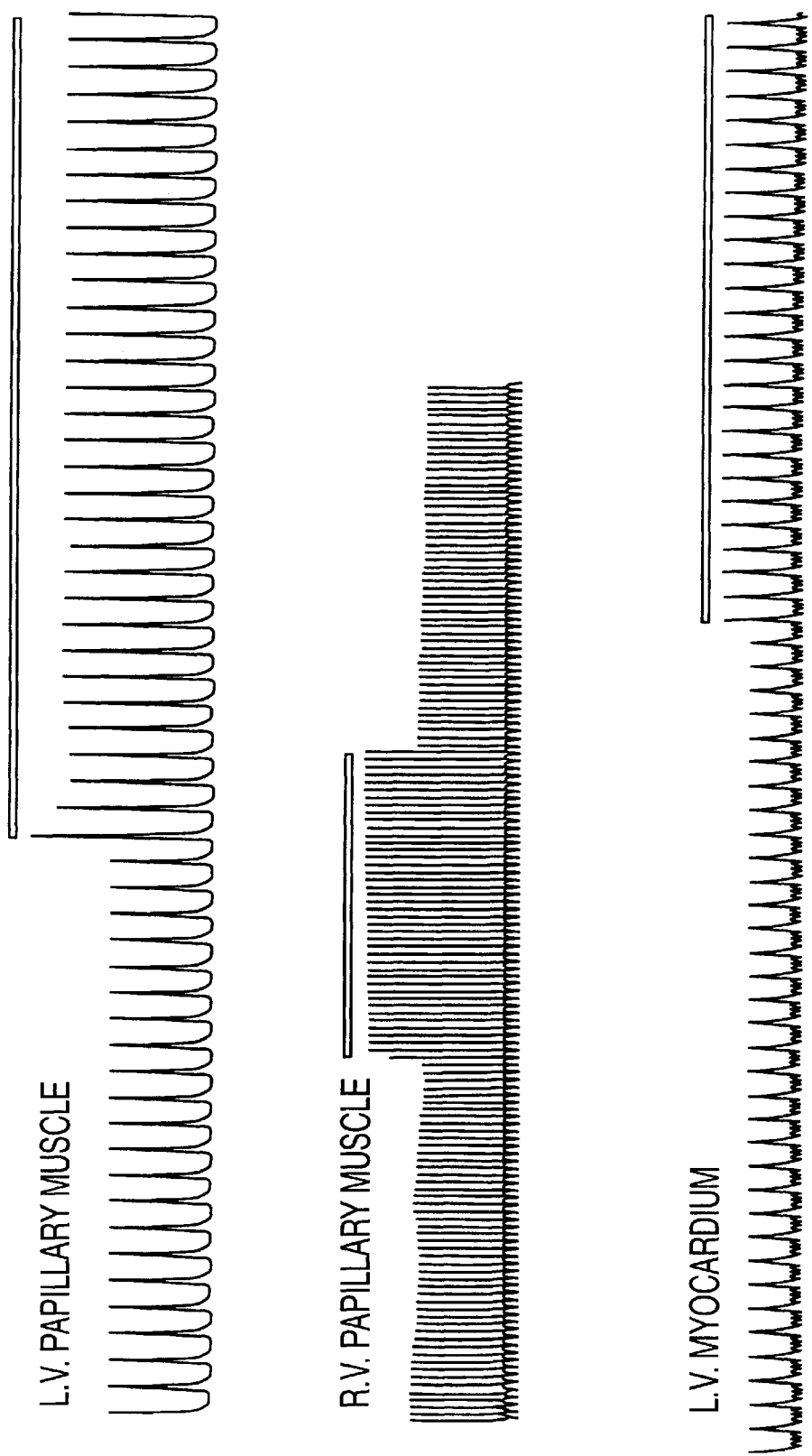

ELECTRICAL MUSCLE CONTROLLER USING A NON-EXCITATORY ELECTRIC FIELD

RELATED APPLICATIONS

This application is a continuation of commonly assigned, co-pending U.S. patent application Ser. No. 09/101,723, filed Aug. 13, 1998, incorporated herein by reference, which is a National Phase of PCT Patent Application No. PCT/IL97/00012, filed Jan. 8, 1997, which is related to the following U.S. and Israeli applications, the disclosures of which are also incorporated herein by reference: U.S. Provisional Application No. 60/009,769, filed on Jan. 11, 1996, Israel Application No 116,699, filed Jan. 8, 1996, U.S. Provisional Application No. 60/011,117, filed Feb. 5, 1996, Israeli Application No. 119,261, filed Sep. 17, 1996, U.S. Provisional Application No. 60/026,392 filed Sep. 16, 1996, and U.S. Application Ser. No. 08/595,365, filed Feb. 1, 1996, now U.S. Pat. No. 5,738,096.

FIELD OF THE INVENTION

The present invention relates to cardiac muscular control, in particular control using non-excitatory electrical signals.

BACKGROUND OF THE INVENTION

The heart is a muscular pump whose mechanical activation is controlled by electrical stimulation generated at a right atrium and passed to the entire heart. In a normal heart, the electrical stimulation that drives the heart originates as action potentials in a group of pacemaker cells lying in a sino-atrial (SA) node in the right atrium. These action potentials then spread rapidly to both right and left atria. When the action potential reaches an unactivated muscle cell, the cell depolarizes (thereby continuing the spread of the action potential) and contracts. The action potentials then enter the heart's conduction system and, after a short delay, spread through the left and right ventricles of the heart. It should be appreciated that activation signals are propagated within the heart by sequentially activating connected muscle fibers. Each cardiac muscle cell generates a new action potential for stimulating the next cell, after a short delay and in response to the activation signal which reaches it. Regular electrical currents can be conducted in the heart, using the electrolytic properties of the body fluids, however, due to the relatively large resistance of the heart muscle, this conduction cannot be used to transmit the activation signal.

In a muscle cell of a cardiac ventricle, the resting potential across its cellular membrane is approximately −90 mV (millivolts) (the inside is negatively charged with respect to the outside). FIG. 1A shows a transmembrane action potential of a ventricle cardiac muscle cell during the cardiac cycle. When an activation signal reaches one end of the cell, a depolarization wave rapidly advances along the cellular membrane until the entire membrane is depolarized, usually to approximately +20 mV (23). Complete depolarization of the cell membrane occurs in a very short time, about a few millisecond. The cell then rapidly (not as rapid as the depolarization) depolarizes by about 10 mV. After the rapid depolarization, the cell slowly repolarizes by about 20 mV over a period of approximately 200–300 msec (milliseconds), called the plateau (25). It is during the plateau that the muscle contraction occurs. At the end of the plateau, the cell rapidly repolarizes (27) back to its resting potential (21). Different cardiac muscle cells have different electrical characteristics, in particular, cells in an SA node do not have a substantial plateau and do not reach as low a resting potential as ventricular cells.

In the following discussion, it should be appreciated that the exact mechanisms which govern action potentials and ionic pumps and channels are only partly known. Many theories exist and the field in is a constant state of flux.

The electrical activity mirrors chemical activity in a cell. Before depolarization (at resting), the concentration of sodium ions inside the cell is about one tenth the concentration in the interstitial fluid outside the cell. Potassium ions are about thirty-five times more concentrated inside the cell than outside. Calcium ions are over ten thousand times more concentrated outside the cell than inside the cell. These concentration differentials are maintained by the selective permeability of the membrane to different ions and by ionic pumps in the membrane of the cell which continuously pump sodium and calcium ions out and potassium ions in. One result of the concentration differences between the cell and the external environment is a large negative potential inside the cell, about 90 mV as indicated above.

When a portion of the cell membrane is depolarized, such as by an action potential, the depolarization wave spreads along the membrane. This wave causes a plurality of voltage-gated sodium channels to open. An influx of sodium through these channels rapidly changes the potential of the membrane from negative to positive (23 in FIG. 1A). Once the voltage becomes less negative, these channels begin to close, and do not open until the cell is again depolarized. It should be noted that the sodium channels must be at a negative voltage of at least a particular value in order to be primed for reopening. Thus, these channels cannot be opened by an activation potential before the cell has sufficiently repolarized. In most cells, the sodium channels usually close more gradually than they open. After the rapid depolarization, the membrane starts a fast repolarization process. The mechanism for the fast repolarization is not fully understood, although closing of the sodium channels appears to be an important factor. Following a short phase of rapid repolarization, a relatively long period (200–300 msec) of slow repolarization term the plateau stage (25 in FIG. 1A) occurs. During the plateau it is not believed to be possible to initiate another action potential in the cell, because the sodium channels are inactivated.

Two mechanisms appear to be largely responsible for the long duration of the plateau, an inward current of calcium ions and an outward current of potassium ions. Both currents flow with their concentration gradients, across the membrane. The net result is that the two types of current electrically subtract from each other. In general, the flow of potassium and calcium is many times slower than the flow of the sodium, which is the reason why the plateau lasts so long. According to some theories, the potassium channels may also open as a result of the action potential, however, the probability of a potassium channel opening is dependent on the potential. Thus, many channels open only after the depolarization of the cell is under way or completed. Possibly, at least some of the potassium channels are activated by the calcium ions. In addition, some of the potassium channels are triggered by the repolarization of the membrane. The membrane permeability to potassium gradually increases, following its drop during the rapid depolarization (23). The calcium channels also conduct sodium back into the cell, which helps extend the plateau duration.

The inward calcium current during the normal cardiac action potential contributes to the action potential plateau and is also involved in the contractions (directly and/or indirectly) in the cardiac muscle cells. In a process termed calcium induced calcium release, the inward current of calcium induces the release of calcium ions stored in intracellular calcium stores (probably the sacroplasmic reticulum). The existence and importance of a physical link between the reticulum and the calcium channels in cardiac muscle in unclear. However, the response curve of these calcium stores may be bell-shaped, so that too great an influx of calcium may reduce the amount of available calcium relative to amount made available by a smaller influx.

In single cells and in groups of cells, time is required for cells to recover partial and full excitability during the repolarization process. While the cell is repolarizing (25, 27 in FIG. 1A), it enters a state of hyper polarization, during which the cell cannot be stimulated again to fire a new action potential. This state is called the refractory period. The refractory period is divided into two parts. During an absolute refractory period, the cell cannot be re-excited by an outside stimulus, regardless of the voltage level of the stimulus. During a relative refractory period, a much larger than usual stimulus signal is required to cause the cell to fire a new action potential. The refractory state is probably caused by the sodium channels requiring priming by a negative voltage, so the cell membrane cannot depolarize by flow of sodium ions until it is sufficiently repolarized. Once the cell returns to its resting potential (21), the cell may be depolarized again.

In an experimental methodology called voltage clamping, an electrical potential is maintained across at least a portion of a cell membrane to study the effects of voltage on ionic channels, ionic pumps and on the reactivity of the cell.

It is known that by applying a positive potential across the membrane, a cell may be made more sensitive to a depolarization signal. Some cells in the heart, such as the cells in the SA node (the natural pacemaker of the heart) have a resting potential of about −55 mV. As a result, their voltage-gated sodium channels are permanently inactivated and the depolarization stage (23) is slower than in ventricular cells (in general, the action potential of an SA node cell is different from that shown in FIG. 1A). However, cells in the SA node have a built-in leakage current, which causes a self-depolarization of the cell on a periodic basis. In general, it appears that when the potential of a cell stay below about −60 mV for a few msec, the voltage-gated sodium channels are blocked. Applying a negative potential across its membrane make a cell less sensitive to depolarization and also hyperpolarizes the cell membrane, which seems to reduce conduction velocity.

In modern cardiology many parameters of the heart's activation can be controlled. Pharmaceuticals can be used to control the conduction velocity, excitability, contractility and duration of the refractory periods in the heart. These pharmaceuticals may be used to treat arrhythmias and prevent fibrillations. A special kind of control can be achieved using a pacemaker. A pacemaker is an electronic device which is typically implanted to replace the heart's electrical excitation system or to bypass a blocked portion of the conduction system. In some types of pacemaker implantation, portions of the heart's conduction system, for example an atrial-ventricle (AV) node, must be ablated in order for the pacemaker to operate correctly.

Another type of cardiac electronic device is a defibrillator. As an end result of many diseases, the heart may become more susceptible to fibrillation, in which the activation of the heart is substantially random. A defibrillator senses this randomness and resets the heart by applying a high voltage impulse(s) to the heart.

Pharmaceuticals are generally limited in effectiveness in that they affect both healthy and diseased segments of the heart, usually, with a relatively low precision. Electronic pacemakers, are further limited in that they are invasive, generally require destruction of heart tissue and are not usually optimal in their effects. Defibrillators have substantially only one limitation. The act of defibrillation is very painful to the patient and traumatic to the heart.

"Electrical Stimulation of Cardiac Myoctes," by Ravi Ranjan and Nitish V. Thakor, in *Annals of Biomedical Engineering*, Vol. 23, pp. 812–821, published by the Biomedical Engineering Society, 1995, the disclosure of which is incorporated herein by reference, describes several experiments in applying electric fields to cardiac muscle cells. These experiments were performed to test theories relating to electrical defibrillation, where each cell is exposed to different strengths and different relative orientations of electric fields. One result of these experiments was the discovery that if a defibrillation shock is applied during repolarization, the repolarization time is extended. In addition, it was reported that cells have a preferred polarization. Cardiac muscle cells tend to be more irregular at one end than at the other. It is theorized, in the article, that local "hot spots" of high electrical fields are generated at these irregularities and that these "hot spots" are the sites of initial depolarization within the cell, since it is at these sites that the threshold for depolarization is first reached. This theory also explains another result, namely that cells are more sensitive to electric fields in their longitudinal direction than in their transverse direction, since the irregularities are concentrated at the cell ends. In addition, the asymmetric irregularity of the cells may explain results which showed a preferred polarity of the applied electric field.

The electrical activation of skeleton muscle cells is similar to that of cardiac cells in that a depolarization event induces contraction of muscle fibers. However, skeleton muscle is divided into isolated muscle bundles, each of which is individually enervated by action potential generating nerve cells. Thus, the effect of an action potential is local, while in a cardiac muscle, where all the muscle cells are electrically connected, an action potential is transmitted to the entire heart from a single loci of action potential generation. In addition, the chemical aspects of activation of skeletal muscle is somewhat different from those of cardiac muscle.

"Muscle Recruitment with Infrafascicular Electrodes", by Nicola Nannini and Kenneth Horch, *IEEE Transactions on Biomedical Engineering*, Vol. 38, No. 8, pp. 769–776, August 1991, the disclosure of which is incorporated herein by reference, describes a method of varying the contractile force of skeletal muscles, by "recruiting" a varying number of muscle fibers. In recruiting, the contractile force of a muscle is determined by the number of muscle fibers which are activated by a stimulus.

However, it is generally accepted that cardiac muscle fibers function as a syncytium such that each and every cell contracts at each beat. Thus, there are no cardiac muscles fibers available for recruitment. See for example, "Excitation Contraction Coupling and Cardiac Contractile Force", by Donald M. Bers, Chapter 2, page 17, Kluwer Academic, 1991, the disclosure of which is incorporated herein by reference. This citation also states that in cardiac muscle cells, contractile force is varied in large part by changes in peak calcium.

"Effect of Field Stimulation on Cellular Repolarization in Rabbit Myocardium", by Stephen B. Knisley, William M. Smith and Raymond E. Ideker, *Circulation Research*, Vol. 70, No. 4, pp. 707–715, April 1992, the disclosure of which is incorporated herein by reference, describes the effect of an electrical field on rabbit myocardium. In particular, this article describes prolongation of an action potential as a result of a defibrillation shock and ways by which this effect can cause defibrillation to fail. One hypothesis is that defibrillation affects cardiac cells by exciting certain cells which are relatively less refractory than others and causes the excited cells to generate a new action potential, effectively increasing the depolarization time.

"Optical Recording in the Rabbit Heart Show That Defibrillation Strength Shocks Prolong the Duration of Depolarization and the Refractory Period", by Stephen M. Dillon, *Circulation Research*, Vol. 69, No. 3, pp. 842–856, September, 1991, the disclosure of which is incorporated herein by reference, explains the effect of prolonged repolarization as caused by the generation of a new action potential in what was thought to be refractory tissue as a result of the defibrillation shock. This article also proves experimentally that such an electric shock does not damage the cardiac muscle tissue and that the effect of a second action potential is not due to recruitment of previously unactivated muscle fibers. It is hypothesized in this article that the shocks hyperpolarize portions of the cellular membrane and thus reactivate the sodium channels. In the experiments described in this article, the activity of calcium channels is blocked by the application of methoxy-verapamil.

"Electrical Resistances of Interstitial and Microvascular Space as Determinants of the Extracellular Electrical field and Velocity of Propagation in Ventricular Myocardium", by Johannes Fleischhauer, Lilly Lehmann and Andre G. Kleber, *Circulation*, Vol. 92, No. 3, pp. 587–594, Aug. 1, 1995, the disclosure of which is incorporated herein by reference, describes electrical conduction characteristics of cardiac muscle.

"Inhomogeneity of Cellular Activation Time and Vmax in Normal Myocardial Tissue Under Electrical Field Stimulation", by Akihiko Taniguchi, Junji Toyama, Itsuo Kodama, Takafumi Anno, Masaki Shirakawa and Shiro Usui, *American Journal of Physiology*, Vol. 267 (Heart Circulation Physiology, Vol. 36), pp. H694–H705, 1994, the disclosure of which is incorporated herein by reference, describes various interactions between electro-tonic currents and action potential upstrokes.

"Effect of Light on Calcium Transport in Bull Sperm Cells", by R. Lubart, H. Friedmann, T. Levinshal, R. Lavie and H. Breitbart, *Journal of Photochemical Photobiology B*, Vol. 14, No. 4, pp. 337–341, Sep. 12, 1992, the disclosure of which is incorporated herein by reference, describes an effect of light on bull sperm cells, in which laser light increases the calcium transport in these cells. It is also known that low level laser light affects calcium transport in other types of cells, for example as described in U.S. Pat. No. 5,464,436, the disclosure of which is incorporated herein by reference.

The ability of electro-magnetic radiation to affect calcium transport in cardiac myocytes is well documented. Loginov V A, "Accumulation of Calcium Ions in Myocardial Sarcoplasmic Reticulum of Restrained Rats Exposed to the Pulsed Electromagnetic Field", in *Aviakosm Ekolog Med*, Vol. 26, No. 2, pp. 49–51, March–April, 1992, the disclosure of which is incorporated herein by reference, describes an experiment in which rats were exposed to a 1 Hz field of between 6 and 24 mTesla. After one month, a reduction of 33 percent in the velocity of calcium accumulation was observed. After a second month, the accumulation velocity was back to normal, probably due to an adaptation mechanism.

Schwartz J L, House D E and Mealing G A, in "Exposure of Frog Hearts to CW or Amplitude-Modulated VHF Fields: Selective Efflux of Calcium Ions at 16 Hz", *Bioelectromagnetics*, Vol. 11, No. 4, pp. 349–358, 1990, the disclosure of which is incorporated herein by reference, describes an experiment in which the efflux of calcium ions in isolated frog hearts was increased by between 18 and 21% by the application of a 16 Hz modulated VHF electromagnetic field.

Lindstrom E, Lindstrom P, Berglund A, Lundgren E and Mild K H, in "Intracellular Calcium Oscillations in a T-cell Line After Exposure to Extremely-Low-Frequency Magnetic Fields with Variable Frequencies and Flux Densities", *Bioelectromagnetics*, Vol. 16, No. 1, pp. 41–47, 1995, the disclosure of which is incorporated herein by reference, describes an experiment in which magnetic fields, at frequency between 5 and 100 Hz (Peak at 50 Hz) and with intensities of between 0.04 and 0.15 mTesla affected calcium ion transport in T-cells.

Loginov V A, Gorbatenkova N V and Klimovitskii Vla, in "Effects of an Impulse Electromagnetic Field on Calcium Ion Accumulation in the Sarcoplasmatic Reticulum of the Rat Myocardium", *Kosm Biol Aviakosm Med*, Vol. 25, No. 5, pp. 51–53, September–October, 1991, the disclosure of which is incorporated herein by reference, describes an experiment in which a 100 minute exposure to a 1 msec impulse, 10 Hz frequency and 1–10 mTesla field produced a 70% inhibition of calcium transfer across the sarcoplasmic reticulum. The effect is hypothesized to be associated with direct inhibition of Ca-ATPase.

It should be noted that some researchers claim that low frequency magnetic fields do NOT have the above reported effects. For example, Coulton L A and Barker A T, in "Magnetic Fields and Intracellular Calcium: Effects on Lymphocytes Exposed to Conditions for 'Cyclotron Resonance'", *Phys Med Biol*, Vol. 38, No. 3, pp. 347–360, March, 1993, the disclosure of which is incorporated herein by references, exposed lymphocytes to radiation at 16 and 50 Hz, for a duration of 60 minutes and failed to detect any changes in calcium concentration.

Pumir A, Plaza F and Krinsky V I, in "Control of Rotating Waves in Cardiac Muscle: Analysis of the Effect of Electric Fields", *Proc R Soc Lond B Biol Sci*, Vol. 257, No. 1349, pp. 129–34, Aug. 22, 1994, the disclosure of which is incorporated herein by reference, describes that an application of an external electric field to cardiac muscle affects conduction velocity by a few percent. This effect is due to the hyperpolarization of one end of muscle cells and a depolarization of the other end of the cell. In particular, an externally applied electric field favors propagation antiparallel to it. It is suggested in the article to use this effect on conduction velocity to treat arrhythmias by urging rotating waves, which are the precursors to arrhythmias, to drift sideways to non-excitable tissue and die.

"Control of Muscle Contractile Force Through Indirect High-Frequency Stimulation", by M. Sblomonow, E. Eldred, J. Lyman and J. Foster, *American Journal of Physical Medicine*, Vol. 62, No. 2, pp. 71–82, April 1983, the disclosure of which is incorporated herein by reference, describes a method of controlling skeletal muscle contraction by varying various parameters of a 500 Hz pulse of electrical stimulation to the muscle.

"Biomedical Engineering Handbook", ed. Joseph D. Bronzino, chapter 82.4, page 1288, IEEE press/CRC press, 1995, describes the use of precisely timed subthreshold stimuli, simultaneous stimulation at multiple sites and pacing with elevated energies at the site of a tachycardia foci, to prevent tachycardia. However, none of these methods had proven practical at the time the book was written. In addition a biphasic defibrillation scheme is described and it is theorized that biphasic defibrillation schemes are more effective by virtue of a larger voltage change when the phase changes or by the biphasic waveform causing hyperpolarization of tissue and reactivation of sodium channels.

"Subthreshold Conditioning Stimuli Prolong Human Ventricular Refractoriness", Windle J R, Miles W M, Zipes D P and Prystowsky E N, *American Journal of Cardiology*, Vol. 57, No. 6, pp. 381–386, February, 1986, the disclosure of which is incorporated herein by reference, describes a study in which subthreshold stimuli were applied before a premature stimulus and effectively blocked the premature stimulus from having a pro-arrhythmic effect by a mechanism of increasing the refractory period of right ventricular heart tissue.

"Ultrarapid Subthreshold Stimulation for Termination of Atrioventricular Node Reentrant Tachycardia", Fromer M and Shenasa M, *Journal of the American Collage of Cardiology*, Vol. 20, No. 4, pp. 879–883, October, 1992, the disclosure of which is incorporated herein by reference, describes a study in which trains of subthreshold stimuli were applied asynchronously to an area near a reentry circuit and thereby terminated the arrhythmia. Subthreshold stimuli were described as having both an inhibitory and a facilitating effect on conduction. In addition, subthreshold stimuli are described as reducing the threshold of excitability, possibly even causing an action potential.

"Inhibition of Premature Ventricular Extrastimuli by Subthreshold Conditioning Stimuli", Skale B, Kallok M J, Prystowsky E N, Gill R M and Zipes D P, *Journal of the American Collage of Cardiology*, Vol. 6, No. 1, pp. 133–140, July, 1985, the disclosure of which is incorporated herein by reference, describes an animal study in which a train of 1 msec duration pulses were applied to a ventricle 2 msec before a premature stimuli, inhibited the response to the premature stimuli, with a high frequency train delaying the response for a much longer amount of time (152 msec) than a single pulse (20 msec). The delay between the pacing of the ventricle and the pulse train was 75 msec. However, the subthreshold stimuli only had this effect when delivered to the same site as the premature stimulus. It is suggested to use a subthreshold stimuli in to prevent or terminate tachycardias, however, it is noted that this suggestion is restrained by the spatial limitation of the technique.

"The Phase of Supernormal Excitation in Relation to the Strength of Subthreshold Stimuli", Yokoyama M, Japanese Heart Journal, Vol. 17, No. 3, pp. 35–325, May, 1976, the disclosure of which is incorporated herein by reference, describes the effect of varying the amplitude of a subthreshold stimuli on supernormal excitation. When the amplitude of the stimuli was increased, the supernormal excitation phase increased in length.

SUMMARY OF THE INVENTION

It is an object of some aspects of the present invention to provide a method of locally controlling the electrical and/or mechanical activity of cardiac muscle cells, in situ. Preferably, continuous control is applied. Alternatively, discrete control is applied. Further preferably, the control may be varied between cardiac cycles. One example of electrical control is shortening the refractory period of a muscle fiber by applying a negative voltage to the outside of the cell. The cell may also be totally blocked from reacting by maintaining a sufficiently positive voltage to the outside of the cell, so that an activation signal fails to sufficiently depolarize the cellular membrane. One example of mechanical control includes increasing or decreasing the strength of contraction and the duration of the contraction. This may be achieved by extending or shortening the plateau and/or the action potential duration by applying non-excitatory voltage potentials across the cell. The increase in strength of contraction may include an increase in peak force of contraction attained by muscle fibers, may be an increase in an average force of contraction, by synchronization of contraction of individual fibers or may include changing the timing of the peak strength.

It should be appreciated that some aspects of the present invention are different from both pacemaker operation and defibrillator operation. A pacemaker exerts excitatory electric fields for many cycles, while a defibrillator does not repeat its applied electric field for many cycles, due to the disruptive effect of the defibrillation current on cardiac contraction. In fact, the main effect of the defibrillation current is to reset the synchronization of the heart by forcing a significant percentage of the cardiac tissue into a refractory state. Also, defibrillation currents are several orders of magnitude stronger than pacing currents. It is a particular aspect of some embodiments of the present invention that the regular activation of the heart is not disrupted, rather, the activation of the heart is controlled, over a substantial number of cycles, by varying parameters of the reactivity of segments of cardiac muscle cells.

In some aspects of the invention, where the heart is artificially paced in addition to being controlled in accordance with the present invention, the activation cycle of the heart is normal with respect to the pacing. For example, when the control is applied locally, such that the activation of the rest of the heart is not affected.

In some aspect of the invention, the control is initiated as a response to an unusual cardiac event, such as the onset of fibrillation or the onset of various types of arrhythmias. However, in other aspects of the present invention, the control is initiated in response to a desired increase in cardiac output or other long-term effects, such as reducing the probability of ventricular fibrillation (VF) or increasing the coronary blood flow.

Another difference between defibrillation, pacing and some embodiments of the present invention is that defibrillation and pacing are applied as techniques to affect the entire heart (or at least an entire chamber), while certain embodiments of the present invention, for example, fences (described below), are applied to local portion of the heart (which may be as large as an entire chamber) with the aim of affecting only local activity. Yet another difference between some embodiment of the present invention and defibrillation is in the energy applied to the heart muscle. In defibrillation, a typical electric field strength is 0.5 Joule (which is believed to be strong enough to excite refractory tissue, "Optical Recordings . . . ", cited above), while in various embodiment of the invention, the applied field strength is between 50 and 500 micro joules, a field strength which is believed to not cause action potentials in refractory tissue.

It is a further object of some aspects of the present invention to provide a complete control system for the heart which includes, inter alia, controlling the pacing rate, refractory period, conduction velocity and mechanical force of the heart. Except for heart rate, each of these parameters may be locally controlled, i.e., each parameter will be controlled in only a segment of cardiac muscle. It should be noted that heart rate may also be locally controlled, especially with the use of fences which isolate various heart segments from one another, however, in most cases this is detrimental to the heart's pumping efficiency.

In one preferred embodiment of the present invention, electrical and/or mechanical activity of a segment of cardiac muscle is controlled by applying a non-exciting field (voltage) or current across the segment. A non-exciting signal may cause an existing action potential to change, but it will not cause a propagating action potential, such as those induced by pacemakers. The changes in the action potential may include extension of the plateau duration, extension of the refractory period, shortening of the post-plateau repolariation and other changes in the morphology of the action potential. However, the non-exciting signal may affect a later action potential, for example, it may delay such a potential or may accelerate its onset. Another type of non-exciting signal is a voltage which does not cause a new contraction of the cardiac muscle cell to which the non-exciting signal is applied. Activation potential generation may be averted either by applying voltage of the wrong polarity; the voltage being applied when the cell and/or the surrounding cells are not sensitive to it or by the amplitude of the voltage being too small to depolarize the cell to the extent that a new action potential will be generated during that period.

Optionally, this control is exerted in combination with a pacemaker which applies an exciting signal to the heart. In a preferred embodiment of the invention, a pacemaker (or a defibrillator) incorporates a controller, operating in accordance with at least one embodiment of the invention. A pacemaker and a controller may share a battery, a microcontroller, sensors and possibly electrodes.

In another preferred embodiment of the present invention, arrhythmias and fibrillation are treated using fences. Fences are segments of cardiac muscle which are temporarily inactivated using electrical fields. In one example, atrial fibrillation is treated by channeling the activation signal from an SA node to an AV node by fencing it in. In another example, fibrillations are damped by fencing in the multitude of incorrect activation signals, so that only one path of activation is conducting. In still another example, ventricular tachycardia or fibrillation is treated by dividing the heart into insulated segments, using electrical fields and deactivating the fences in sequence with a normal activation sequence of the heart, so that at most only one segment of the heart will be prematurely activated.

In still another preferred embodiment of the invention, the muscle mass of the heart is redistributed using electrical fields. In general, changing the workload on a segment of cardiac muscle activates adaptation mechanisms which tend to change the muscle mass of the segment with time. Changing the workload may be achieved, in accordance with a preferred embodiment of the invention, by increasing or decreasing the action potential plateau duration of the segment, using applied electrical fields. Alternatively or additionally, the workload may be changed indirectly, in accordance with a preferred embodiment of the invention, by changing the activation time of the segment of the heart and/or its activation sequence. Further additionally or alternatively, the workload may be changed by directly controlling the contractility of a segment of the heart.

In yet another preferred embodiment of the invention, the operation of the cardiac pump is optimized by changing the activation sequence of the heart and/or by changing plateau duration at segments of the heart and/or by changing the contractility thereat.

In still another preferred embodiment of the invention, the cardiac output is modified, preferably increased, by applying a non-excitatory electric field to a segment of the heart, preferably the left ventricle. Preferably, the extent of increase in cardiac output, especially the left ventricular output, is controlled by varying the size of the segment of the heart to which such a field is applied. Alternatively or additionally, the strength of the electric field is changed. Alternatively or additionally, the timing of the pulse is changed. Alternatively or additionally, the duration, shape or frequency of the pulse is changed. The increase in output may include an increase in peak flow rate, in flow volume, in average flow rate, or it may include a change in the flow profile, such as a shift in the development of the peak flow, which improves overall availability of blood to body organs.

In still another preferred embodiment of the invention, the developed ventricular pressure is modified, preferably increased, by applying a non-excitatory electric field to a segment of the heart, preferably the left ventricle. Preferably, the extent of increase in cardiac output is controlled by varying the size of the segment of the heart to which such a field is applied. Alternatively or additionally, the strength of the electric field is changed. Alternatively or additionally, the timing of the pulse is changed. Alternatively or additionally, the duration of the pulse is changed. Alternatively or additionally, the waveform of the pulse is changed. Alternatively or additionally, the frequency of the pulse is changed. The increase in pressure may include an increase in peak pressure, average pressure or it may include a change in the pressure profile, such as a shift in the development of the peak pressure, which improves the contractility.

In accordance with yet another preferred embodiment of the invention, the afterload of the heart is increased by applying non-excitatory electric fields to at least a segment of the heart, whereby the flow in the coronary arteries is improved.

In accordance with another preferred embodiment of the invention various cardiac parameters are controlled via inherent cardiac feedback mechanisms. In one example, the heart rate is controlled by applying a non-exciting voltage to pacemaker cells of the heart, at or near the SA node of the heart. Preferably, the heart rate is increased by applying the non-excitatory field.

In a preferred embodiment of the invention, a single field is applied to a large segment of the heart. Preferably, the field is applied at a time delay after the beginning of the systole. Preferably, the non-exciting field is stopped before half of the systole is over, to reduce the chances of fibrillation.

In another preferred embodiment of the invention, a plurality of segments of the heart are controlled, each with a different non-excitatory electric field. Preferably, each electric field is synchronized to the local activation or other local parameters, such as initiation of contraction. A further preferred embodiment of the invention takes into account the structure of the heart. The heart muscle is usually disposed in layers, with each layer having a (different) muscle fiber orientation. In this embodiment of the invention, a different field orientation and/or polarity is preferably applied for different orientations of muscle fibers.

In one preferred embodiment of the invention, this technique, which takes the muscle fiber orientation into account, may be applied to local defibrillation-causing electric fields, the purpose of which fields may be to delay the repolarization of a certain, limited segment of the heart, thereby creating a fence.

There is therefore provided in accordance with a preferred embodiment of the invention, a method of modifying the force of contraction of at least a portion of a heart chamber, comprising:

providing a subject having a heart, comprising at least a portion having an activation; and applying a non-excitatory electric field having a given duration, at a delay after the activation, to the portion, which causes the force of contraction to be increased by at least 5%.

Preferably, the force is increased by a greater percentage such as at least 10%, 30% or 50%

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, to the portion at a delay of less than 70 msec after the activation.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field having a given duration, at a delay after the activation, to the portion, which causes the pressure in the chamber to be increased by at least 2%.

Preferably the pressure is increased by a greater amount such as at least 10% or 20%.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field having a given duration, at a delay after the activation, to the portion, wherein the chamber has a flow volume and wherein the flow volume is increased by at least 5%.

Preferably, the flow volume is increased by a greater amount such as at least 10% or 20%.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field having a given duration, at a delay after the activation, to the portion, wherein the chamber has a flow rate such that the flow rate is increased by at least 5%.

Preferably, the flow rate is increased by a greater amount such as at least 10% or 20%.

There is further provided, in accordance with a preferred embodiment of the invention a method of modifying the force of contraction of at least a portion of a heart chamber, comprising:

providing a subject having a heart, comprising at least a portion having an activation; and applying a non-excitatory electric field to the portion at a delay after the activation, the field having a given duration of at least 101 msec and not lasting longer than the cycle length. Preferably the duration is longer, such as at least 120 msec or 150 msec.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the portion of the chamber has an inner surface and an outer surface and wherein the field is applied between the inner surface and the outer surface.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the portion of the chamber has an inner surface and an outer surface and wherein the field is applied along the outer surface.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the portion of the chamber has an inside surface, an outside surface and an intra-muscle portion and wherein the field is applied between the intra-muscle portion and at least one of the surfaces.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied between a single electrode and a casing of an implanted device.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, using an electrode floating inside the heart.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least two electrodes and wherein the at least two electrodes are at least 2 cm apart.

In preferred embodiments of the invention the electrodes are at least 4 or 9 cm apart.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least two electrodes and wherein one electrode of the at least two electrodes is at a base of a chamber of the heart and one electrode is at an apex of a chamber of the heart.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least three electrodes and wherein applying a non-excitatory field comprises:

electrifying a first pair of the at least three electrodes; and subsequently electrifying a second pair of the at least three electrodes.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the field is applied using at least two electrodes placed externally to the subject.

There is further provided, in accordance with a preferred embodiment of the invention a method of modifying a force of contraction of at least a portion of a heart chamber, comprising:

providing a subject having a heart, comprising at least a portion having an activation; and applying a non-excitatory electric field having a given duration, at a delay after the activation, to the portion, wherein the electric field at least partially cancels electrotonic currents in at least the portion of the heart chamber.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion between two positions; and sensing an activation at a site between the two positions.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion between two positions; and sensing an activation at a site coinciding with one of the two positions.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion between two positions;

sensing an activation at a site; and estimating the activation of the portion from the sensed activation.

Preferably sensing comprises sensing a value of a parameter of an ECG and wherein estimating comprises estimating the delay based on a delay value associated with the value of the parameter.

Preferably, the site is at a different chamber of the heart than the chamber at which the field is applied.

Preferably, the site is substantially the earliest activated site in the chamber of the portion.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion; and applying a second non-excitatory electric field to a second portion of the chamber.

There is further provided, in accordance with a preferred embodiment of the invention a method according to claim 36, wherein the second field is applied in the same cardiac cycle as the non-excitatory field.

Preferably, each portion has an individual activation to which the applications of the field thereat are synchronized.

Preferably, the second field has a different effect on the heart than the non-excitatory field.

Preferably, only the second non-excitatory field is applied during a different cardiac cycle.

There is further provided, in accordance with a preferred embodiment of the invention a method of modifying a force of contraction of at least a portion of a heart chamber, comprising:

providing a subject having a heart, comprising at least a portion having an activation;

estimating the activation at the portion; and applying a non-excitatory electric field having a given duration, at a delay after the estimated activation, to the portion.

There is further provided, in accordance with a preferred embodiment of the invention a method of modifying a force of contraction of at least a portion of a heart chamber, comprising:

providing a subject having a heart, comprising at least a portion having an activation;

applying a non-excitatory electric field having a given duration, at a delay after the activation, to the portion; and repeating application of the non-excitatory field, during a plurality of later heart beats, at least some of which are not consecutive.

Preferably, the method comprises gradually reducing the frequency at which beats are skipped during the repeated application.

There is further provided, in accordance with a preferred embodiment of the invention a method of modifying a force of contraction of at least a portion of a heart chamber, comprising:

provided a subject having a heart, comprising at least a portion having an activation;

applying a non-excitatory electric field having a given duration, at a delay after the activation, to the portion, wherein the portion has an extent; and changing the extent of the portion to which the field is applied, between beats.

There is further provided, in accordance with a preferred embodiment of the invention a method of modifying a force of contraction of at least a portion of a heart chamber, comprising:

providing a subject having a heart, comprising at least a portion having an activation;

irradiating the portion with light synched to the activation; and repeating irradiating at at least 100 cardiac cycles, during a period of less than 1000 cardiac cycles.

There is further provided, in accordance with a preferred embodiment of the invention a method of modifying a force of contraction of at least a portion of a heart chamber, comprising:

providing a subject having a heart, comprising at least a portion having an activation;

irradiating the portion with radio frequency radiation synched to the activation; and repeating irradiating at at least 100 cardiac cycles, during a period of less than 1000 cardiac cycles.

There is further provided, in accordance with a preferred embodiment of the invention a method of modifying a force of contraction of at least a portion of a heart chamber, comprising:

providing a subject having a heart, comprising at least a portion having an activation; and modifying the availability of calcium ions inside muscle fibers of the portion, during a period of time including a time less than 70 msec after the activation, in response to the activation.

There is further provided, in accordance with a preferred embodiment of the invention a method of modifying a force of contraction of at least a portion of a heart chamber, comprising:

providing a subject having a heart, comprising at least a portion having an activation; and modifying the transport rate of calcium ions inside muscle fibers of the portion, during a period of time less than 70 msec after the activation, in response to the activation.

There is further provided, in accordance with a preferred embodiment of the invention a method of modifying a force of contraction of at least a portion of a heart chamber, comprising:

providing a subject having a heart, comprising at least a portion having an activation; and modifying the availability of catecholamines at the portion in synchrony with the activation.

There is further provided, in accordance with a preferred embodiment of the invention a method of modifying the activation profile of at least a portion of a heart, comprising, mapping the activation profile of the portion;

determining a desired change in the activation profile; and modifying, using a non-excitatory electric field, the conduction velocity in a non-arrhythmic segment of the portion, to achieve the desired change.

In a preferred embodiment of the invention, wherein the desired change is an AV interval and wherein modifying comprises modifying the conduction velocities of purkinje fibers between an AV node and at least one of the ventricles in the heart.

In a preferred embodiment of the invention, the activation comprises an average activation of the portion.

In a preferred embodiment of the invention, the activation comprises an earliest activation.

In a preferred embodiment of the invention, the activation comprises a mechanical activation.

In a preferred embodiment of the invention, wherein the activation comprises an electrical activation.

In a preferred embodiment of the invention, wherein the portion comprises a plurality of subportions, each having an individual activation and wherein applying a field comprises applying a field to each subportion at a delay relative to the individual activation of the subportion.

In a preferred embodiment of the invention, applying a non-excitatory electric field comprises driving an electric current through the segment. Preferably, the current is less than 20 mA. In some embodiments of the invention the current is less than 8 mA, 5 mA, 3 mA. Preferably, the current is at least 0.5 mA. In some embodiments it is at least 1 or 3 mA.

In a preferred embodiment of the invention, the field is applied for a duration of between 10 and 140 msec. In other preferred embodiments it is applied for between 20 and 100 msec, or 60 and 90 msec.

In a preferred embodiment of the invention, the delay is less than 70 msec. In other preferred embodiments it is less than 40, 20, 5 or 1 msec. In some embodiments the delay is substantially equal to zero.

In a preferred embodiment of the invention, the delay is at least 1 msec. In other preferred embodiments it may be more than 3, 7, 15 or 30 msec.

In a preferred embodiment of the invention, the electric field has an exponential temporal envelope. In others it has a square, triangular, ramped or biphasic temporal envelope. Preferably the electric field comprises an AC electric field, preferably having a sinusoidal, saw tooth or square wave temporal envelope.

In a preferred embodiment of the invention, wherein the portion of the chamber has an inside surface and an outside surface, wherein the field is applied along the inner surface.

In a preferred embodiment of the invention, wherein the portion of the chamber has a normal conduction direction, wherein the field is applied along the normal conduction direction.

In a preferred embodiment of the invention, wherein the portion of the chamber has a normal conduction direction, wherein the field is applied perpendicular to the normal conduction direction.

In a preferred embodiment of the invention, the field is applied between at least two electrodes. Preferably, the electrodes are at least 2 cm apart. In some preferred embodiments the electrodes are at least 4 or 9 cm apart.

The chamber may be any of the left ventricle, the left atrium, the right ventricle or the right atrium.

A preferred embodiment of the invention includes pacing the heart. Preferably, applying the electric field is synchronized with the pacing.

In a preferred embodiment of the invention, the method includes calculating the delay based on the pacing.

In a preferred embodiment of the invention, the method includes sensing a specific activation at a site.

There is further provided, in accordance with a preferred embodiment of the invention, a method of modifying the activation profile of at least a portion of a heart, comprising,
- mapping the activation profile of the portion;
- determining a desired change in the activation profile; and
- blocking the activation of at least a segment of the portion, to achieve the desired change, wherein the segment is not part of a reentry circuit or an arrhythmia foci in the heart.

In a preferred embodiment of the invention, the blocked segment is an ischemic segment.

There is further provided, in accordance with a preferred embodiment of the invention a method of modifying the activation profile of at least a portion of a heart, comprising,
- mapping the activation profile of the portion;
- determining a desired change in the activation profile; and
- changing the refractory period of at least a segment of the portion, to achieve the desired change, wherein the segment is not part of a reentry circuit or an arrhythmia foci in the heart.

There is further provided, in accordance with a preferred embodiment of the invention a method of modifying the heart rate of a heart, comprising:
- providing a subject having a heart with an active natural pacemaker region; and
- applying a non-excitatory electric field to the region.

Preferably, the electric field extends a duration of an action potential of the region.

Preferably the method comprises extending the refractory period of a significant portion of the right atrium.

There is further provided, in accordance with a preferred embodiment of the invention a method of reducing an output of a chamber of a heart, comprising:
- determining the earliest activation of at least a portion of the chamber, which portion is not part of an abnormal conduction pathway in the heart; and
- applying a non-excitatory electric field to the portion.

Preferably, the field is applied prior to activation of the portion.

Preferably, the field reduces the reactivity of the portion to an activation signal.

Preferably, the field reduces the sensitivity of the portion to an activation signal.

There is further provided, in accordance with a preferred embodiment of the invention a method of reducing an output of a chamber of a heart, comprising:
- determining an activation of and conduction pathways to at least a portion of the chamber; and
- reversibly blocking the conduction pathways, using a locally applied non-excitatory electric field.

There is further provided, in accordance with a preferred embodiment of the invention a method of reducing an output of a chamber of a heart, comprising:
- determining an activation of and a conduction pathway to at least a portion of the chamber, which portion is not part of an abnormal conduction pathway in the heart; and
- reversibly reducing the conduction velocity in the conduction pathway, using a locally applied electric field.

There is further provided, in accordance with a preferred embodiment of the invention a method of performing cardiac surgery, comprising:
- blocking the electrical activity to at least a portion of the heart using a non-excitatory electric field; and
- performing a surgical procedure on the portion.

There is further provided, in accordance with a preferred embodiment of the invention a method of performing cardiac surgery, comprising:
- reducing the sensitivity to an activation signal of at least a portion of the heart using a non-excitatory electric field; and
- performing a surgical procedure on the portion.

There is further provided, in accordance with a preferred embodiment of the invention a method of controlling the heart, comprising,
- providing a subject having a heart with a left ventricle and a right ventricle;
- selectively reversibly increasing the contractility of one of the ventricles relative to the other ventricle.

Preferably, selectively reversibly increasing comprises applying a non-excitatory electric field to at least a portion of the one ventricle.

There is further provided, in accordance with a preferred embodiment of the invention a method of controlling the heart, comprising,
- providing a subject having a heart with a left ventricle and a right ventricle;
- selectively reversibly reducing the contractility of one of the ventricles, relative to the other ventricle.

Preferably, selectively reversibly reducing comprises applying a non-excitatory electric field to at least a portion of the one ventricle.

There is further provided, in accordance with a preferred embodiment of the invention a method of treating a segment of a heart which is induces arrhythmias due to an abnormally low excitation threshold, comprising:
- identifying the segment; and
- applying a desensitizing electric field to the segment, such that the excitation threshold is increased to a normal range of values.

There is further provided, in accordance with a preferred embodiment of the invention a method of modifying an activation profile of at least a portion of a heart, comprising:
- determining a desired change in the activation profile; and
- reversibly blocking the conduction of activation signals across a plurality of elongated fence portions of the heart to achieve the desired change.

Preferably, blocking the conduction creates a plurality of segments, isolated from external activation, in the portion of the heart. Preferably, at least one of the isolated segments contains an arrhythmia foci. Preferably, at least one of the isolated segments does not contain an arrhythmia foci.

Preferably, the method includes individually pacing each of at least two of the plurality of isolated segments.

Preferably, blocking the conduction limits an activation front from traveling along abnormal pathways.

Preferably, reversibly blocking comprises reversibly blocking conduction of activation signals, synchronized with a cardiac cycle, to block abnormal activation signals.

In a preferred embodiment of the invention reversibly blocking comprises reversibly blocking conduction of activation signals, synchronized with a cardiac cycle, to pass normal activation signals.

There is further provided, in accordance with a preferred embodiment of the invention a method of treating abnormal activation of the heart, comprising:

detecting an abnormal activation state; and modifying the activation of the heart in accordance with the above described method to stop the abnormal activation condition.

In a preferred embodiment of the invention the abnormal condition is fibrillation.

There is further provided, in accordance with a preferred embodiment of the invention a method of controlling the heart comprising:

determining a desired range of values for at least one parameter of cardiac activity; and controlling at least a local force of contraction in the heart to maintain the parameter within the desired range.

Preferably, controlling includes controlling the heart rate.

Preferably, controlling includes controlling a local conduction velocity.

Preferably, the parameter responds to the control with a time constant of less than 10 minutes. Alternatively it responds with a time constant of more than a day.

There is further provided, in accordance with a preferred embodiment of the invention a method of controlling the heart, comprising:

determining a desired range of values for at least one parameter of cardiac activity;

controlling at least a portion of the heart using a non-excitatory electric field having at least one characteristic, to maintain the parameter within the desired range; and changing the at least one characteristic in response to a reduction in a reaction of the heart to the electric field.

Preferably, the characteristic is a strength of the electric field. Alternatively it comprises a duration of the electric field, a frequency of the field or a wave form of the field.

There is further provided, in accordance with a preferred embodiment of the invention a method of treating a patient having a heart with an unhealed infarct, comprising, applying any of the above methods, until the infarct is healed.

There is further provided, in accordance with a preferred embodiment of the invention a method of treating a patient having a heart, comprising, providing a patient, having an unhealed infarct in the heart; and applying one of the above methods until the heart is stabilized.

In a preferred embodiment of the invention applying a non-excitatory field comprises applying a non-excitatory field for between 3 and 5000 heart beats.

There is further provided, in accordance with a preferred embodiment of the invention apparatus for controlling a heart comprising:

a plurality of electrodes adapted to apply an electric field across at least a portion of the beart; and a power supply which electrifies the electrodes with a non-excitatory electric field, for a given duration at least 100 times during a period of less than 50,000 cardiac cycles.

Preferably, are electrified at least 1000 times during a period of less than 50,000 cardiac cycles. They may also be electrified at least 1000 times during a period of less than 20,000 cardiac cycles or at least 1000 times during a period of less than 5,000 cardiac cycles.

Preferably, the field is applied less than 10 times in one second.

In a preferred embodiment of the invention, the power supply electrifies the electrodes at least 2000 times over the period. In preferred embodiments the power supply electrifies the electrodes at least 4000 times over the period.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein at least one of the electrodes is adapted to cover an area of the heart larger than 2 $cm^2$.

Preferably at least one of the electrodes is adapted to cover an area of the heart larger than 6 or 9 $cm^2$.

There is further provided, in accordance with a preferred embodiment of the invention apparatus for controlling a heart comprising:

at least one unipolar electrode adapted to apply an electric field to at least a portion of the heart; and a power supply which electrifies the electrodes with a non-excitatory electric field.

Preferably the apparatus comprises a housing, which is electrified as a second electrode.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein the distance between the electrodes is at least 2 cm.

In preferred embodiments of the invention the distance is at least 4 or 9 cm.

There is further provided, in accordance with a preferred embodiment of the invention apparatus for controlling a heart comprising:

at least three electrodes adapted to apply an electric field across at least a portion of the heart; and a power supply which electrifies the electrodes with a non-excitatory electric field, for a given duration, wherein the electrodes are selectively electrifiable in at least a first configuration where two electrodes are electrified and in a second configuration where two electrodes, not both identical with the first configuration electrodes, are electrified.

There is further provided, in accordance with a preferred embodiment of the invention apparatus for controlling a heart comprising:

a plurality of electrodes adapted to apply an electric field across at least a portion of the heart;

a sensor which senses a local activation; and a power supply which electrifies the electrodes with a non-excitatory electric field, for a given duration, responsive to the sensed local activation.

Preferably the sensor senses a mechanical activity of the portion.

Preferably, the sensor is adapted to sense the activation at at least one of the electrodes.

Preferably, the sensor is adapted to sense the activation in the right atrium.

Preferably, the sensor is adapted to sense the activation between the electrodes.

Preferably, the sensor senses an earliest activation in a chamber of the heart including the portion and wherein the power supply times the electrification responsive to the earliest activation.

There is further provided, in accordance with a preferred embodiment of the invention apparatus for controlling a heart comprising:

electrodes adapted to apply an electric field across elongate segments of at least a portion of the heart; and a power supply which electrifies the electrodes with a non-excitatory electric field.

Preferably, the electrodes are elongate electrodes at least one cm long. In other embodiments they are at least 2 or 4 cm long. Preferably the segments are less than 0.3 cm wide. In some embodiments they are less than 0.5, 1 or 2 cm wide.

Preferably, the power supply electrifies the electrodes for a given duration of at least 20 msec, at least 1000 times over a period of less than 5000 cardiac cycles.

In preferred embodiments of the invention, the elongate segments divide the heart into at least two electrically isolated segments in the heart.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration; and a circuit for determining an activation at a site in the portion, wherein the power supply electrifies the electrodes responsive to the determined activation.

Preferably, the electric field is applied at a given delay, preferably less than 70 msec, after an activation at one of the electrodes.

In a preferred embodiment of the invention the electric field is applied before an activation at one of the electrodes. In various preferred embodiments of the invention the field is applied more than 30, 50 or 80 msec before the activation.

Preferably, the circuit comprises an activation sensor which senses the activation. Alternatively or additionally the activation is calculated, preferably based on an activation in a chamber of the heart different from a chamber including the portion.

Preferably the apparatus includes a memory which stores values used to calculate a delay time, associated with a value of at least a parameter of a sensed ECG. Preferably, the parameter is a heart rate.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration;

a sensor which measures a parameter of cardiac activity; and a controller which controls the electrification of the electrodes to maintain the parameter within a range of values.

The apparatus preferably comprises a memory which stores a map of electrical activity in the heart, wherein the controller uses the map to determine a desired electrification.

The apparatus preferably comprises a memory which stores a model of electrical activity in the heart, wherein the controller uses the model to determine a desired electrification.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration; and a controller which measures a reaction of the heart to the electrification of the electrodes.

Preferably, the controller changes the electrification based on the measured reaction. Preferably, the apparatus includes a memory which stores the measured reaction.

There is further provided, in accordance with a preferred embodiment of the invention apparatus for controlling a heart comprising:

a plurality of electrodes adapted to apply an electric field across at least a portion of the heart;

a power supply which electrifies the electrodes with a non-excitatory electric field, for a given duration; and a pacemaker which paces the heart.

Preferably, the pacemaker and the remainder of the apparatus are contained in a common housing.

Preferably, the pacemaker and the remainder of the apparatus utilize common excitation electrodes. Preferably, the pacemaker and the remainder of the apparatus utilize a common power supply.

Preferably, the non-excitatory field is synchronized to the pacemaker.

Preferably, the electrodes are electrified using a single pulse which combines a pacing electric field and a non-excitatory electric field.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein at least one of the electrodes is mounted on a catheter.

There is further provided, in accordance with a preferred embodiment of the invention apparatus for controlling a heart comprising:

a plurality of electrodes adapted to apply an electric field across at least a portion of the heart; and a power supply which electrifies the electrodes with a non-excitatory electric field, for a given duration, wherein the electrodes are adapted to be applied externally to the body.

Preferably, the apparatus includes an external pacemaker.

Preferably, the apparatus comprises an ECG sensor, to which electrification of the electrodes is synchronized.

In a preferred embodiment of the invention the duration of the field is at least 20 msec. In other preferred embodiments the duration is at least 40, 80 or 120.

In a preferred embodiment of the invention a current is forced through the portion, between the electrodes.

Preferably, the apparatus includes at least another two electrodes, electrified by the power supply and adapted to apply a non-excitatory electric field across a second portion of the heart. Preferably, the apparatus comprises a controller which coordinates the electrification of all the electrodes in the apparatus.

Preferably, a peak current through the electrodes is less than 20 mA. In some preferred embodiments it is less than 10, 5 or 2 mA.

In preferred embodiments of the invention the electrodes are adapted to be substantially in contact with the heart.

Preferably the electric field has an exponential, triangular or square wave shape. The field may be unipolar or bipolar. The field may have a constant strength.

There is further provided, in accordance with a preferred embodiment of the invention apparatus for optical control of a heart, comprising:

at least one implantable light source which generates pulses of light, for at least 1000 cardiac cycles, over a period of less than 5000 cycles; and at least one wave guide for providing non-damaging intensities of light from the light source to at lest one site on the heart.

Preferably, the at least one light source comprises a plurality of light sources, each attached to a different site on the heart.

Preferably, the wave guide is an optical fiber.

Preferably, the light source comprises a monochrome light source.

In a preferred embodiment of the invention the apparatus comprises a sensor, which measures an activation of at least portion of the heart, wherein the light source provides pulsed light in synchrony with the measured activation.

There is further provided, in accordance with a preferred embodiment of the invention a method of programming a programmable controller for a subject having a heart, comprising:

determining pulse parameters suitable for controlling the heart using non-excitatory electric fields; and programming the controller with the pulse parameters.

Preferably, determining pulse parameters comprises determining a timing of the pulse relative to a cardiac activity.

Preferably, the cardiac activity is a local activation.

Preferably, determining a timing comprises determining timing which does not induce fibrillation in the heart.

Preferably, determining a timing comprises determining a timing which does not induce an arrhythmia in the heart.

Preferably, determining a timing comprises determining the timing based on a map of an activation profile of the heart.

Preferably, determining a timing comprises calculating a delay time relative to a sensed activation.

Preferably, controlling the heart comprises modifying the contractility of the heart.

There is further provided, in accordance with a preferred embodiment of the invention a method of determining an optimal placement of at least two individual electrodes for controlling a heart using non-excitatory electric fields, comprising:

determining an activation profile of at least a portion of the heart; and determining an optimal placement of the electrodes in the portion based on the activation profile.

Preferably the method includes determining an optimal location for an activation sensor, relative to the placement of the electrodes.

Preferably, controlling comprises modifying the contractility.

Preferably, controlling comprises creating elongate non-conducting segments in the heart.

There is further provided, in accordance with a preferred embodiment of the invention a method of determining a timing parameter for a non-excitatory, repeatably applied pulse for a heart, comprising:

applying a non-excitatory pulse using a first delay;

determining if the pulse induces an abnormal activation profile in the heart; and repeating applying a non-excitatory pulse using a second delay, shorter than the first, if the pulse did not induce abnormal activation in the heart.

There is further provided, in accordance with a preferred embodiment of the invention a method of determining a timing parameter for a non-excitatory, repeatably applied pulse for a heart, comprising:

applying a non-excitatory pulse using a first delay;

determining if the pulse induces an abnormal activation profile in the heart; and repeating applying a non-excitatory pulse using a second delay, longer than the first, if the pulse did not induce abnormal activation in the heart.

There is further provided, in accordance with a preferred embodiment of the invention a method of programming a programmable controller for a heart, comprising:

controlling the heart using plurality of non-excitatory electric field sequences;

determining a response of the heart to each of the sequences; and programming the controller responsive to the response of the heart to the non-excitatory sequences.

There is further provided, in accordance with a preferred embodiment of the invention a method of controlling an epileptic seizure, comprising:

detecting an epileptic seizure in brain tissue; and applying a non-excitatory electric field to the brain tissue to attenuate conduction of a signal in the tissue.

There is further provided, in accordance with a preferred embodiment of the invention a method of controlling nervous signals in periphery nerves, comprising, selecting a nerve; and applying a non-excitatory electric field to the nerve to attenuate conduction of nervous signals in the nerve.

There is further provided, in accordance with a preferred embodiment of the invention a method of controlling a heart having a chamber comprising:

applying a non-excitatory electric field to a first portion of a chamber, such that a force of contraction of the first portion is lessened; and applying a non-excitatory electric field to a second portion of a chamber, such that a force of contraction of the second portion is increased. heart beat. Alternatively or additionally, the delay is at least 0.5 or 1 msec, optionally, 3 msec, optionally 7 msec and also optionally 30 msec.

There is further provided in accordance with a preferred embodiment of the invention, a method of controlling the heart including determining a desired range of values for at least one parameter of cardiac activity and controlling at least a local contractility and a local conduction velocity in the heart to maintain the parameter within the desired range.

Preferably, the parameter responds to the control with a time constant of less than 10 minutes, alternatively, the parameter responds to the control with a time constant of between 10 minutes and 6 hours, alternatively, with a time constant of between 6 hours and a day, alternatively, with a time constant between a day and a week, alternatively, a time constant of between a week and month, alternatively, a time constant of over a month.

There is also provided in accordance with a preferred embodiment of the invention, a method of controlling the heart, including determining a desired range of values for at least one parameter of cardiac activity, controlling at least a portion of the heart using a non-excitatory electric field having at least one characteristic, to maintain the parameter within the desired range and changing the at least one characteristic in response to a reduction in a reaction of the heart to the electric field. Preferably, the characteristic is the strength of the electric field. Alternatively or additionally, the characteristic is one or more of the duration of the electric field, its timing, wave form, and frequency.

In another preferred embodiment of the invention, the apparatus includes a sensor which measures a parameter of cardiac activity and a controller which controls the electrification of the electrodes to maintain the parameter within a range of values. Preferably, the apparatus includes a memory which stores a map of electrical activity in the heart, wherein the controller uses the map to determine a desired electrification. Alternatively or additionally, the apparatus includes a memory which stores a model of electrical activity in the heart, wherein the controller uses the model to determine a desired electrification.

There is also provided in accordance with a preferred embodiment of the invention, a method of controlling an epileptic seizure, including detecting an epileptic seizure in brain tissue and applying a non-excitatory electric field to the brain tissue to attenuate conduction of a signal in the tissue.

BRIEF DESCRIPTION OF THE DRAWINGS

The present invention will be more clearly understood from the detailed description of the preferred embodiments and from the attached drawings in which:

FIG. 8B is a series of graphs showing the repeatability of increasing contractility in various types of cardiac muscles, in accordance with a preferred embodiment of the invention;

DETAILED DESCRIPTION OF THE PREFERRED EMBODIMENTS

One aspect of the present invention relates to controlling and/or modulating the contractility of a cardiac muscle segment and/or the plateau duration of an action potential of the cardiac muscle segment, by applying an electric field or current across the segment. As used herein, the terms, voltage, electric field and current are used interchangeably to refer to the act of supplying a non-excitatory signal to control cardiac activity. The actual method of applying the signal is described in more detail below.

Figure 1A:
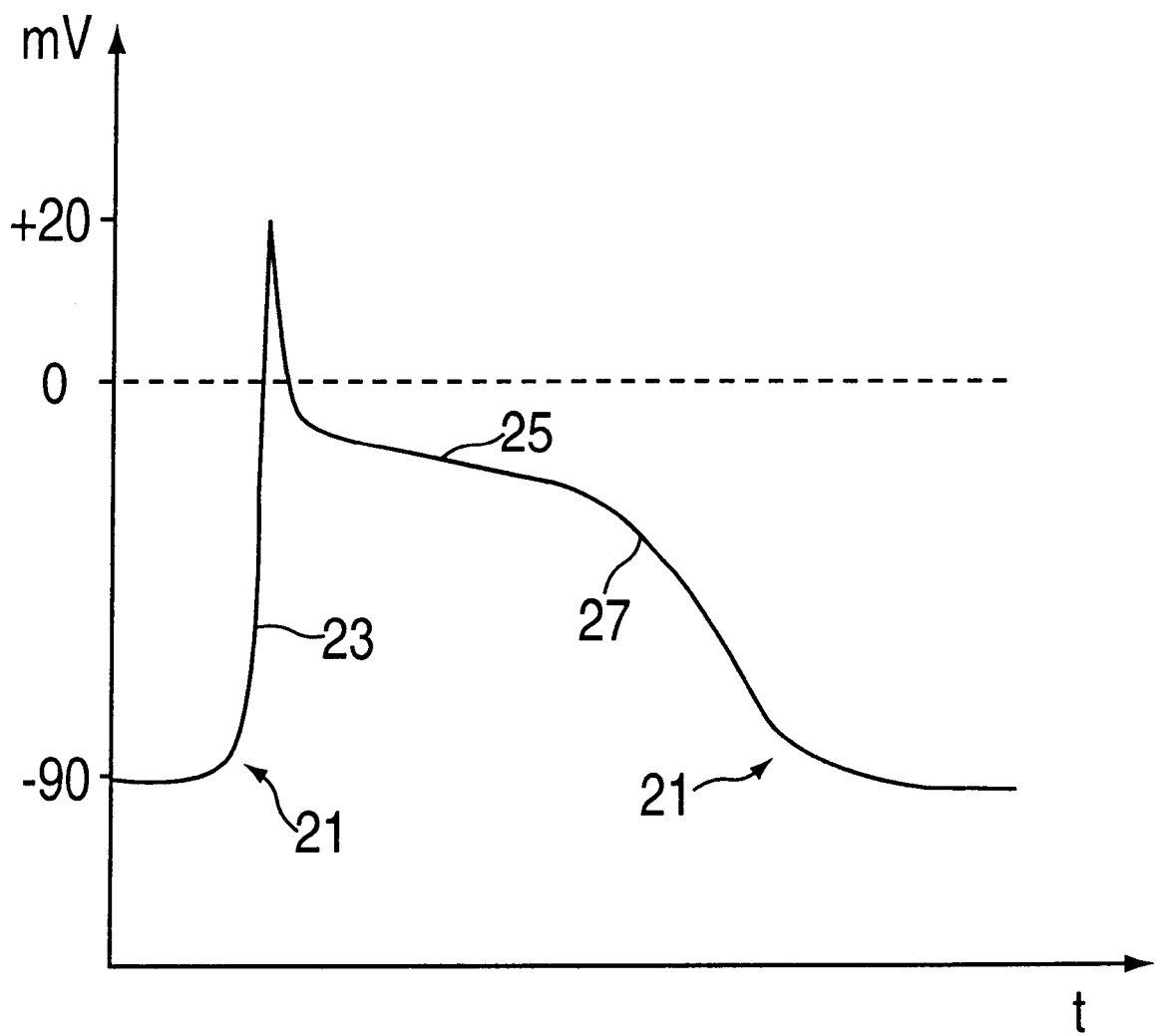
FIG. 1A is a schematic graph of a typical cardiac muscle action potential.
Figure 1B:
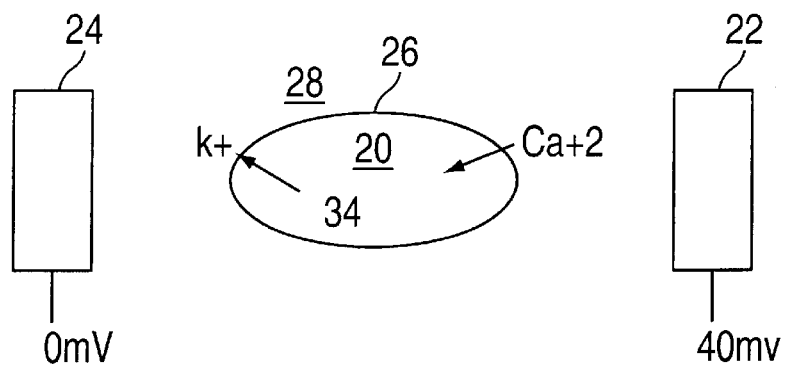
FIG. 1B is a schematic model of a cardiac muscle cell in an electrical field.

FIG. 1B shows a schematic model illustrating one possible explanation for the relation between an applied voltage and a resulting plateau duration. A cell 20, having a membrane 26, surrounded by extra-cellular fluid 28, is located in an electrical field generated by an electrode 22 and an electrode 24. Cell 20 has a −40 mV internal potential across membrane 26, electrode 22 has a potential of 40 mV and electrode 24 is grounded (to the rest of the body). During the action potential plateau, calcium ions enter the cell and potassium ions leave the cell through different membrane proteins. In this model, the external electric field caused by the voltage on the electrodes increases the potential of extra-cellular fluid 28. This reduces the outward movement of potassium ions from inside cell 20 and/or forces calcium ions into cell 20, either by changing the membrane potential, thus changing the electrochemical driving force of ions from both sides of the membrane or by changing the number of ionic channels being opened or closed.

In an additional or alternative model, the electric field generated by electrodes 22 and 24 causes an ionic flow between them. This flow is carried mainly by chlorine and potassium ions, since these are the ions to which membrane 26 is permeable, however, calcium ions may also be affected. In this model, calcium ions are drawn into cell 20 by the current while potassium ions are removed. Alternatively or additionally, sodium ions are removed instead of potassium ions. In any case, the additional calcium ions in the cell increase the contractility of cell 20 and are believed to extend the plateau duration.

Another additional or alternative model is that the electric field and/or the ionic current affect the opening and closing of voltage-gated channels (sodium, potassium and sodium-calcium). Further, the field may affect the operation of ionic pumps. One possible mechanism for this effect is that the applied electric field generates local "hot spots" of high electrical fields in the cell membrane, which hot spots can affect the opening and closing of ionic channels and/or pumps. Since creation of the hot spots is generally asymmetric with respect to the cell and since the channels themselves have an asymmetric behavior with respect to applied fields, more channels may be opened at one end of the cell than at the other. If, for example, more channels open at the negative end of the cell than at the positive end of the cell, the inflow of calcium ions will be greater than the outflow of these ions.

In accordance with yet another model, the controlling electric field increases the concentration of calcium in intracellular stores, which increased concentration may cause increased and/or faster supply of calcium during contraction, increasing the contractile force. Alternatively or additionally, the controlling electric field may directly affect the rate at which calcium is made available from the intracellular store, during contraction of the cell. Also, it may be that the controlling electric field directly increases the efficiency of the inflow of calcium, which causes an increase in the availability of calcium from the intracellular stores. It should be noted that in some physiological models of myocyte contraction, it is the rate of calcium flow which determines the contractility, rather than the total amount of calcium.

Different types of ionic channels and pumps have different operating characteristics. These characteristics include rates of flow, opening and closing rates, triggering voltage levels, priming and dependency on other ions for operating. It is thus possible to select a particular type of ionic channel by applying a particular strength of electric field, which strength also depends on whether the channels are open or closed at that moment, i.e., on the depolarization/repolarization phase of the cell. Different attributes of cellular activity may be controlled by controlling the ionic channels in this manner, since the activity of excitable tissues are well determined by their transmembrane potential and the concentrations of various types of ions inside and outside the cell.

Another model is that applying a non-excitatory electric fields induces the release of catecholamines (from nerve endings) at the treated portion of the heart. Another possibility is that the applied field facilitates the absorption of existing catecholamines by the cell.

Another, "recruitment", model, hypothesizes that the non-excitatory pulse recruits cardiac muscle fibers which are otherwise not stimulated by the activation signal. The non-excitatory pulse may work by lowering their depolarization threshold or by supplying a higher strength activation signal than is normal. However, it is generally accepted that cardiac muscle fibers function as a syncytium such that each cell contracts at each beat. See for example, "Excitation Contraction Coupling and Cardiac Contractile Force", by Donald M. Bers, Chapter 2, page 17, Kluwer Academic, 1991.

Most probably, one or more of these models may be used to explain the activity of cell 20 during different parts of the activation cycle. However, several major effects, including, increasing contractility, changing the self-activation rate, rescheduling of the repolarization, extension of plateau duration, hyperpolarization of cells, changing of membrane potential, changing of conduction velocity and inactivation of cells using electric fields, can be effected without knowing which model, if any, is correct.

As can be appreciated, the direction of the electric field may be important. First, conduction in cardiac cells is very anisotropic. Second, the distribution of local irregularities in the cell membrane is not equal, rather, irregularities are more common at ends of the cell; in addition, one cell end is usually more irregular than the other cell end. These irregularities may govern the creation of local high electric fields which might affect ionic channels. Third, some cardiac structures, such as papillary muscles, are better adapted to conduct an activation signal in one direction than in an opposite direction. Fourth, there exist rhythmic depolarization signals originating in the natural conductive system of the heart which are caused by the depolarization and repolarization of the heart muscle tissue itself. These signals may interfere with an externally applied electric field.

In one preferred embodiment of the invention, the purpose of a particular electric field is to induce an ionic current which is opposite to an ionic current induced by the voltage potential caused by the rhythmic depolarization of the heart. For example, the action potential plateau duration in cardiac muscle cells further from the earliest activation location is typically shorter than the duration of those cells nearer the earliest activation location. This shortening may result from different local ionic currents caused by the depolarization and repolarization of the heart and/or by different ionic current kinetics behavior at these locations. These ionic currents can be negated by applying an electric field of an equal magnitude and opposite direction to the field generated by the rhythmic depolarization.

Figure 2:
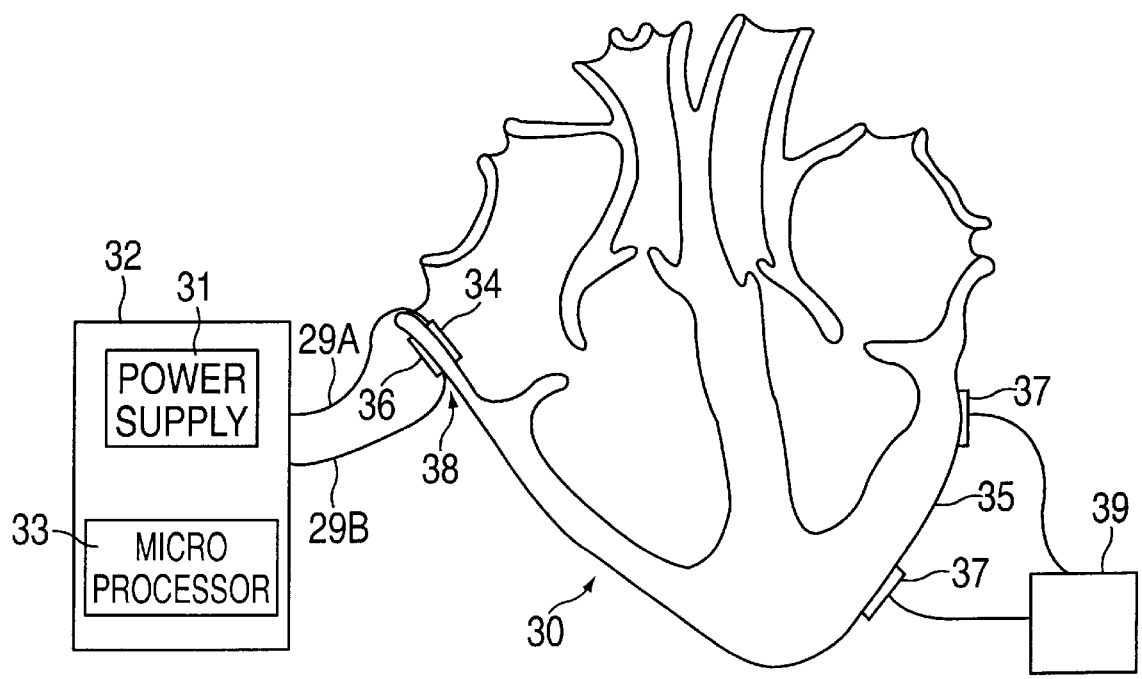
FIG. 2 is a schematic diagram of a heart having segments controlled in accordance with embodiments of the present invention.

FIG. 2 shows a heart 30 which is controlled using an electrical controller 32. A segment 38 of the right atrium is a controlled segment. In one preferred embodiment of the invention, the casing of controller 32 is one electrode and an electrode 36 is a second electrode for applying an electric field to segment 38. In another preferred embodiment of the invention, a second electrode 34 is used instead of the casing of controller 32. In a further preferred embodiment of the invention, the body of controller 32 is a ground, so that both electrode 34 and electrode 36 can be positive or negative relative to the rest of the heart. In another embodiment, electrode 34 is not directly connected to heart 30, rather, electrode 34 is floating inside the heart. In this embodiment, electrode 34 is preferably the current drain electrode. For illustrative purposes, controller 32 is shown including a power supply 31, leads 29A and 29B connecting the controller to the electrodes and a microprocessor 33 which controls the electrification of the electrodes.

In an alternative embodiment, also shown in FIG. 2, the electric field is applied along the heart wall, rather than across it. A segment 35 of the left ventricle is shown to be controlled by two electrodes 37 operated by a controller 39. Electrodes 37 may be placed on the surface of heart 30, alternatively, electrodes 37 may be inserted into the heart muscle. Further alternatively, the electrodes may be placed in blood vessels or in other body tissues which are outside of the heart, providing that electrifying the electrodes will provide a field or current to at least a portion of the heart. It should be noted that, since the control is synchronized to the cardiac cycle, even if the electrodes are outside the heart, there is substantially no change in position of the heart between sequential heart beats, so substantially the same portion of the heart will be affected each cardiac cycle, even if the electrodes are not mechanically coupled to the heart.

It another alternative embodiment of the invention, more than one pair of electrodes is used to control segment 35. In such an embodiment, each pair of electrodes may be located differently with respect to segment 35, for example, one pair of electrodes may be placed on the epicardium and a second pair placed inside the myocardium.

It should be appreciated that a current induced between the electrodes may cause electrolytic deposition on the electrodes over a period of time and/or may cause adverse physiological reactions in the tissue. To counteract this effect, in a preferred embodiment of the invention, the electric field is an AC electric field. In one preferred embodiment, the direction of the field is switched at a relatively low frequency, equal to or lower than the cardiac cycle rate. Preferably, the phase is inverted during a particular phase of the cardiac cycle, for example, during diastole. In another preferred embodiment of the invention, the electric field has a frequency which is significantly higher than the cardiac cycle frequency.

Fast sodium channels, once inactivated require a certain amount of time at a negative potential to become ready for activation. As described, for example, in "Ionic Channels of Excitable Membranes", Bertil Hille, chapter 2, pp. 40–45, Sinaur Associates Inc., the disclosure of which is incorporated herein by reference. Since most sodium channels are not activated immediately at the onset of depolarization, applying a voltage at a high enough frequency can open the few channels that do react quickly to potential changes, while most of the channels will become inactivated and will not leave the inactivation stage. Thus, if the frequency of the field is high enough, certain ionic channels can be kept closed even though the average voltage is zero, with the result that the stimulated tissue is non-excitatory.

In accordance with another preferred embodiment of the invention, an AC field is overlaid on a DC field for controlling the heart. For example, an AC field having a amplitude of 20% that of the DC field and a frequency of 1 kHz may be used. Such an AC/DC controlling field has the advantage that the change in the applied field is higher, so that any reactions (on the part of the muscle cell) to changes in the field are facilitated, as are any reactions to the intensity of the field. The AC field in a combined AC/DC field or in a pure AC type field may have a temporal form of a sawtooth, a sinusoid or another form, such as an exponential or square wave pulse form.

In a DC type field, the temporal form of the field is preferably that of a constant amplitude pulse. However, in other embodiment of the invention, a triangular pulse, an exponential pulse, a ramp shaped pulse (increasing or decreasing), and/or a biphasic pulse form may be used.

Both AC and DC fields may be unipolar or bipolar. The terms AC and DC as used herein to describe the electric field, relate to the number of cycles in a pulse. A DC field has at most one cycle, while an AC field may comprise many cycles. In other preferred embodiments of the invention, a train of pulses may be applied, each train being of an AC or of a DC type.

Various types of ionic electrodes, such as Ag—AgCl electrodes, platinum electrodes, titanium electrodes with coatings such as nitrides and carbides, coated tantalum electrodes, pyrocarbon electrodes or carbon electrodes may be used. These electrodes generally reduce the amount of electro-deposition. The electrodes may be square, rectangular, or of any other suitable shape and may be attached by screwing the electrode into the myocardium or by clamping or by other attachment methods.

There are two preferred methods of delivering an electric field to a segment of the heart. In a first method, a current is forced through the segment of the heart which is to be controlled. Preferably, the current is a constant DC current. However, an AC current, as described above may also be used. In a second method, an electric field is applied across the heart (and maintained at a constant strength relative to the signal from). Generally, applying an electric field is easier and requires less power than inducing a current.

The timing of the application of the electric field (or current) relative to the local activity at segment 38 and relative to the entire cardiac cycle is important. In general, the application of the field may be synchronized to the local activation time if a local effect is desired, such as increasing the local contractility and/or plateau duration. The application of the field may be synchronized to the cardiac cycle in cases where a global effect is desired. For example, by hyperpolarizing cells in synchrony with the cardiac cycle it is possible to time their excitability window such that certain arrhythmias are prevented, as described in greater detail below. The application of the field may also be synchronized in accordance with a model of how the heart should be activated, in order to change the activation profile of the heart. For example, to increase the output of the heart, conduction velocities and/or conduction pathways may be controlled so that the heart contracts in a sequence deemed to be more optimal than a natural sequence. In particular, by controlling the conduction velocity at the AV node and/or at the left and right branches the AV interval may be increased or reduced. It should however be appreciated that the difference in activation times between different parts of the heart, especially in the same chamber of the heart, is usually quite small. For example, the propagation time of an activation signal in the left ventricle is approximately between 15 and 50 msec. If the control function may be achieved even if the timing of the application of the controlling field is locally off by 5 or 10 msec, then the control function can be achieved using a single pair of controlling electrodes.

Although, it is usually simplest to determine the local activation using a measured electrical activation time, it should be appreciated that the local activation of a tissue segment may be determined based on changes in mechanical activity, changes in position, velocity of motion, acceleration and even transmembrane potentials. Further, since in diseased tissue the delay between electrical activation and mechanical activation may be longer than in healthy tissue, the timing of the application of the field is preferably relative to the mechanical activation of the muscle.

In a preferred embodiment of the invention, the timing of the field is relative to the actual transmembrane potentials in the segments, not those which may be estimated from the electrogram and/or the mechanical. Thus, initiation of the field may be timed to the onset of the plateau to increase contractility. Alternatively, application of the field may be timed to specific transmembrane voltage levels. Further preferably, the strength and/or other parameters of the field, may be determined responsive to the actual transmembrane potentials and ionic concentrations achieved in cells of the segment. One way of determining the actual voltage levels is to inject a voltage sensitive dye into the cell and monitor it using an optical sensor, such as known in the art in experimental settings. One way of monitoring ionic concentrations, both intracellular and extracellular is by using concentrations sensitive dyes.

If an electric field is applied before the activation signal reaches segment 38, the electric field can be used to reduce the sensitivity of segment 38 to the activation signal. One method of producing this effect is to apply a large electric field opposite to the direction of the activation signal and synchronized to it. This field will reduce the amplitude of the activation signal, so that it cannot excite cardiac tissue. Another method is to apply a strong positive potential on segment 38 before an activation signal reaches it, so that segment 38 is hyperpolarized and not sensitive to the activation signal. Removing the electric field does not immediately reverse this effect. Segment 38 stays insensitive for a short period of time and for a further period of time, the conduction velocity in segment 38 is reduced. In some cases however, removing the electric field will cause an action potential to occur. This action potential can be timed so that it occurs during a safe period with respect to the activation profile of the heart, so that if the segment generates an activation signal, this signal will not be propagated to other parts of the heart. In some cases, the application of the field may affect the reactivity of the cells to the electrical potential rather and, in other, it may extend the refractory period. It should be noted that an electric field applied shortly after activation may also extend the refractory period, in addition to increasing the force contraction.

It should be noted that, since the cardiac cycle is substantially reported, a delay before the activation time and a delay after the activation time may both be embodied using a system which delays after the activation time. For example, a field which should be applied 20 msec before the activation time, may be applied instead 680 msec after (assuming the cycle length is 700 msec).

Other applications of electric fields can increase the conduction velocity, especially where the conduction velocity is low as a result of tissue damage. Another method of controlling conduction is to apply an electric field similar to that used for defibrillation. When applied during the repolarization period of these cells, this type of electric field delays the repolarization. During this delayed/extended repolarization the cells are non-excitable. It should be appreciated that if this "defibrillation field" is applied using the techniques described herein (small, local and synchronized to a local activation time) the heart itself will not be defibrillated by the electric field. In one preferred embodiment of the invention, a locally defibrillated portion of the heart is isolated, by fences, from the rest of the heart.

Figure 3:
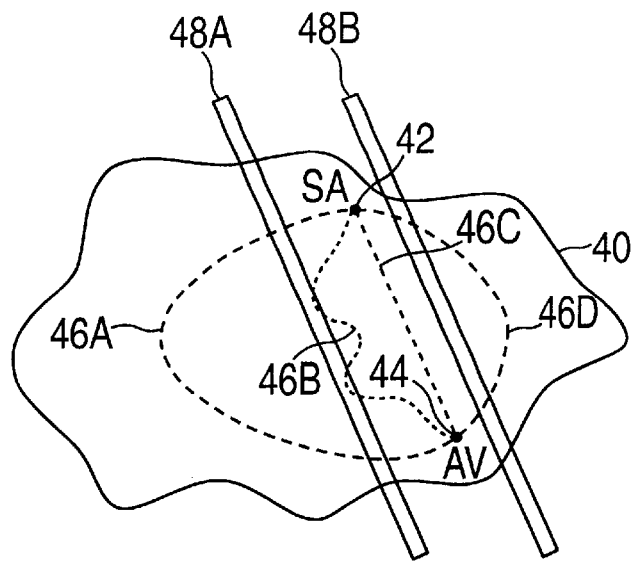
FIG. 3 is a schematic diagram of a segment of right atrial tissue with a plurality of conduction pathways, illustrating the use of fences, in accordance with a preferred embodiment of the present invention.

FIG. 3 illuminates one use of extending the refractory periods of cardiac tissue. Segment 40 is a portion of a right atrium. An activation signal normally propagates from an SA node 42 to an AV node 44. Several competing pathways, marked 46A–46D, may exist between SA node 42 and AV node 44, however, in healthy tissue, only one signal reaches AV node 44 within its excitability window. In diseased tissue, several signals which have traveled in different paths may serially excite AV node 44 even though they originated from the same action potential in the SA node. Further, in atrial fibrillation, the entire right atrium may have random signals running through it. In a preferred embodiment of the invention, electric fields are applied to a plurality of regions which act as "fences" 48A and 48B. These fences are non-conducting to activation signals during a particular, predetermined critical time, depending on the activation time of the electric fields. Thus, the activation signal is fenced in between SA node 42 and AV node 44. It is known to perform a surgical procedure with a similar effect (the "maze" procedure), however, in the surgical procedure, many portions of the right atrium need to be ablated to produce permanent insulating regions (fences). In the present embodiment of the invention, at least portions of fences 48A and 48B may be deactivated after the activation signal has passed, so that the atrium can contract properly.

In a preferred embodiment of the invention, a fence is applied using a linear array of bipolar electrodes. In another preferred embodiment of the invention, a fence is applied using two (slightly) spaced apart elongate wire electrodes of opposite polarity. Preferably, portions of the wire electrodes are isolated, such as segments 0.5 cm long being isolated and segments 0.5 cm long being exposed.

Still another preferred embodiment of the invention relates to treating ventricular fibrillation (VF). In VF, a ventricle is activated by more than one activation signal, which do not activate the ventricle in an orderly fashion. Rather, each segment of the ventricle is randomly activated asynchronously with the other segments of the ventricle and asynchronously with the cardiac cycle. As a result, no pumping action is achieved. In a preferred embodiment of the invention, a plurality of electrical fences are applied in the affected ventricle to damp the fibrillations. In general, by changing the window during which segments of the ventricle are sensitive to activation, a fibrillation causing activation signal can be blocked, without affecting the natural contraction of the ventricle. In one embodiment of the invention, the fences are used to channel the activation signals along correct pathways, for example, only longitudinal pathways. Thus, activation signals cannot move in transverse direction and transverse activation signals will quickly fade away, harmlessly. Healthy activation signals from the AV node will not be adversely affected by the fences. Alternatively or additionally, fences are generated in synchrony with the activation signal from the AV node, so that fibrillation causing activation signals are blocked. Further alternatively, entire segments of the ventricle are desensitized to the activation signals by applying a positive potential to those segments deemed sensitive to fibrillation.

Dividing the heart into insulated segments using fences is useful for treating many types of arrhythmias. As used herein, the term insulated means that conduction of the activation signal is blocked or slowed down or otherwise greatly reduced by deactivating portions of the heart conduction system. For example, many types of ventricular tachycardia (VT) and premature beats in the heart are caused by local segments of tissue which generate a pacing signal. These segments can be insulated from other segments of the heart so that only a small, local segment is affected by the irregular pacing. Alternatively, these diseased segments can be desensitized using an electric field, so that they do not generate incorrect activation signals at all.

Premature beats are usually caused by an oversensitive segment of the heart. By applying a local electric field to the segment, the sensitivity of the segment can be controlled and brought to similar levels as the rest of the heart, solving the major cause of premature beats. This technique is also applicable to insensitive tissues, which are sensitized by the application of a local electric field so that they become as sensitive as surrounding tissues.

It should be appreciated that it is not necessary to know the exact geometrical origin of an arrhythmia to treat it using the above described methods. Rather, entire segments of the heart can be desensitized in synchrony with the cardiac cycle so that they do not react before the true activation signal reaches them. Further, the heart can be divided into isolated segments or fenced in without mapping the electrical system of the heart. For example, electrodes can be inserted in the coronary vessels to create fences in the heart. These fences can block most if not all of the irregular activation signals in the heart and still allow "correct" activation signals to propagate by synchronizing the generation of these fences to the "correct" cardiac activation profile. Alternatively or additionally, each isolated segment is paced with an individual electrode. Alternatively, an array of electrodes may be implanted surrounding the heart so that it is possible to individually control substantially any local portion thereof.

In an additional preferred embodiment of the present invention, segments of the heart are continuously controlled using an electric field, so that their membrane potential at rest is below −60 mV. Below this level, the voltage-gated sodium channels cannot be opened by an activation signal. It is not usually possible to clamp all of the cells in a tissue segment to this voltage, so some of the cells in the tissue will typically be excitable. However, it is known that hyperpolarization causes depletion of potassium ions in the extracellular spaces surrounding individual cardiac muscle cells, which will cause a general reduction in the excitability of all the cells which share the same extracellular spaces. As described, for example, in "K+ Fluctuations in the Extracellular Spaces of Cardiac Muscle: Evidence from the Voltage Clamp and Extracellular K+—Selective Microelectrodes", Cohen I and Kline R, *Circulation Research,* Vol. 50, No. 1, pp. 1–16, January 1982, the disclosure of which is incorporated herein by reference. Thus, the reaction of the segments of the heart to an activation signal is reduced, has a longer delay and the propagation velocity in those segments is significantly reduced. Other resting potentials may affect the opening of other voltage-gated channels in the cell.

Another preferred embodiment of the invention relates to cardiac surgery. In many instances it is desirable to stop the pumping action of the heart for a few seconds or minutes necessary to complete a suture or a cut to operate on an aneurysm. Current practice is not very flexible. In one method, the heart is bypassed with a heart-lung machine and the heart itself is stopped for a long period of time. This process is not healthy for the patient as a whole or for the heart itself and, often, serious post-operative complications appear. In another method, the heart is cooled down to reduce its oxygen consumption and it is then stopped for a (non-extendible) period of a few minutes. The period is non-extendible in part since during the stoppage of the heart the entire body is deprived of oxygen. In these methods, the heart is usually stopped using a cardioplesic solution. In a third method fibrillation is induced in the heart. However, fibrillation is known to cause ischemia, due to the greatly increased oxygen demand during fibrillation and the blockage of blood flow in the coronary arteries by the contraction of the heart muscle. Ischemia can irreversibly damage the heart.

Cessation or reduction of the pumping activity of the heart may be achieved using methods described herein, for example, fencing. Thus, in a preferred embodiment of the invention, the pumping action of the heart is markedly reduced using techniques described herein, repeatedly and reversibly, for short periods of time. It should be appreciated that due to the simplicity of application and easy reversibility, stopping the heart using electrical control is more flexible than currently practiced methods. Electrical control is especially useful in conjunction with endoscopic heart surgery and endoscopic bypass surgery, where it is desirable to reduce the motion of small segments of the heart.

Another preferred embodiment of the present invention relates to treating ischemic portions of the heart. Ischemic portions, which may be automatically identified from their injury currents using locally implanted sensors or by other electro-physiological characterization, may be desensitized or blocked to the activation signal of the heart. Thus, the ischemic cells are not required to perform work and may be able to heal.

U.S. provisional application 60/009,769 titled "Cardiac Electromechanics", filed on Jan. 11, 1996, by Shlomo Ben-Haim and Maier Fenster, and it corresponding Israeli patent application No. 116,699 titled "Cardiac Electromechanics", filed on Jan. 8, 1996 by applicant Biosense Ltd., the disclosures of which are incorporated herein by reference, describe methods of cardiac modeling and heart optimization. In cardiac modeling, the distribution of muscle mass in the heart is changed by changing the workload of segments of the heart or by changing the plateau duration of action potentials at segments of the heart. These changes may be achieved by changing the activation profile of the heart. Plateau duration can be readily controlled using methods as described hereinabove. Further, by controlling the conduction pathways in the heart, according to methods of the present invention, the entire activation profile of the heart can be affected. In cardiac optimization as described in these applications, the activation profile of the heart is changed so that global parameters of cardiac output are increased. Alternatively, local physiological values, such as stress, are redistributed to relieve high-stress locations in the heart. In a preferred embodiment of the present invention, the activation profile may be usefully changed using methods as described hereinabove.

In order to best implement many embodiments of the present invention, it is useful to first generate an electrical, geometrical or mechanical map of the heart. U.S. patent application Ser. No. 08/595,365 titled "Cardiac Electromechanics", filed on Feb. 1, 1996, by Shlomo Ben-Haim, and two PCT applications filed in Israel, on even date as the instant application, by applicant "Biosense" and titled "Cardiac Electromechanics" and "Mapping Catheter", the disclosures of which are incorporated herein by reference, describe maps and methods and means for generating such maps. One particular map which is of interest is a viability map, in which the viability of different segments of heart tissue is mapped so as to identify hibernating and/or ischemic tissue. U.S. Pat. No. 5,391,199, U.S. patent application Ser. No. 08/293,859, filed on Aug. 19, 1994, titled "Means and Method for Remote Object Position and Orientation Detection System" and PCT patent application US95/01103, now published as WO96/05768 on Feb. 29, 1996, the disclosures of which are incorporated herein by reference, describe position sensing means suitable for mounting on a catheter which is especially useful for generating such maps. Such position sensing means may also be useful for correctly placing electrodes in the heart if the electrodes are implanted using minimally invasive techniques such as those using endoscopes, throactoscopes and catheters.

In one preferred embodiment of the invention, a map of the heart is used to determine which portions of the heart are viable, and thus, can be controlled to increase the cardiac output. Preferably, the entire activation profile of the heart is taken into account when determining to which portions of the heart a controlling field should be applied, to maximize a parameter of cardiac output. The activation profile may also determine the timing of the application of the field. A perfusion map may be used to access the blood flow to various portions of the heart. It is to be expected that increasing the contractility of a segment of heart muscle also increases the oxygen demand of that segment. Therefore, it is desirable to increase the contractility only of those segments which have a sufficient blood flow. Possibly, the oxygen demands of other segments of the heart is reduced by proper controlling of the activation sequence of the heart.

Alternatively or additionally to mapping the perfusion and/or viability of the heart, the onset of controlling the heart may be performed gradually. Thus, the cardiac blood supply has time to adapt to the increased demand (if any) and to changes in supply patterns. In addition, the increase in demand will not be acute, so no acute problems (such as a heart attack) are to be expected as a result of the controlling. In one embodiment, the controlling is applied, at first, only every few heart beats, and later, every heart beat. Additionally or alternatively, the duration of a controlling pulse is gradually increased over a long period of time, such as several weeks. Additionally or alternatively, different segments are controlled for different heart beats, to spread the increased demand over a larger portion of the heart.

In an alternative preferred embodiment of the invention, the contractility of the heart is controlled only during the day and not during the night, as the cardiac demand during the day time is typically greater than during the night. Alternatively or additionally, the controller is used for a short time, such as 15 minutes, in the morning, to aid the patient in getting up. Alternatively or additionally, a controlling electric field is applied only once every number of beats (day and/or night). Further alternatively, the heart is controlled for a short period of time following an acute ischemic event, until the heart recovers from the shock. One preferred controlling method which may be applied after a heart attack relates to preventing arrhythmias. Another preferred controlling is desensitizing infarcted tissue or reducing the contractility of such tissue or electrically isolating such tissue so as to reduce its oxygen demands and increase its chance of healing.

One benefit of many embodiments of the present invention, is that they can be implemented without making any structural or other permanent changes in the conduction system of the heart. Further, many embodiments may be used in conjunction with an existing pacemaker or in conjunction with drug therapy which affects the electrical conduction in the heart. In addition, different controlling schemes may be simultaneously practiced together, for example, controlling the heart rate and increasing contractility in the left ventricle.

It must be appreciated however, that, by changing the activation profile of the heart, some changes may be effected on the structure of the heart. For example, cardiac modeling, as described above, may result from activation profile changes, over time.

Figure 4A:
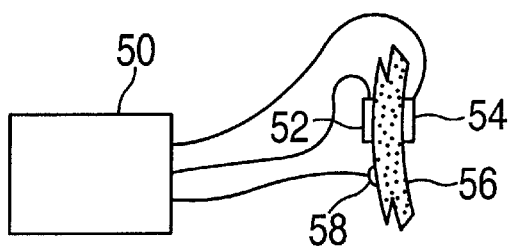
FIG. 4A is a schematic diagram of an electrical controller connected to a segment of cardiac muscle, in accordance with a preferred embodiment of the invention.

FIG. 4A is a schematic diagram of an electrical controller 50, in operation, in accordance with a preferred embodiment of the invention. A muscle segment 56, which is controlled by controller 50, is preferably electrified by at least one electrode 52 and preferably by a second electrode 54. Electrode 54 may be electrically floating. A sensor 58 may be used to determine the local activation time of segment 56, as an input to the controller, such as for timing the electrification of the electrodes. Other additional or alternative local and/or global cardiac parameters may also be used for determining the electrification of the electrodes. For example, the electrode(s) may be used to sense the local electrical activity, as well known in the art. Alternatively, sensor 58 is located near the SA node for determining the start of the cardiac rhythm. Alternatively, sensor 58 is used to sense the mechanical activity of segment 56, of other segments of the heart or for sensing the cardiac output. Cardiac output may be determined using a pressure sensor or a flow meter implanted in the aorta. In preferred embodiment of the invention, sensor 58 senses the electrical state of the heart, controller 50 determines a state of fibrillation and electrifies electrodes 52 and 54 accordingly.

Sensor 58 may be used for precise timing of the electrification of electrodes 52 and 54. One danger of incorrect electrification of the electrodes is that if the electrodes are electrified before an activation front reaches segment 56, the electrification may induce fibrillation. In a preferred embodiment of the invention, sensor 58 is placed between electrodes 52 and 54 so that an average activation time of tissue at the two electrodes is sensed. It should be appreciated that the precise timing of the electrification depends on the propagation direction of the activation front in the heart. Thus, if tissues at electrodes 52 and 54 are activated substantially simultaneously, the controlling field can be timed to be applied shortly thereafter. However, if tissue at one electrode is activated before tissue at the other electrode, the delay time in electrifying the electrodes must be longer. Thus, the optimal delay time in electrifying an electrode after the local activation time is dependent, among other things, on the orientation of the electrodes relative to the activation front. The conduction velocity of the activation front is affected in a substantial manner by the orientation of the cardiac muscle fibers. Thus, the orientation of the electrodes relative to the muscle fiber direction also has an effect on the optimal delay time.

In another preferred embodiment of the invention, local activation time (and electrification of electrodes 52 and 54) is estimated, based on a known propagation time of the activation signal. For example, if sensor 58 is placed in the right atrium, a delay of about 120 msec may be expected between the sensing of an activation signal at sensor 58 and the arrival of the activation signal at electrodes 52 and 54. Such delays can also be estimated. Within a single chamber, for example, it takes about 30–50 msec for the activation front to cover all the left ventricle. A sensor 58 may be placed at a location in the left ventricle which is excited relatively early by the activation signal. In a preferred embodiment of the invention, activation propagation times between implanted sensors and electrodes are measured in at least one heart activation profile (such as at a resting heart rate) and are used to estimate a desired delay in electrification of electrodes. It should be appreciated that, in diseased hearts, local conduction velocity may change substantially in time, thus, learning of and adaptation to the changes in local activation are a desirable characteristic of controller 50. In a preferred embodiment of the invention, a particular state of arrhythmia (or activation profile) is determined based on a parameter of the ECG, such as the morphology and/or the frequency spectrum of either an external of an internal ECG. Controller 50 determines the controlling profile based on the determined state. In particular, delay times, as described herein, may be associated with states, so that the exact delay time for the activation may be decided in real-time for each state of arrhythmia. Preferably, the delay times are precalculated and/or are determined during a learning state of controller 50, in which stage, an optimal delay time is determined for a particular activation state and stored in association therewith.

Sensor 58 may be placed on the epicardium, on the endocardium or, in a preferred embodiment of the invention, sensor 58 is inserted into the myocardium.

Figure 4B:
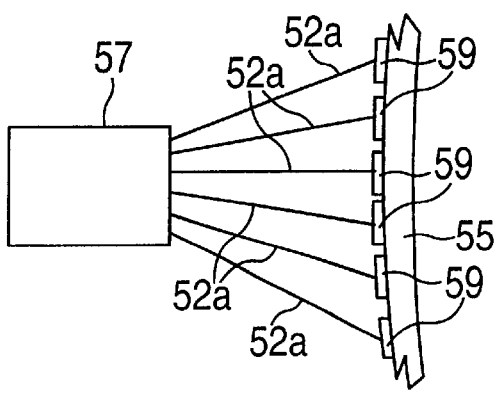
FIG. 4B is a schematic diagram of an electrical controller connected to a segment of cardiac muscle, in accordance with a preferred embodiment of the invention.

FIG. 4B shows an alternative embodiment of the invention, wherein a heart segment 55 is controlled by a plurality of electrodes 59 which are connected to a controller 57. The use of many electrodes enables greater control of both spatial and temporal characteristics of the applied electric field. In one example, each one of electrodes 59 is used to determine its local activation. Controller 57 individually electrifies electrodes 59 according to the determined activation. Preferably, the electrodes are activated in pairs, with current flowing between a pair of electrodes whose local activation time is known.

An implantable light source 57 (FIG. 4B) can be used instead of the electrical controller, which generates pulses of light that are transmitted to at least one light source(s) 59 adjacent to a site of the heart, through waveguides 52a. Similarly, when radio frequency is employed to irradiate the heart of a portion thereof, the radio transmitter 59 replaces the electrical controller.

Different embodiments of the present invention will typically require different placement of the control electrodes. For example, some embodiments require a large area electrode, for applying an electric field to a large portion of the heart. In this case, a net type electrode may be suitable. Alternatively, a large flat electrode may be placed against the outside of the heart. Other embodiments require long electrodes, for example, for generating fences. In this case, wires are preferably implanted in the heart, parallel to the wall of the heart. Optionally, the electrodes may be placed in the coronary vessels outside the heart. In some aspects of the invention electrodes are placed so that the field generated between the electrodes is parallel to the direction in which activation fronts normally propagate in the heart, in others, the field is perpendicular to such pathways.

In one preferred embodiment of the invention, a pacemaker is provided which increases the cardiac output. A pacemaker activation pulse is usually a single pulse of a given duration, about 2 msec in an internal pacemaker and about 40 msec in an external pacemaker. In accordance with a preferred embodiment of the invention, a pacemaker generates a double pulse to excite the heart. A first portion of the pulse may be a stimulation pulse as known in the art, for example, 2 mA (milliamperes) constant current for 2 msec. A second portion of the pulse is a pulse as described herein, for example, several tens of msec long and at a short delay after the first portion of the pacemaker pulse. Alternatively, a very long stimulation pulse may be used. This type of pacemaker preferably uses two unipolar electrodes, one at the apex of the heart and one at the top of the left ventricle (or the right ventricle if it the right ventricular activity is to be increased).

In a preferred embodiment of the invention, a controller is implanted into a patient in which a pacemaker is already implanted. The controller is preferably synchronized to the pacemaker by connecting leads from the controller to the pacemaker, by sensors of the controller which sense the electrification of the pacemaker electrodes and/or by programming of the controller and/or the pacemaker.

In a preferred embodiment of the invention, the pacemaker adapts to the physiological state of the body in which it is installed by changing the heart's activity responsive to the physiological state. The pacemaker can sense the state of the body using one or more of a variety of physiological sensors which are known in the art, including, pH sensors, $pO_2$ sensors, $pCO_2$ sensors, blood-flow sensors, acceleration sensors, respiration sensors and pressure sensors. For example, the pacemaker can increase the flow from the heart in response to an increase in $pCO_2$. Since the control is usually applied in a discrete manner over a series of cardiac cycles, this control may be termed a control sequence. The modification in the heart's activity may be applied gradually or, preferably, in accordance with a predetermined control sequence.

In one aspect of the invention, target values are set for at least one of the measured physiological variables and the pacemaker monitors these variables and the effect of the control sequence applied by the pacemaker to determine a future control sequence. Once the discrepancy between the target value and the measured value is low enough, the control sequence may be terminated. As can be appreciated, one advantage of a cardiac controller over a pacemaker is that it can control many aspect of the heart's activation profile. As a result, the controller can determine a proper tradeoff between several different aspects of the activation profile of the heart, including, heart output, oxygenation of the cardiac muscle, contractile force of the heart and heart rate.

Another aspect of the invention relates to modifying the relation between the contraction of the left ventricle and the contraction of the right ventricle. In a healthy heart, increased contractility of the left ventricle is followed by increased contractility of the right ventricle, as a result of the increased output of the left ventricle, which causes an increase in the preload of the right ventricle. Decreased left ventricular output reduces the right ventricular output in a similar manner. In some cases, such as pulmonary edema, it may be desirable to modify the flow from one ventricle without a corresponding change in the flow from the other ventricle. This may be achieved by simultaneously controlling both ventricles, one control increasing the flow from one ventricle while the other control decreases the flow from the other ventricle. This modification will usually be practiced for short periods of time only, since the vascular system is a closed system and, in the long run, the flow in the pulmonary system is the same as in the general system. In a preferred embodiment of the invention, this modification is practiced by controlling the heart for a few beats, every certain period of time.

Another aspect of the present invention relates to performing a complete suite of therapies using a single device. A controller in accordance with a preferred embodiment of the invention includes several therapies which it can apply to the heart, including for example, increasing contractility, defibrillation, fencing, heart rate control and pacing. The controller senses (using physiological sensors) the state of the body and decides on an appropriate short-term therapy, for example, defibrillation to overcome fibrillation, increasing the heart rate to increase the cardiac outflow or applying fences to restrain a sudden arrhythmia. Additionally or alternatively, such a controller can change the applied control sequence in response to long term therapeutic goals. For example, if increasing contractility is used to increase the muscle mass in a portion of the heart, once a required muscle mass is reached, the control sequence may be stopped. This is an example of a therapeutic treatment affected by the controller. In another example, a few weeks after the device is implanted and programmed to increase the cardiac output to a certain target variable, the target variable may be changed. Such a change may be mandated by an expected period of time over which the heart adapts to the controller. One such adaptation is that the heart becomes stronger and/or more efficient. Another such adaptation may be that the heart reduces its response to the control sequence, so that a different control sequence may be required to achieve the same goals. In a preferred embodiment of the invention, the control sequence is varied every certain period of time and/or when the response of the heart to the control sequence is reduced below a predetermined level.

In an alternative embodiment of the invention, a control device includes a human operator in the loop, at least during a first stage where the controller must "learn" the distinctive aspects of a particular heart/patient. At a later stage, the operator may monitor the therapeutic effect of the controller on a periodic basis and change the programming of the controller if the therapeutic effect is not that which the operator desires.

In an additional embodiment of the invention, the controller is not implanted in the body. Preferably, the control sequence is applied using one or more catheters which are inserted into the vascular system. Alternatively, electrodes may be inserted directly through the chest wall to the heart.

In another preferred embodiment of the invention, a controlling current (or electric field) is applied from electrodes external to the body. One inherent problem in external controlling is that the controlling current will usually electrify a large portion of the heart. It therefore important to delay the application of the current until the heart is refractory. One method of achieving this objective is to sense the ECG using external electrodes. Preferably, an electrode array is used so that a local activation time in predetermined portions of the heart may be determined.

Another method of external controlling combines controlling with external pacing, thereby simplifying the task of properly timing the controlling pulse relative to the pacing pulse. In a preferred embodiment of the invention, the delay between the pacing pulse and the controlling pulse is initially long and is reduced until an optimum delay is determined which gives a desired improvement in pumping and does not cause fibrillation.

Additionally or alternatively, the external pacemaker includes a defibrillator which applies a defibrillation pulse if the controlling pulse causes fibrillation.

It should be appreciated that pacemakers and controllers in accordance with various embodiments of the present invention share many common characteristics. It is anticipated that combining the functions of a controller and of a pacemaker in a single device will have many useful applications. However, several structural differences between pacemakers, defibrillators and controllers in accordance with many embodiments of the present invention are notable.

One structural difference relates to the size and shape of the electrodes. Pacemakers usually use bipolar activation electrodes or unipolar electrodes where the pacemaker case is the other electrode. The design of the electrodes is optimized to enhance the contact between the electrodes and the heart at a small area, so that the power drain in the pacemaker will be as low as possible. In a defibrillator, there is an opposite consideration, namely, the need to apply a very large amount of power to large areas of the heart without causing damage to the heart. In preferred embodiment of the present invention, small currents are applied, however, it is desirable that the current flow through large portions of the cardiac tissue, in a controlled manner.

Another structural difference relates to the power supply. Pacemaker power supplies usually need to deliver a short (2 msec), low power, pulse once a second. Defibrillators usually need to deliver a short (6–8 msec), high power, pulse or series of pulses at long intervals (days). Thus, pacemakers, usually drain the power from a capacitor having a short delay and which is directly connected to the battery, while defibrillators usually charge up both a first and a second capacitor so that they may deliver two sequential high-power pulses. A controller in accordance with some embodiments of the present invention, is required to provide a long low power pulse once a second. Preferably, the pulse is longer than 20 msec, more preferably longer than 40 msec and still more preferably, longer than 70 msec. Such a pulse is preferably achieved using a slow-decay capacitor and/or draining the power directly from a battery, via an constant current, a constant voltage and/or a signal forming circuit. Preferably, the electrodes used in a controller in accordance with the present invention slowly release a steroid, to reduce inflammation at the electrodes point of contact with the heart.

Another structural difference relates to the placement of the electrodes. In a pacemaker, a single electrode is placed in the apex of the heart (in some pacemakers, one electrode per chamber, or sometimes, more than one). In a defibrillator, the electrodes are usually placed so that most of the heart (or the right atrium in AF defibrillators) is between the electrodes. In a controller according to some embodiments of the present invention, the electrodes are placed across a segment of heart tissue, whose control is desired. Regarding sensing, many pacemakers utilize sensing in one chamber to determine a proper delay before electrifying a second chamber. For example, in a heart whose AV node is ablated, the left ventricle is synchronized to the right atrium by a pacemaker which senses an activation front in the right atrium and then, after a suitable delay, paces the left ventricle. It is not, however, a usual practice to sense the activation front in a chamber and then pace the selfsame changer after a delay. Even when such same chamber sensing and pacing is performed, the sensing and pacing are performed in the right atrium and not the left ventricle. Further, sensing at the pacing electrode in order to determine a delay time for electrification of the electrode is a unique aspect of some aspects of the present invention, as is sensing midway between two pacing electrodes. Another unique aspect of some embodiments of the present invention is pacing in one chamber (the right atrium), sensing an effect of the pacing in another chamber (the left ventricle) and then pacing the other chamber (the left ventricle). The use of multiple pairs of electrodes disposed in an array is another unique aspect of certain embodiments of the present invention.

Due to the wide range of possible signal forms for a controller, a preferred controller is programmable, with the pulse form being externally downloadable from a programmer. Telemetry systems for one- and two-directional communication between an implanted pacemaker and an external programmer are well known in the art. It should be noted, that various embodiments of the present invention can be practiced, albeit probably less efficiently, by downloading a pulse form in accordance with the present invention to a programmable pacemaker. In a preferred embodiment of the invention, such a programmer includes software for analyzing the performance and effect of the controller. Since analysis of the performance of the controller may include information not provided by the controller, such as an ultrasound image or an external body ECG, such software may be run from a separate computer.

It should be appreciated that a controller in accordance with the present invention is preferably personalized for particular patient before implantation therein. Alternatively or additionally, the personalizations may be performed by programming the device after it is implanted. The heart of the patient is preferably mapped, as described above, in order to determine the preferred placement of the control electrodes and/or the sensing electrodes and/or in order to determine the proper timings.

In one example, where the left ventricle is controlled, it is useful to determine the earliest activated area in the left ventricle, for implantation of the sensing electrode. In another example, the heart is mapped to determine viable tissue portions which are suitable for implantation of electrodes (such that current will flow between the two electrodes). In another example, the activation profile of the heart is determined so that it is possible to estimate propagation times between various portions of the heart, and in particular, the pacing source (natural or artificial) and the controlling electrodes. In another example, the propagation of the activation front in the heart is determined so that the proper orientation of the electrodes with respect to the front may be achieved and/or to properly locate the sensing electrode(s) with respect to the controlling electrodes. It is also useful to determine arrhythmias in the heart so as to plan anti-arrhythmic treatment in accordance with the present invention.

In another example, the amount of increase in contractility is determined by the amount of live tissue between the controlling electrodes. A viability map may be used to determine a segment of heart tissue having a desired mount of live tissue.

The timing of the activation of cardiac muscle relative to the rest of the heart is an important factor in determining its contribution to the cardiac output. Thus, it is useful to determine the relative activation time of the segment of the heart which is to be controlled, prior to implanting the electrodes.

Figure 5:
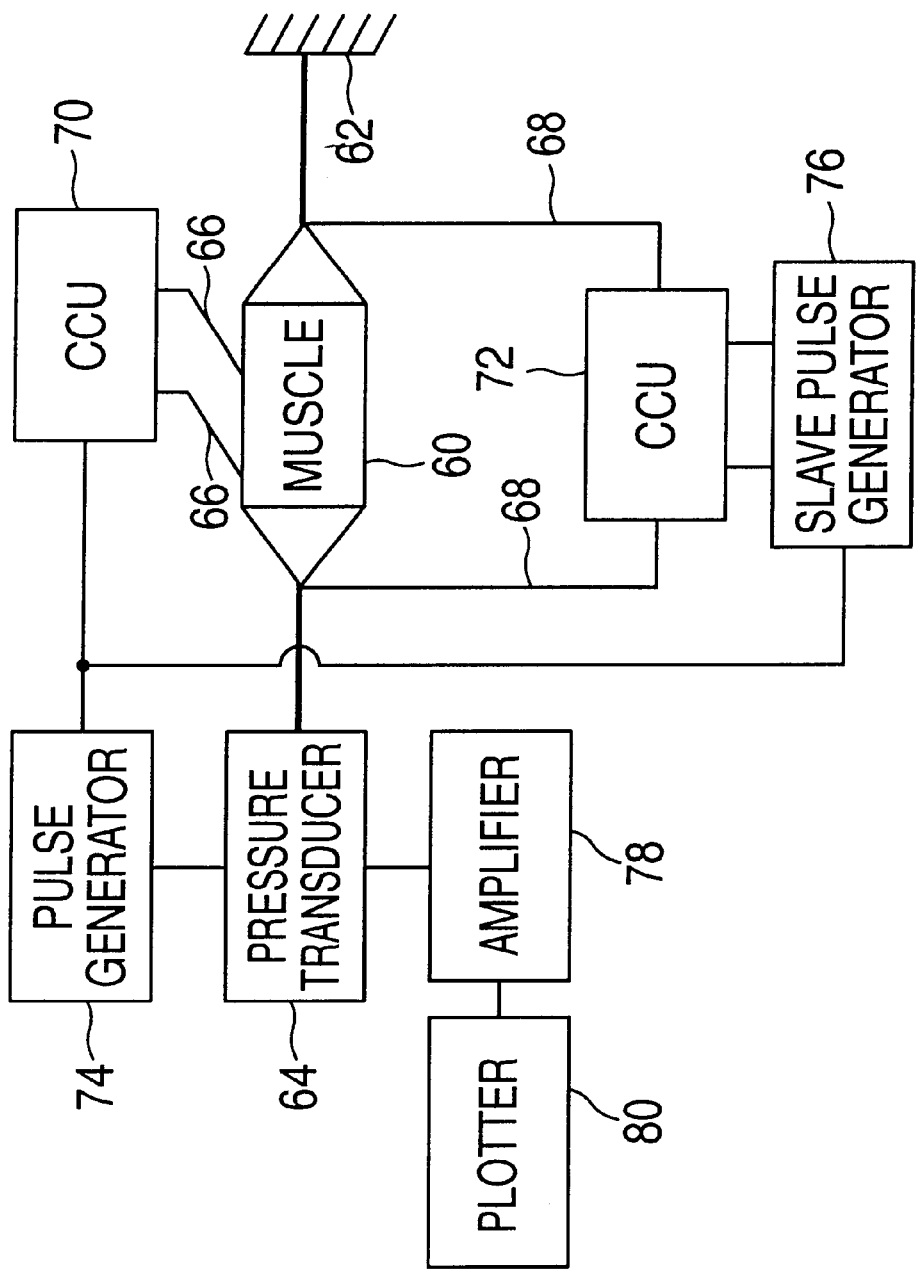
FIG. 5 is a schematic diagram of an experimental setup used for testing the feasibility of some embodiments of the present invention.

FIG. 5 shows an experimental setup designed and used to test some embodiments of the present invention. A papillary muscle 60, from a mammalian species (in the first set of experiment, a guinea pig), was connected between a support 62 and a pressure transducer 64 in a manner such that isometric contraction could be achieved. Muscle 60 was stimulated by a pair of electrodes 66 which were connected to a pulsed constant current source 70. A pulse generator 74 generated constant current pacing pulses for electrodes 66. A pair of electrodes 68 were used to apply an electric field to muscle 60. A slave pulse generator 76, which bases its timing on pulse generator 74, electrified electrodes 68 via a pulsed constant current source 72. The force applied by the muscle was measured by transducer 64, amplified by an amplifier 78 and drawn on a plotter 80. Pulse generator 74 selectably generated short activation pulses 500, 750, 1000 and 1500 msec (t1) apart for variable activation of muscle 60, i.e., 2, 1.33, 1 and 0.66 Hz. Pulse generator 76 generated a square wave pulse which started t2 seconds after the activation pulse, was t3 seconds long and had a selected current (in mA) higher than zero (in amplitude).

Figure 6A:
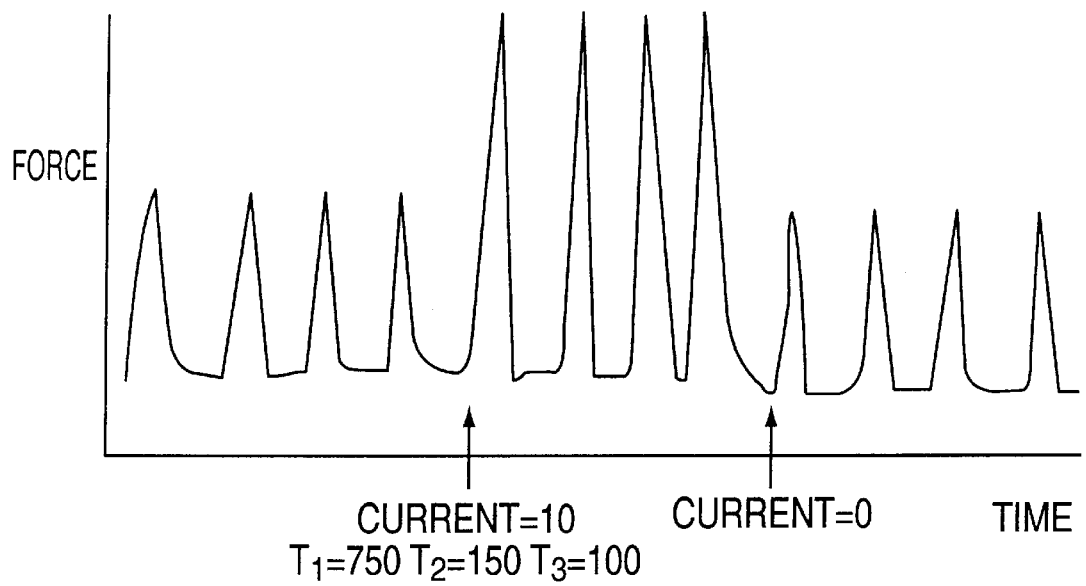
FIGS. 6A–6C are graphs showing the results of various experiments.
Figure 6B:
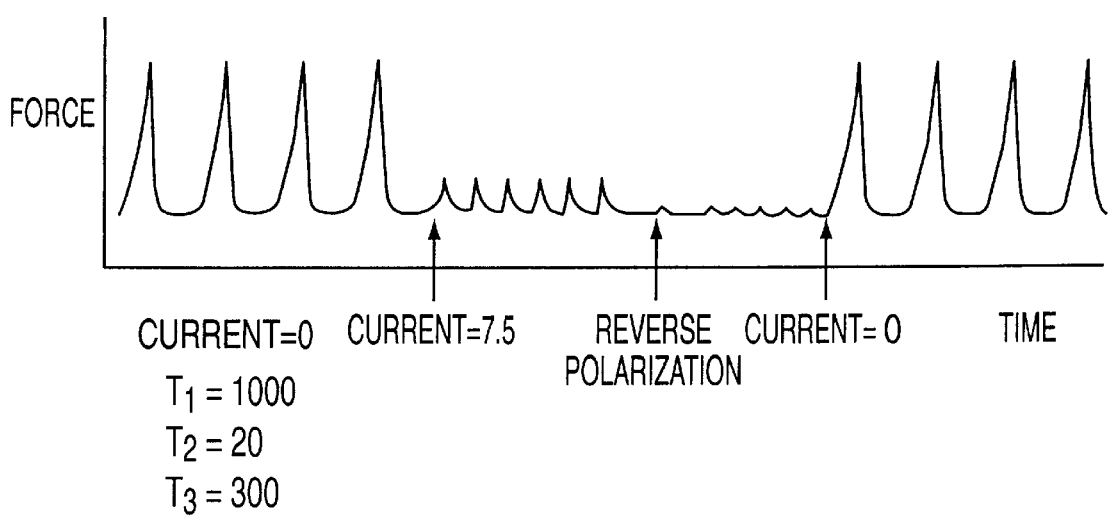
Figure 6C:
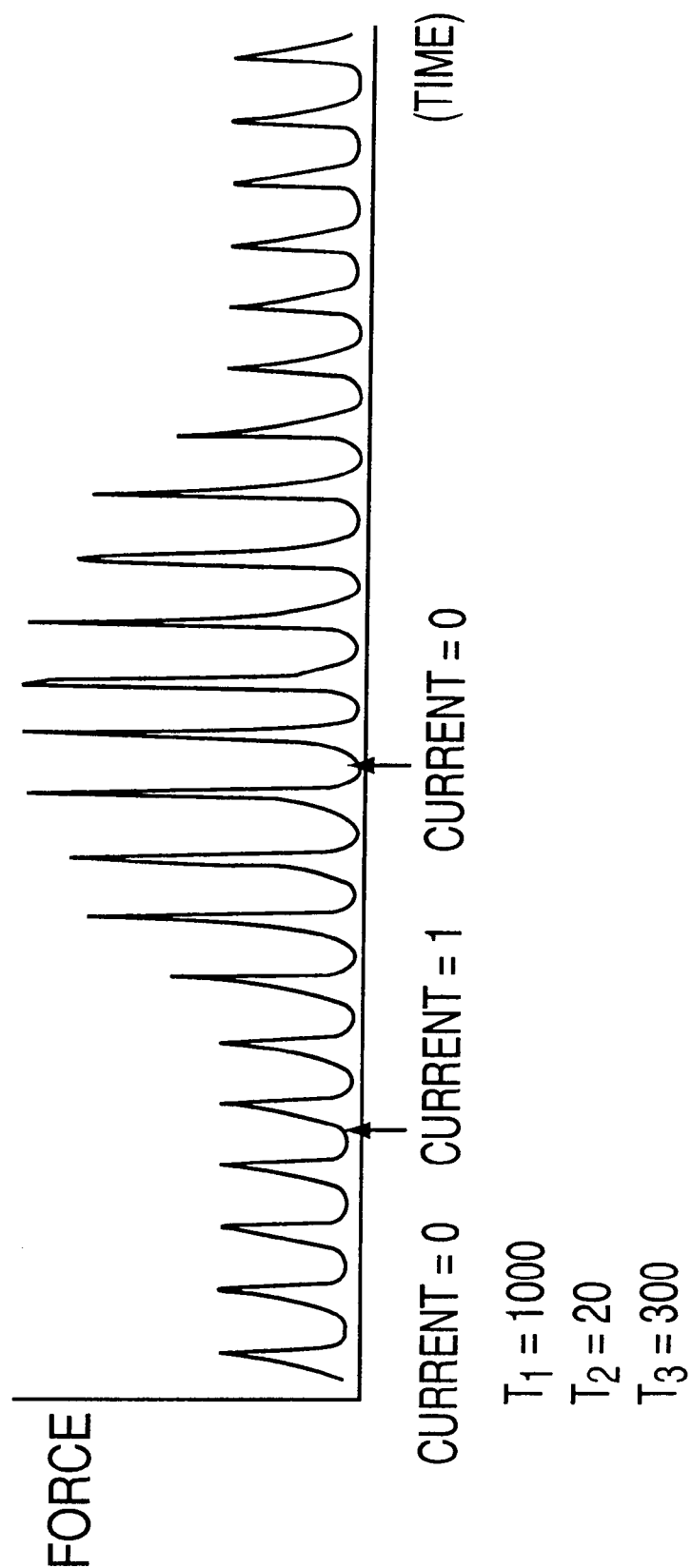

FIGS. 6A–6C are graphs showing some results of the experiments. In general, the results shown are graphs of the force of the muscle contractions after muscle 60 reaches a steady state of pulsed contractions. FIG. 6A is a graph of the results under the following conditions:

t1 (pacemaker pulse)=750 msec;

t2 (delay)=150 msec;

t3 (pulse duration)=100 msec; and current=10 mA.

As can be seen, the force exerted by the muscle was increased by a factor of 2.5 when the controlling pulse (electrodes 68) was used as opposed to when electrodes 68 were not activated.

FIG. 6B is a graph of the force of muscle contractions under the following conditions:

t1=1000 msec;

t2=20 msec;

t3=300 msec; and current=7.5 mA.

As can be seen, the amplitude of the contractions is extremely attenuated. When the polarity of the controlling signal was inverted, after a few contractions, the contractions of muscle 60 were almost completely attenuated.

FIG. 6C is a graph of the force of muscle contractions under the following conditions:

t1=1000 msec;

t2=20 msec;

t3=300 msec; and current=1 mA.

In this case, the effects of increasing the contractile of muscle 60 remained for about two minutes after the electrification of electrodes 68 was stopped. Thus, the contraction of muscle 60 is dependent not only on the instantaneous stimulation and control but also on prior stimulation and control.

Using a similar experimental setup, additional experiments were performed, some on papillary muscles and some on cardiac septum muscles from the ventricles and atria walls. In these experiments, the test animal was usually a rabbit, however, in one case a rat was used. Most of these experiments used a DC constant current source which was in contact with the muscle, however, an electrical field scheme was also tested, and yielded similar results. In the electric field scheme, the electrodes were placed in a solution surrounding the muscle segment and were not in contact with the muscle segment. The current used was 2–10 mA. In a few experiments, no increase in contractile force was induced, however, this may be the result of problems with the electrodes (interaction with ionic fluids) and/or the current source, especially since Ag—AgCl electrodes, which tend to polarize, were used in these experiments. In general, many cycles of increases in contractility and return to a base line were performed in each experiment. In addition, the increases in contractility were repeatable in subsequent experiments. These increases were obtained over a pacing range of 0.5–3 Hz.

Figure 7A:
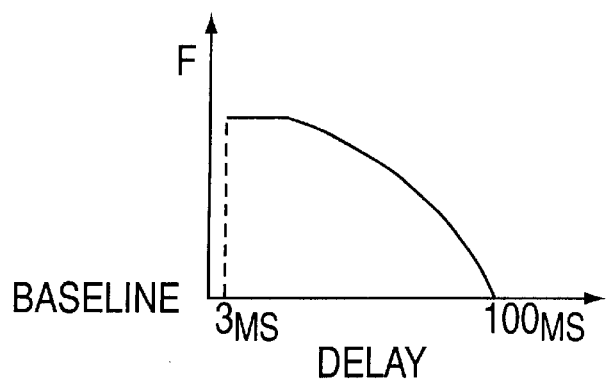
FIG. 7A is a graph summarizing results of experimentation on an isolated segment of cardiac muscle fibers, and showing the effect of a delay in applying a pulse in accordance with an embodiment of the invention, on the increase in contractile force.
Figure 7B:
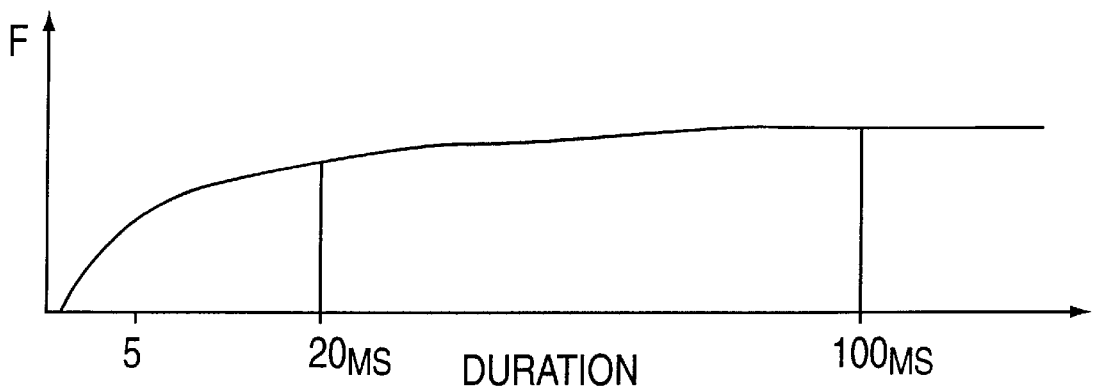
FIG. 7B is a graph summarizing results of experimentation on an isolated segment of cardiac muscle fibers, and showing the effect of a duration of the pulse on the increase in contractile force.
Figure 7C:
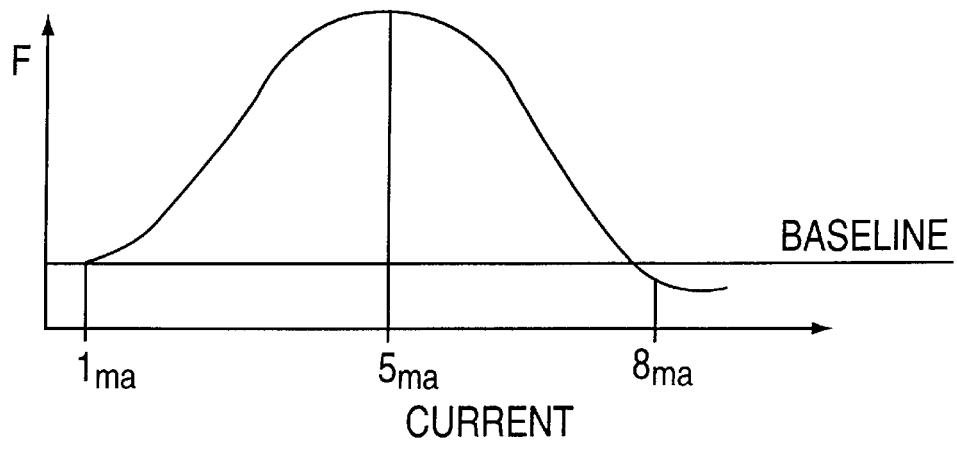
FIG. 7C is a graph summarizing results of experimentation on an isolated segment of cardiac muscle fibers, and showing the effect of a current intensity of the pulse on the increase in contractile force.

FIGS. 7A–7C summarize the results obtained in these further experiments. It should be appreciated, that the time scales of the applied pulse are strongly associated with the pacing rate and with the animal species on which the experiment was performed. In these experiments, the pacing rate was usually about 1 Hz. Within the range of 0.5–3 Hz the pulse form required for an increase in contraction force is not substantially affected by the pacing rate. The intensities of the currents used in the experiments are affected by the electrode types used, and possibly by the animal species, so that if other electrode types are used, different current intensities may be required for the same effect. Ten experiments were performed on a left papillary muscle, of which 8 showed an increase in contractility due to an applied non-excitatory current. Four experiments were performed on a right papillary muscle, of which three showed an increase in contractility. Two experiment were performed on left ventricular muscle, both showing an increase in contractility. On the average, an increase in contractile force of ~75% was obtained. The range of increases was between 43% and 228% depending on the exact experimental configuration.

FIG. 7A shows the effect of a delay in the onset of the applied current on the increase in contractile force. A small delay does not substantially affect the increase in contractile force. It should be noted that as the delay increases in duration, the increase in contractility is reduced. It is theorized that such a pulse, applied at any delay, affects the plateau and/or the refractory period. However, the increase in contractility is only possible for a window of time which is more limited than the entire activation cycle of a muscle fiber.

Changing the polarity of the applied current sometimes affected the contractility. Usually, a first polarity generated an greater increase in contractile force, while the other polarity generated a lower increase than the first polarity. In some experiments, reversing the polarity during an experiment decreased the contractile force, for a short while or for the entire duration of the pulse, to a level lower than without any applied current. One possible explanation is that papillary muscle has a preferred conduction direction (which may not be as pronounced in ventricular tissue). Another explanation is artifacts relating to the ionization of the electrodes used in the experiments.

FIG. 7B shows the effect of pulse duration on the increase in contractile force of a papillary muscle. A very short pulse, on the order of 1 msec, does not substantially affect the contractile force. In a pulse between about 1 msec and 20 msec the contractility increases with the duration. In a pulse of over 20 msec, the increase in contractile force as a function of pulse duration is reduced; and in a pulse with over about 100 msec duration there is no apparent further increase in the contractile force of an isolated papilary muscle.

FIG. 7C shows the effect of the current intensity on the increase in contractile force. It should be noted that above about 8 mA the contractile force actually decreases below the baseline condition (where no current was applied). It may be that this effect is related to the above described theory of intra-cellular calcium stores, and that too much calcium in the cardiac muscle cell reduces the availability of these stores, and therefore, the cell's contractility.

In addition to the above summarized results, several experimental results deserve special notice.

Figure 8A:
FIG. 8A is a graph showing the effect of a controlling current on a heart rate, in accordance with a preferred embodiment of the invention.

In one experiment, shown in FIG. 8A, a segment of a right atrium from a rabbit was allowed to set its own, intrinsic, pace (~2–3 Hz). A non-excitatory current which was a constant current of 2 mA was driven through the tissue, constantly, as shown. As a result, the self pacing rate of the segment increased, as did the contractility (after a first, short, reduction in force).

In a second, multi-step experiment, a right rabbit papillary muscle was paced at 1.5 Hz. The applied current was constant at between 2 and 4 mA (depending on the experimental step), in a pulse 70 msec long and no delay after the pacemaker pulse. The contractility increased by between 45% and 133% (depending on the step). The increased contractility was sustained at 3 mA for as long as two hours. Stopping the applied field caused a rapid return to the original (uncontrolled) contractile force. Re-application of the field repeated the previous results.

In a third experiment, increasing the pulse duration of a 2 mA current over the range 10 to 100 msec in a left rabbit papillary muscle increased the contractile force; however, no effect on the duration of the muscle twitch was observed.

FIG. 8B is a series of graphs which shows an increase in contractility in several, different cardiac muscle types (the horizontal bar indicates the application of a controlling electric field).

Two more experiments, not included in the above discussion, were performed on a papillary muscle. In these experiments, a triangular shaped pulse, having a duration of 120 msec and a peak of 5 mA, was applied with no delay after a standard pacing pulse (2 mA, 2 msec). The increase in contractility of the muscle was ~1700%, from 10 mg to 178 mg. The duration of the contraction increased from 220 msec to 260 msec.

In another series of experiments, a whole living heart was removed from a rabbit (1–2 Kg in weight) and controlled using methods as described hereinabove. The apparatus for keeping the heart alive was an Isolated Heart, size 5, type 833, manufactured by Hugo Sachs Elektronik, Gruenstrasse 1, D-79232, March-Hugstetten, Germany. In these experiments, only the left ventricle is functional. The Pulmonary veins are connected to a supply hose, in which supply hose there is a warm (~37° C.) isotonic, pH balanced and oxygenated solution. The solution is pumped by the heart into the aorta. The heart itself is supplied with oxygen from the aorta, through the coronary arteries. The coronary veins empty into the right ventricle, from which the solution drips out. The solution which drips out (coronary blood flow) can be measured by collecting it in a measuring cup. Both the preload and the afterload of the vascular system can be simulated and preset to any desirable value. In addition, the afterload and preload can be measured using this apparatus.

The heart was connected to an ECG monitor, a pacemaker and a programmable pulse generator. The electrodes for applied the field typically had an area of between 2 and 3 $cm^2$. The left ventricular pressure (LVP) was measured using a pressure probe inserted into the ventricle. The flow through the aorta was measured using an electro-magnetic flowmeter. Various parameters, such as pH, $pO_2$, $pCO_2$ and temperature may be measured by attaching additional measurement devices. All the measurement devices may be connected to a computer which collects, and preferably analyzes the results.

A most notable experimental result was an increase in flow from the heart as a result of electrical control. Another notable result was an increase in afterload as a result of the control. Still another notable result was an increase in the developed left ventricular pressure, in the heart, when electrical control was applied.

A summary of 26 experiments using an isolated heart is as follows, in 20 experiments an increase in cardiac output was observed, while in six experiments, no increase in cardiac output was observed. Possible reasons for the failure to increase cardiac output include, biological damage to the heart while it was being extracted from the animal. In some cases, this damage is clear from the reduced cardiac output in one isolated heart as compared to a second, otherwise similar, rabbit heart. Other reasons include, incorrect placement of electrodes (over the right ventricle instead of over the left ventricle), encrustation of the electrodes with proteins and technical problems with the equipment which delivers the controlling electric field. In 11 experiments where the left ventricle was paced, the average increase in cardiac output was 17% with a standard deviation of 11%. In eight experiments where the right atrium was paced, the average increase was 9±4%. In nine experiments, where the heart was not paced and a controlling field was applied based on a sensing of local activation times, the increase was 7±2%. It should be noted that the number of experiments is over 26, since in some experiments two different pacing paradigms were tried.

Figure 9:
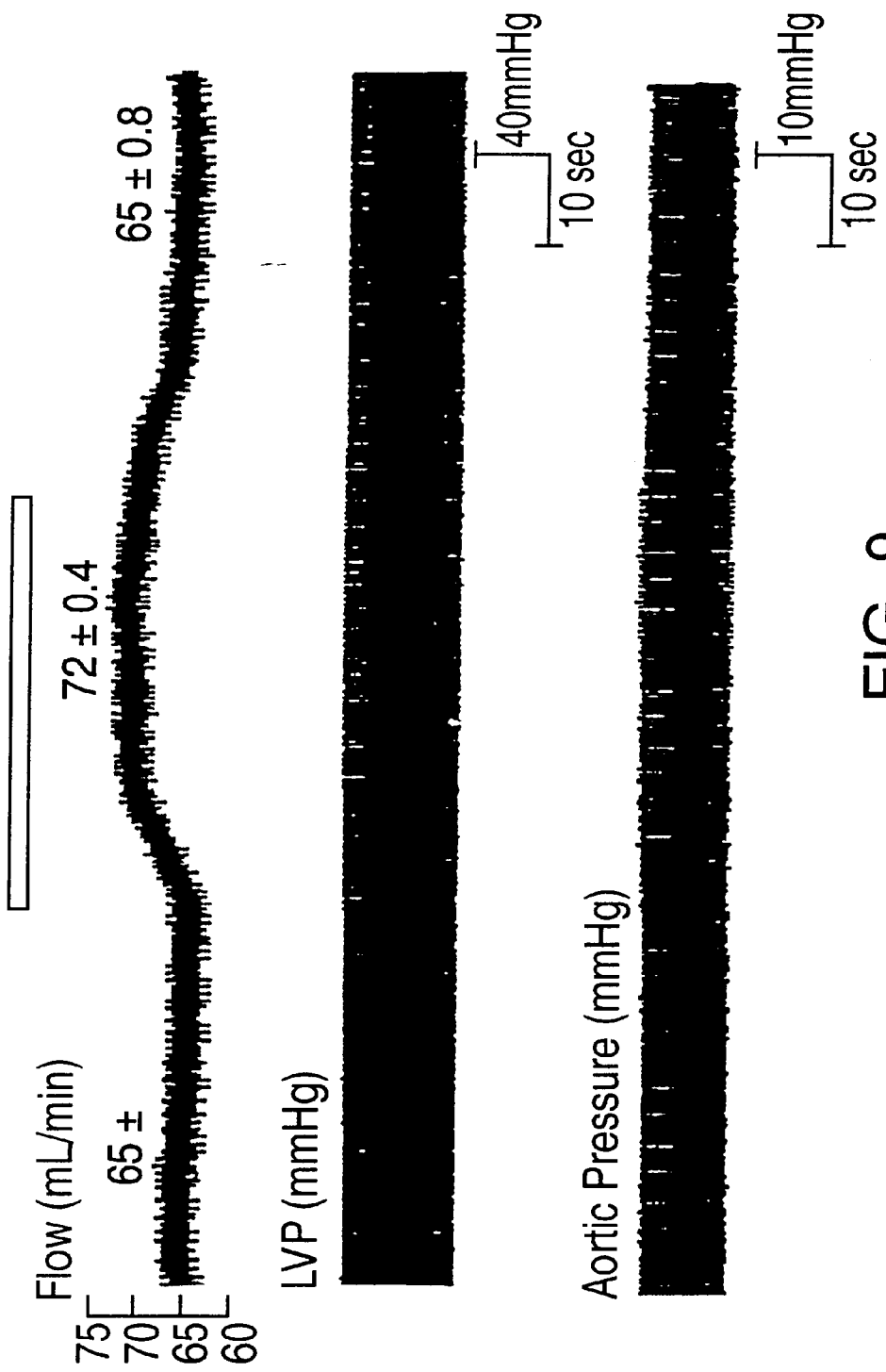
FIGS. 9–18B are each a series of graphs showing experimental results from experiments in which an isolated rabbit heart was controlled in accordance with an embodiment of the present invention.

FIG. 9 is a series of graphs showing the results of an experiment in which a 10 mA constant current pulse, having a duration of 20 msec and delayed 5 msec after the pacing of the heart, was applied. Two wire electrodes were used to apply this pulse, one electrode was placed at the apex of the heart overlaying the left ventricle and one electrode was placed at the base of the left ventricle. The pacing was performed using a bipolar electrode, also placed near the apex of the heart on the left ventricle. The pacing rate was approximately 10% higher than the normal pace. The pacing pulse was 2 msec long, 2 mA in amplitude and was applied at a frequency of ~3.5 Hz. The application of the constant current pulse is indicated in the Figure (and in the following ones) by a bar (filled or unfilled).

In this experiment, an increase in the afterload (the actual pressure developing in the Aorta) of about 5% and an increase in LVP (Left ventricle pressure) of about 3% were observed. The increase in LVP was only in the end systole pressure, not in the end diastole pressure. An increase in flow of about 11% is clearly shown in FIG. 9. The increase in flow is very important since one of the main problems with patients with congestive heart failure is a low cardiac flow.

Figure 10:
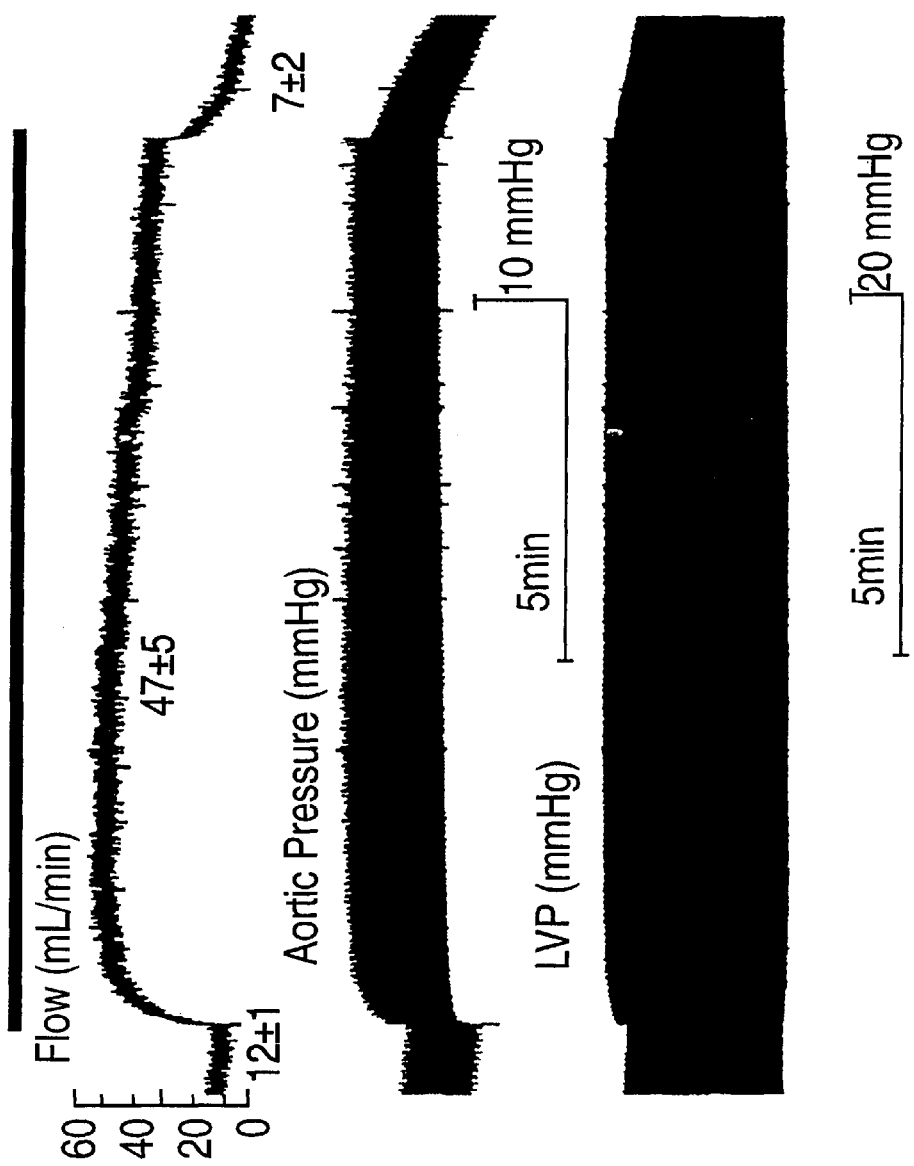

FIG. 10 is a series of graphs showing the results of an experiment in which a 5 mA constant current pulse, having a duration of 80 msec and delayed 2 msec after the pacing of the heart was applied. The wiring and pacing in this experiment were similar to the experiment described with reference to FIG. 9, except that carbon electrodes were used for applying the constant current pulse.

In this experiment, a noticeable increase in afterload can be determined from the graph. An increase in LVP (Left ventricle pressure) of about 6% can also be observed. It should be noted that the increase in afterload is observed for both the diastolic pressure and the systolic pressure, while inside the left ventricle, the pressure increase is mainly in the systole. In fact, there is a slight reduction in diastolic pressure, which may indicate an increase in contractility and/or an improvement in diastolic wall motion. An increase in flow of several hundred percent is clearly shown in FIG. 10. It should be noted that a healthy heart may be expected to have a flow of about 100 ml/min. The low initial flow (12 ml/min.) is probably a result of damage to the heart, such as ischemia.

Figure 11:
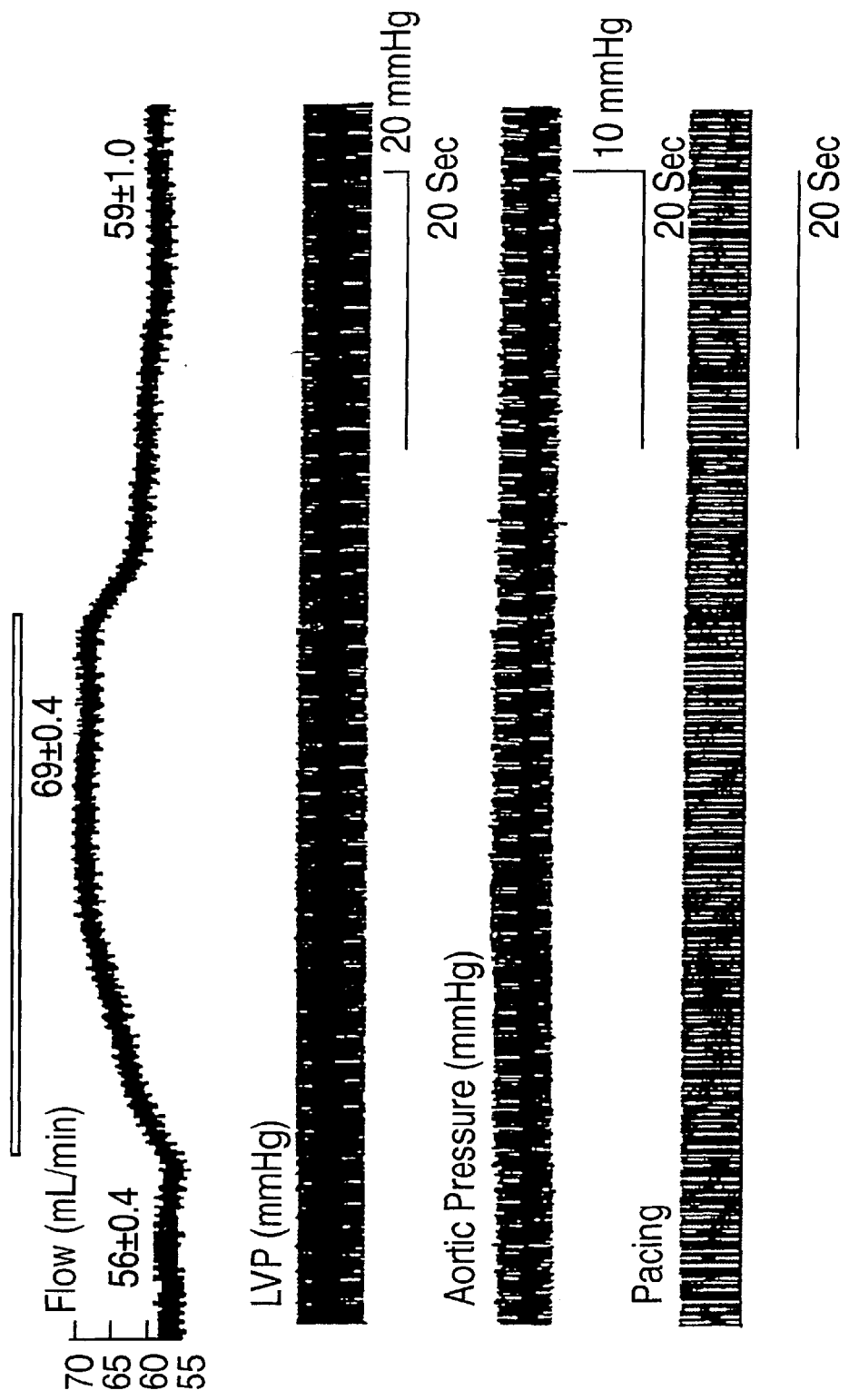

FIG. 11 is a series of graphs showing the results of an experiment in which a 5 mA constant current pulse, having a duration of 20 msec and delayed 2 msec after the local activation time at the ventricle was used. The pacing and wiring in this experiment were similar to the experiment described with reference to FIG. 9. A sensing electrode was placed on the left ventricle halfway between the two controlling electrodes and the delay was measured relative to the local activation time at the sensing electrode. The sensing electrode comprised two side by side "J" shaped iridium-platinum electrodes. The pacing pulse was applied using an additional Ag—AgCl electrode at the apex of the heart. In this experiment, the sensing electrode is shut off for 200 msec after the local activation is sensed, so that the controlling pulse is not erroneously detected by the sensing electrode as a local activation.

In this experiment, an increase in the afterload and an increase in LVP were observed. The increase LVP was only evident in the end systole pressure, not in the end diastole pressure. An increase in flow of about 23% is clearly shown in FIG. 11.

Figure 12:
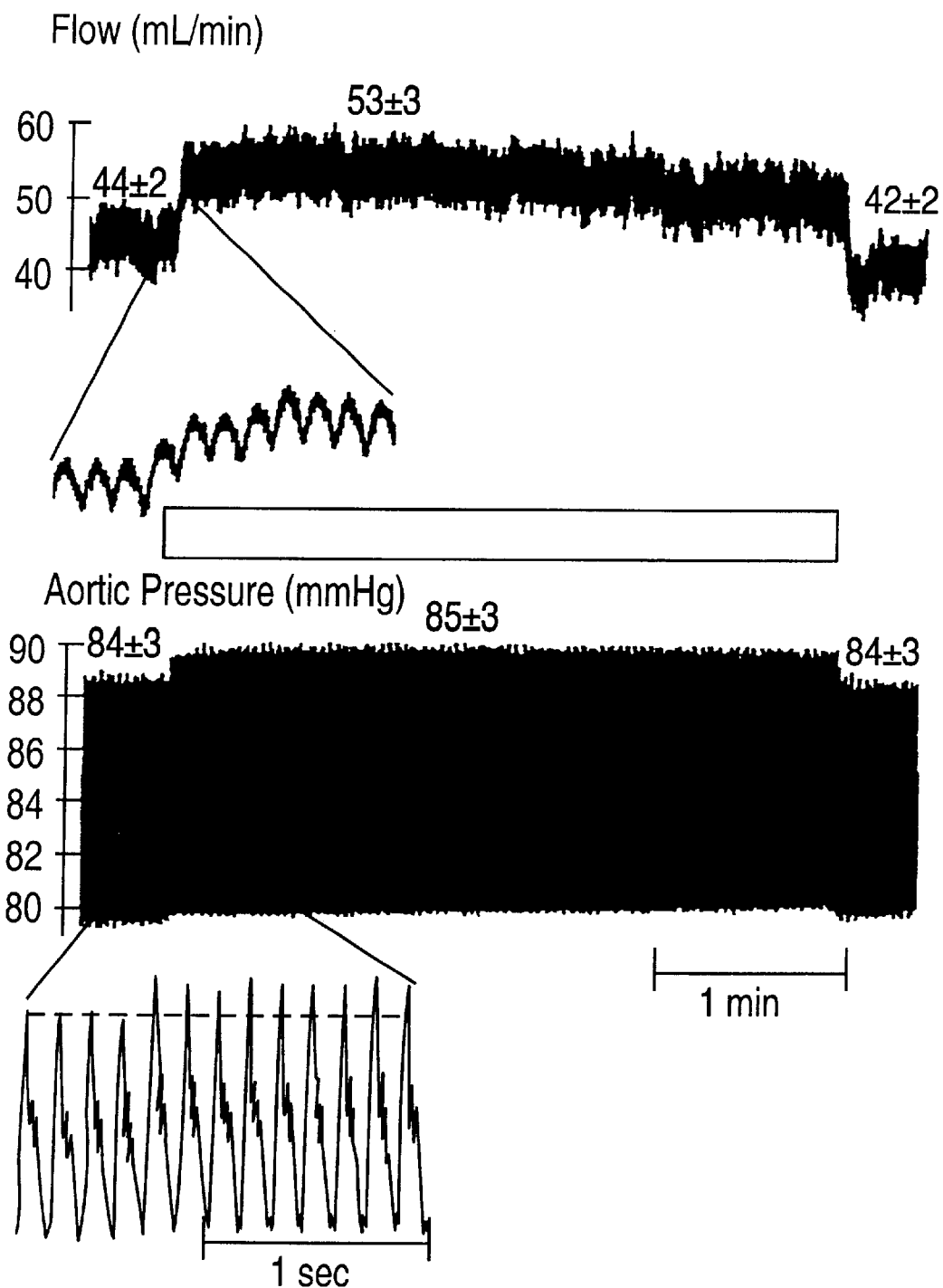

FIG. 12 is a series of graphs showing experimental results from another experiment, showing an significant increase in aortic flow and in aortic pressure. The pulse parameters were 5 mA, 70 msec duration and a 5 msec delay. Pacing and wiring are as in the experiment of FIG. 9.

Figure 13:
Figure 13:
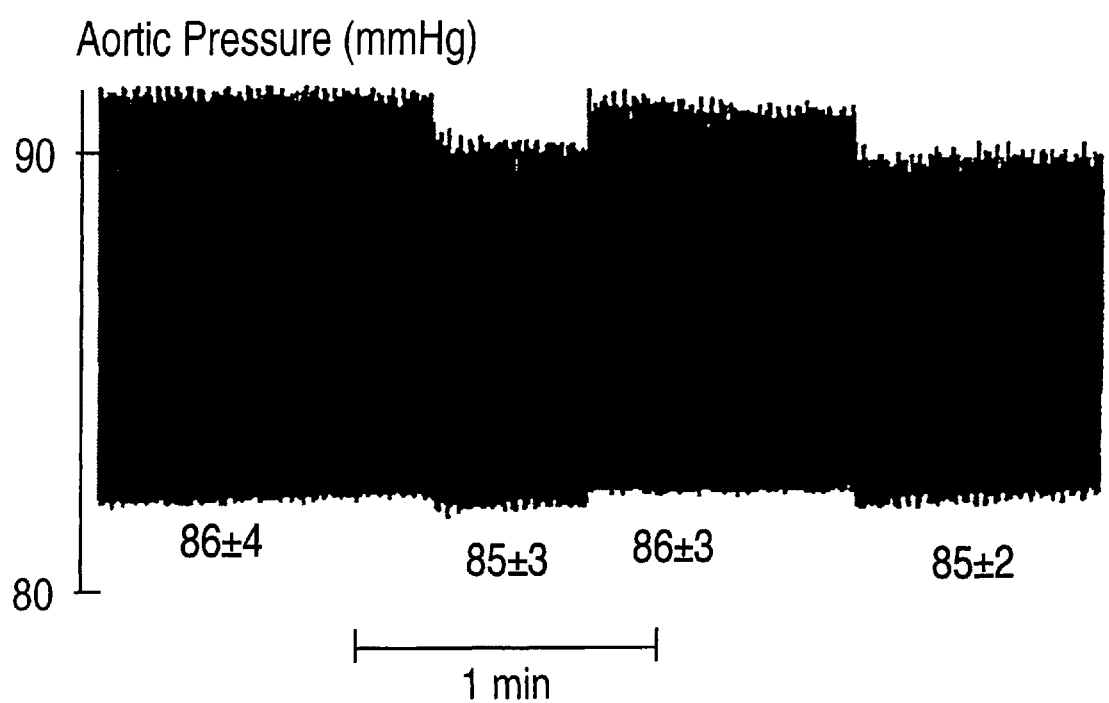

FIG. 13 is a series of graphs showing experimental results from repeating the experiment of FIG. 12, showing that the increase in aortic flow is controlled by the electrification of the electrodes. Thus, when the electrification is stopped, the flow returns to a baseline value; when the electrification is restarted the flow increases again and when the electrification is stopped again, the flow returns to the baseline value.

Figure 14:
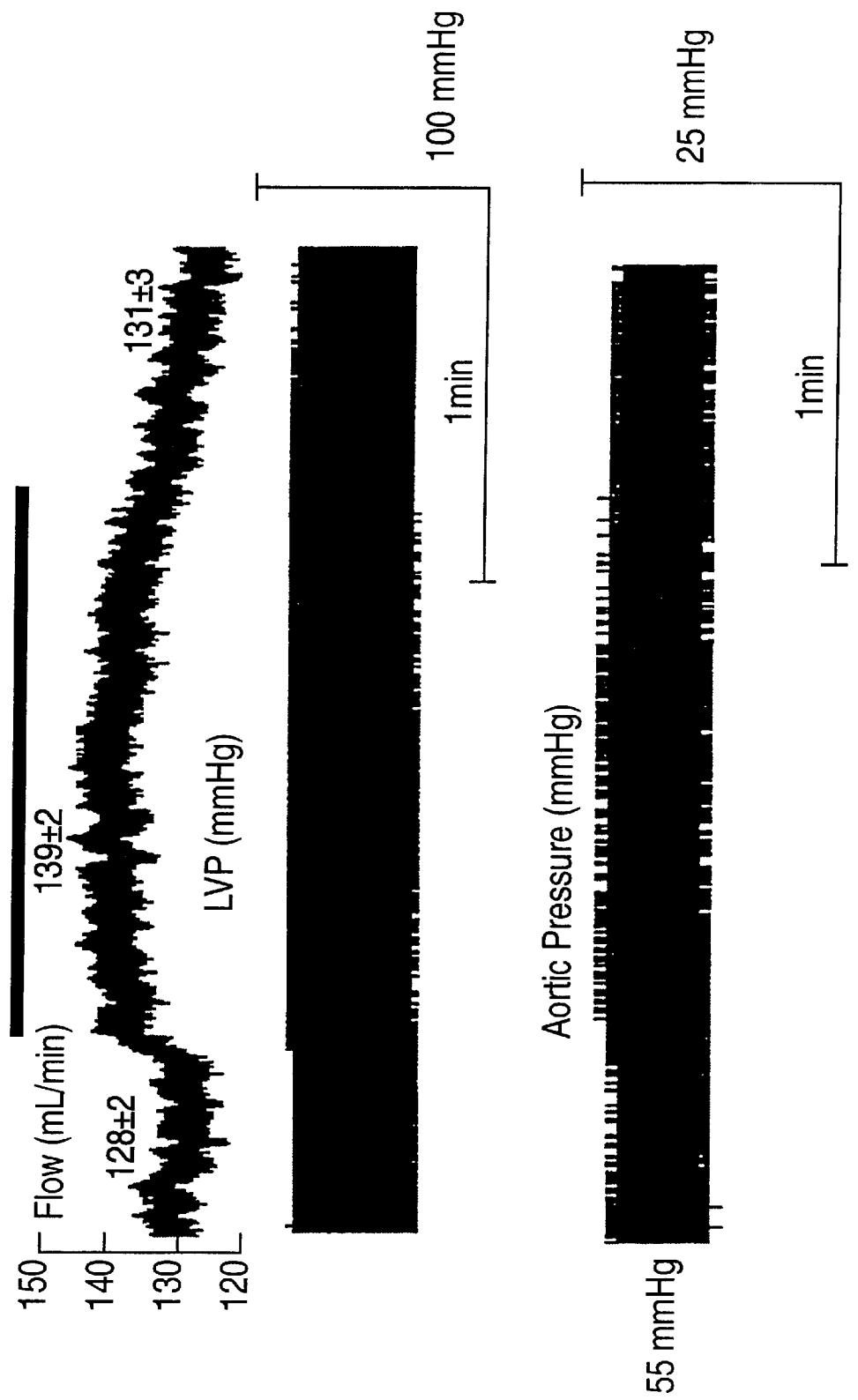

FIG. 14 is a series of graphs showing experimental results from another experiment, in which the right atrium being paced at 3 Hz, rather than the left ventricle being paced at 3.5 Hz, as in previously described experiments. Pacing and wiring are similar to those in the experiment of FIG. 11, except that the pacing electrodes are in the right atrium and the action potential is conducted from the right atrium to the left ventricle using the conduction pathways of the heart. The pulse parameters are 5 mA for 20 msec, with no delay after sensing a local action potential. The sensing electrode is shut off for 100 msec after it senses the local action potential, to reduce the possibility of identifying the controlling pulse as a local activation potential. In this experiment, an increase in flow of 9% was observed.

Figure 15:

FIG. 15 is a series of graphs showing experimental results from another experiment, similar to the experiment of FIG. 14, except that instead of using two controlling electrodes, four controlling electrodes were used. The controlling electrodes were arranged in a square, with the sensing electrode at the center of the square. One pair of controlling electrodes comprised an electrode at the apex of the left ventricle and an electrode at the base. The other two electrodes were located in the halfway between the base and the apex of the left ventricle and near the right ventricle (at either side of the left ventricle). The applied pulse was 10 mA for 20 msec at a delay of 2 msec. Both pairs of electrodes are electrified simultaneously.

In this experiment, an increase in the afterload and an increase in end-systolic LVP were observed. In addition, a decrease in end-diastolic LVP was observed. An increase in flow of about 7% is also shown in FIG. 15.

Figure 16:
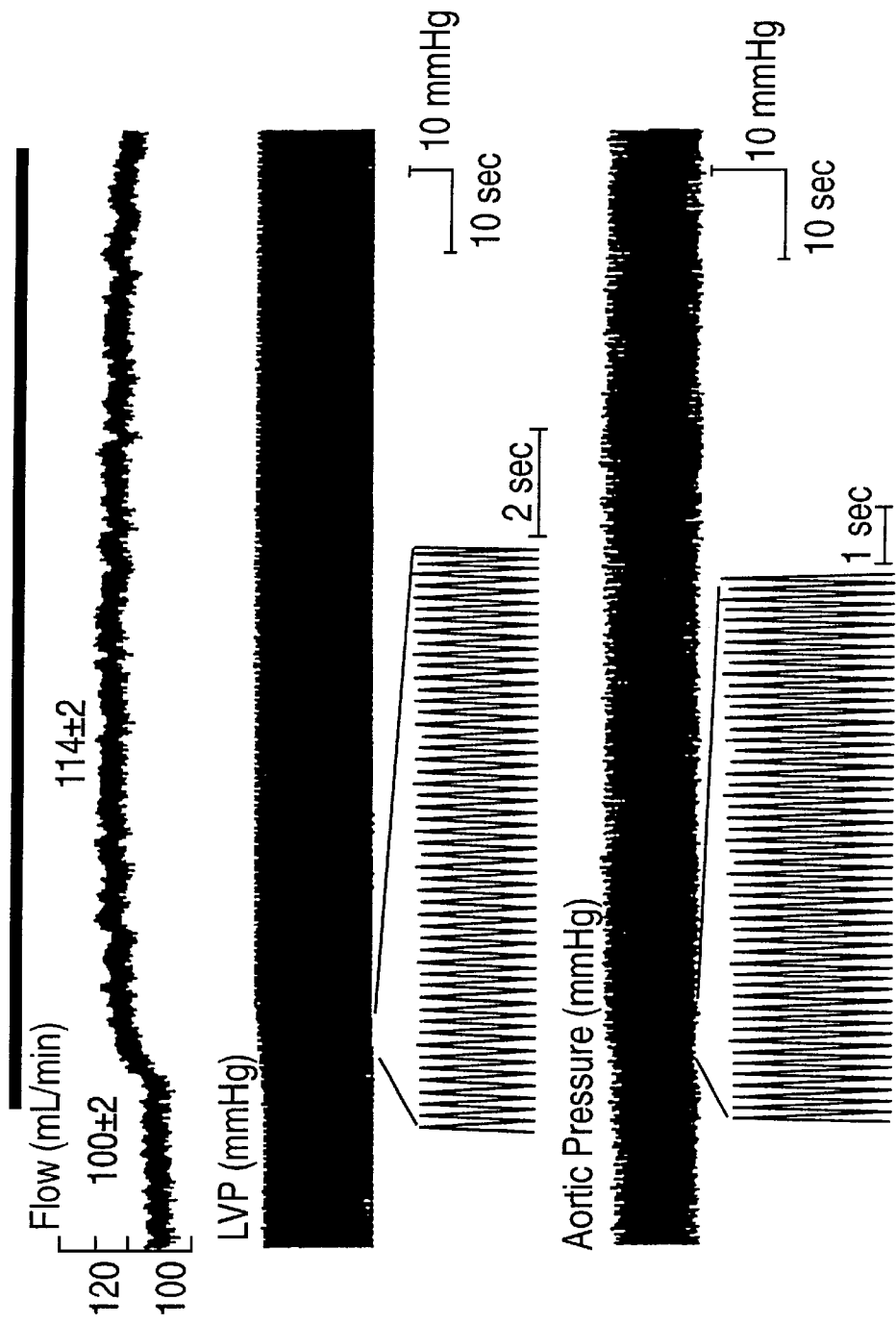

FIG. 16 is a series of graphs showing experimental results from another experiment, similar to the experiment of FIG. 14, except that no sensing electrode is used. Rather, an activation signal propagation time is estimated for calculation of the desired delay between pacing the right atrium and controlling the left atrium. The activation propagation time is estimated by measuring the time between the pacing signal and the contraction of the left ventricle. The delay time is 5 msec more than the calculated average propagation time and was about 140 msec. In this experiment, an increase in the afterload and an increase in LVP were observed. An increase in flow of about 14% is also shown in FIG. 16.

Figure 17:
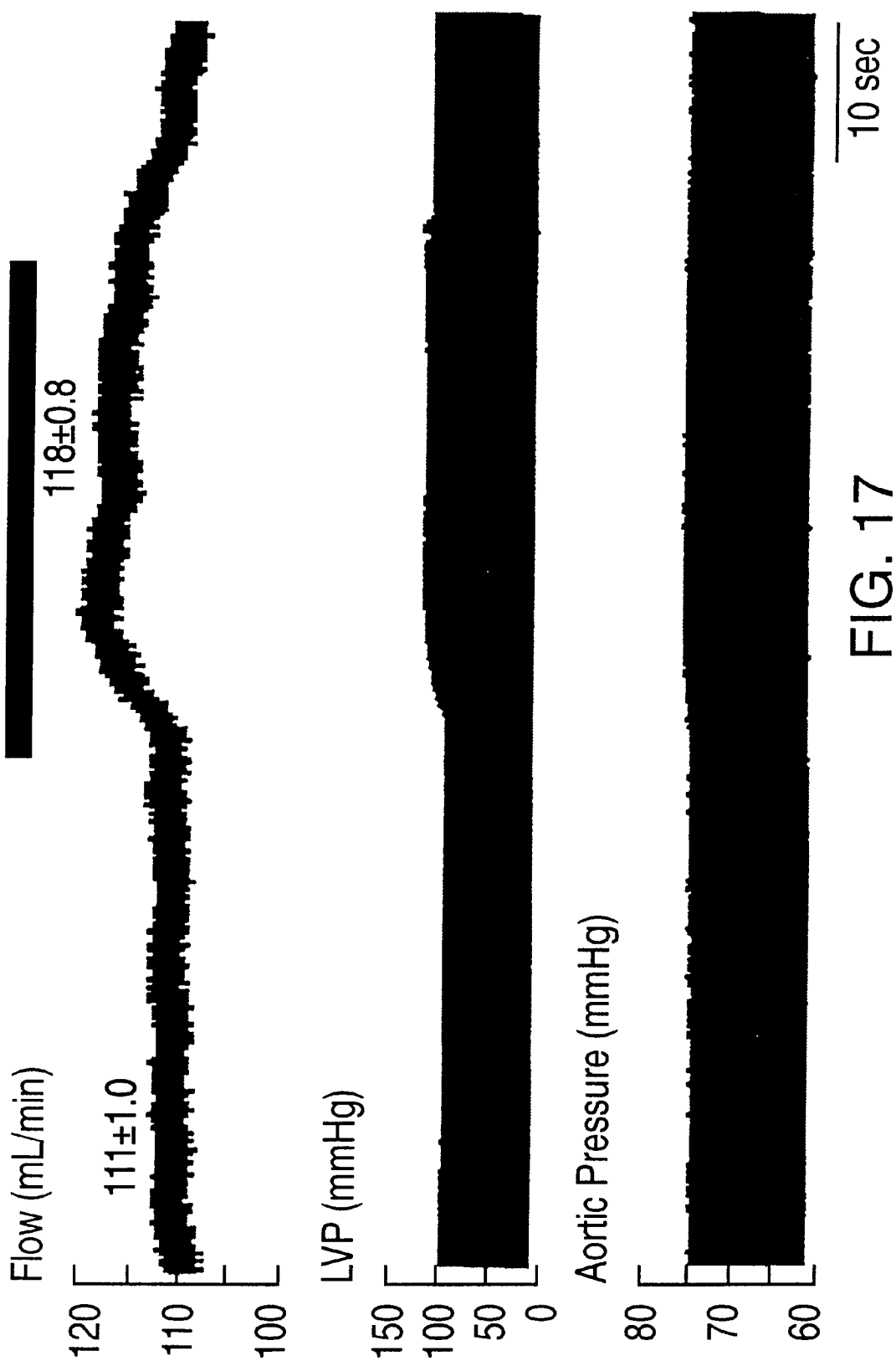

FIG. 17 is a series of graphs showing experimental results from another experiment, similar to the experiment of FIG. 14, except that no pacing electrodes are used. Rather, the isolated heart is allowed to pace at its own rhythm. The pulse parameters are a 20 msec long pulse of 10 mA applied to both pairs of electrodes simultaneously, at a delay of 2 msec after the sensing electrode senses a local activation potential.

In this experiment, an increase in the afterload and an increase in LVP were observed. An increase in flow of about 7% is also shown in FIG. 17. It should be noted that the baseline output of the heart was about 110 ml/min, which indicates an output of a healthy heart.

Figure 18A:
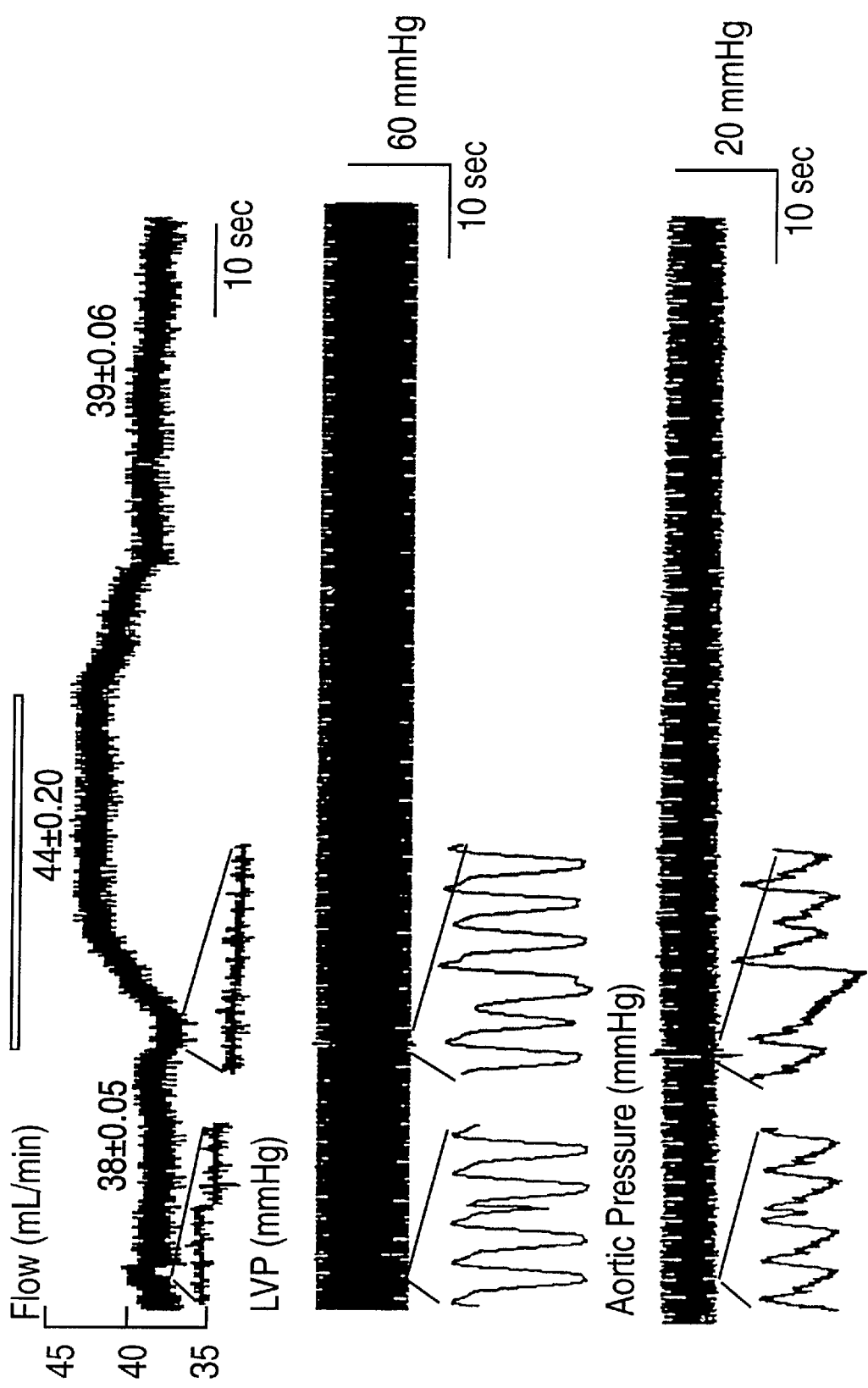

FIG. 18A is a series of graphs showing experimental results from another experiment in which the heart was made ischemic. The wiring is similar to that of FIG. 17, except that only one pair of controlling electrodes was used, one at the apex and one at the base of the left ventricle. The ischemia was designed to simulate a heart attack by stopping the flow of oxygenated solution to the coronary arteries for about ten minutes. After the flow of oxygenated solution was restarted a reduction in the cardiac output from 100 ml/min. to 38 ml/min. was observed. In addition, various arrhythmias in the activation of the heart were observed as a result of the ischemic incident. Controlling the heart, using a 20 msec pulse of 5 mA delayed 2 msec after the pacing, increased the flow by 16%. The sensing was blocked for between 100 and 200 msec after the sensing of a local activation. It should be noted that the controlling sequence worked even though the heart was arrhythmic.

One interesting result of the isolated heart experiments relates to pulse forms which do not induce fibrillation in the heart. It was determined that the pulse should not extend more than about half the duration of the left ventricle pressure wave (in this experimental setup, the pressure wave is measured, not electrical activity). In addition, a small delay (~5 msec) between the pacing and the pulse also appears to protect against fibrillation when the left ventricle is paced.

Figure 18B:
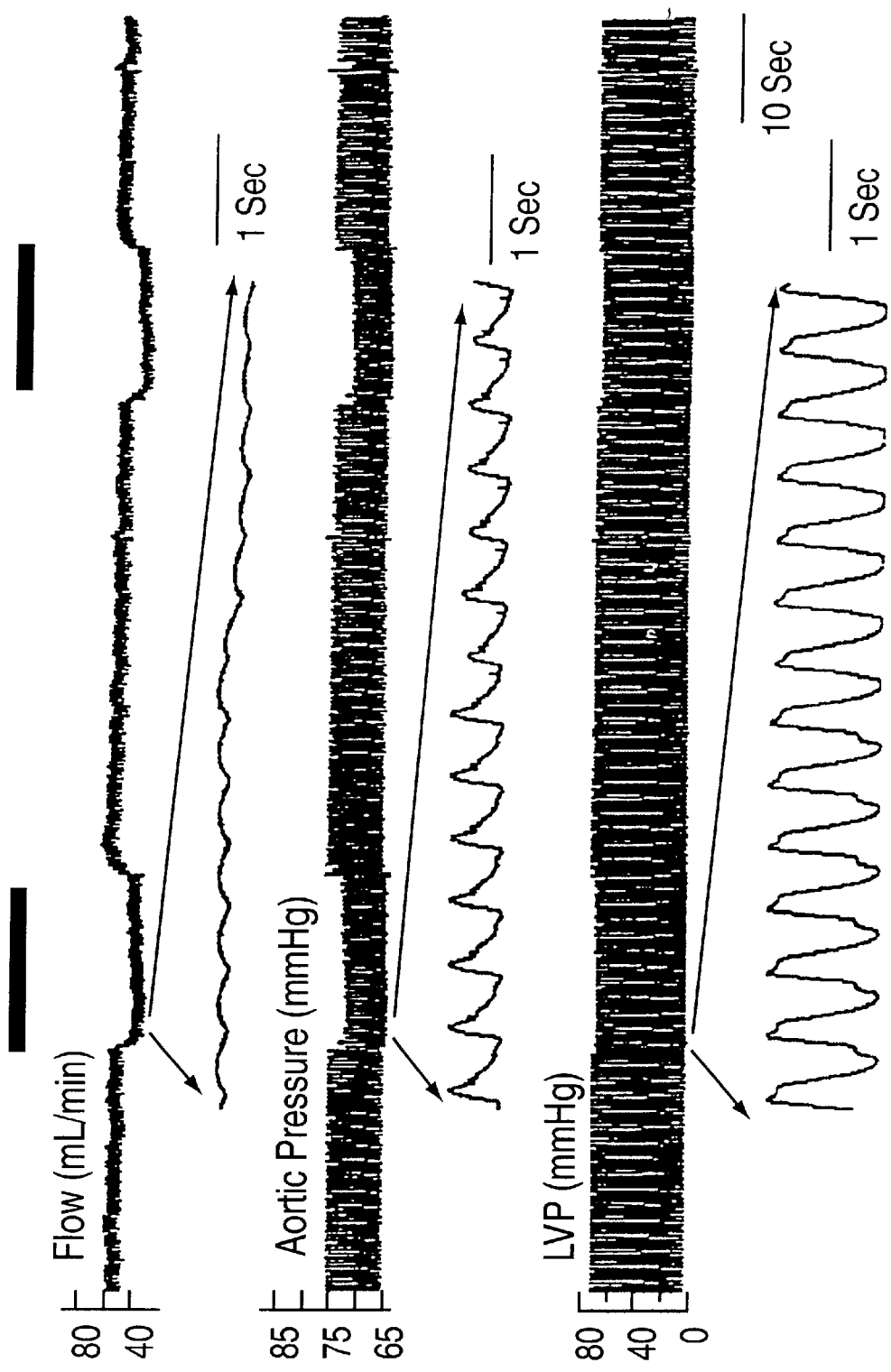

FIG. 18B is a series of graphs showing experimental results from another experiment in which the output of the heart was reduced. The heart was paced at the right atrium, using a pacing scheme similar to that of the experiment of FIG. 14. A controlling current was applied to the left ventricle using carbon electrodes. The controlling current was a 20 msec pulse of 5 mA amplitude applied at a delay of 30 msec after the pacing at the right atrium. Flow, LVP and Aortic pressure were all noticeably reduced as a result of this pulse.

Reducing the cardiac output is desirable in several circumstances, one of which is the disease "Hyperthropic Cardiomyopathy (HOCM)." This controlling scheme reduces the output of the left ventricle and the resistance against which the left ventricle is working, both of which are desirable for the above disease. It is hypothesized that the early controlling pulse (it is applied before the activation front from the right atrium reaches the left ventricle) works by extending the refractory periods of some of the cells in the left ventricle, thereby reducing the number of cells which take part in the systole and reducing the cardiac output. Presumably, different cells are affected each cardiac cycle. Alternatively, it may be that the precise delay determine which cells are affected. It is known to shorten the AV interval in order to improve the conditions of patients with HOCM. However, in the art, the entire ventricle is paced, albeit earlier. In the embodiment of the invention just described, the early applied electric filed does not cause an early contraction of the ventricle, and does not effectively shorten the AV interval, as done in the art.

Figure 19:
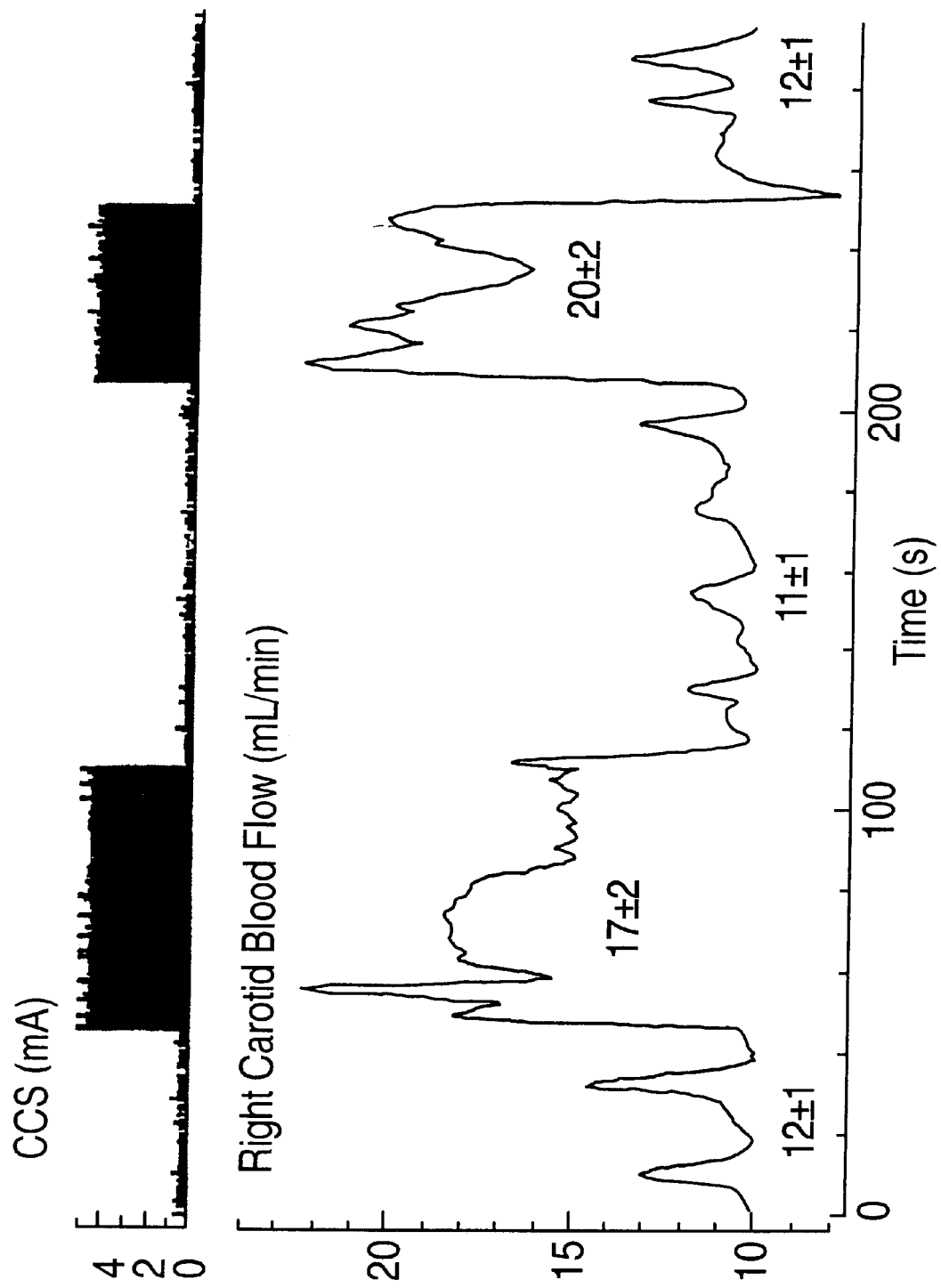
FIGS. 19–23 are each a series of graphs showing experimental results from experiments in which an in-vivo rabbit heart was controlled in accordance with an embodiment of the present invention.
Figure 20:
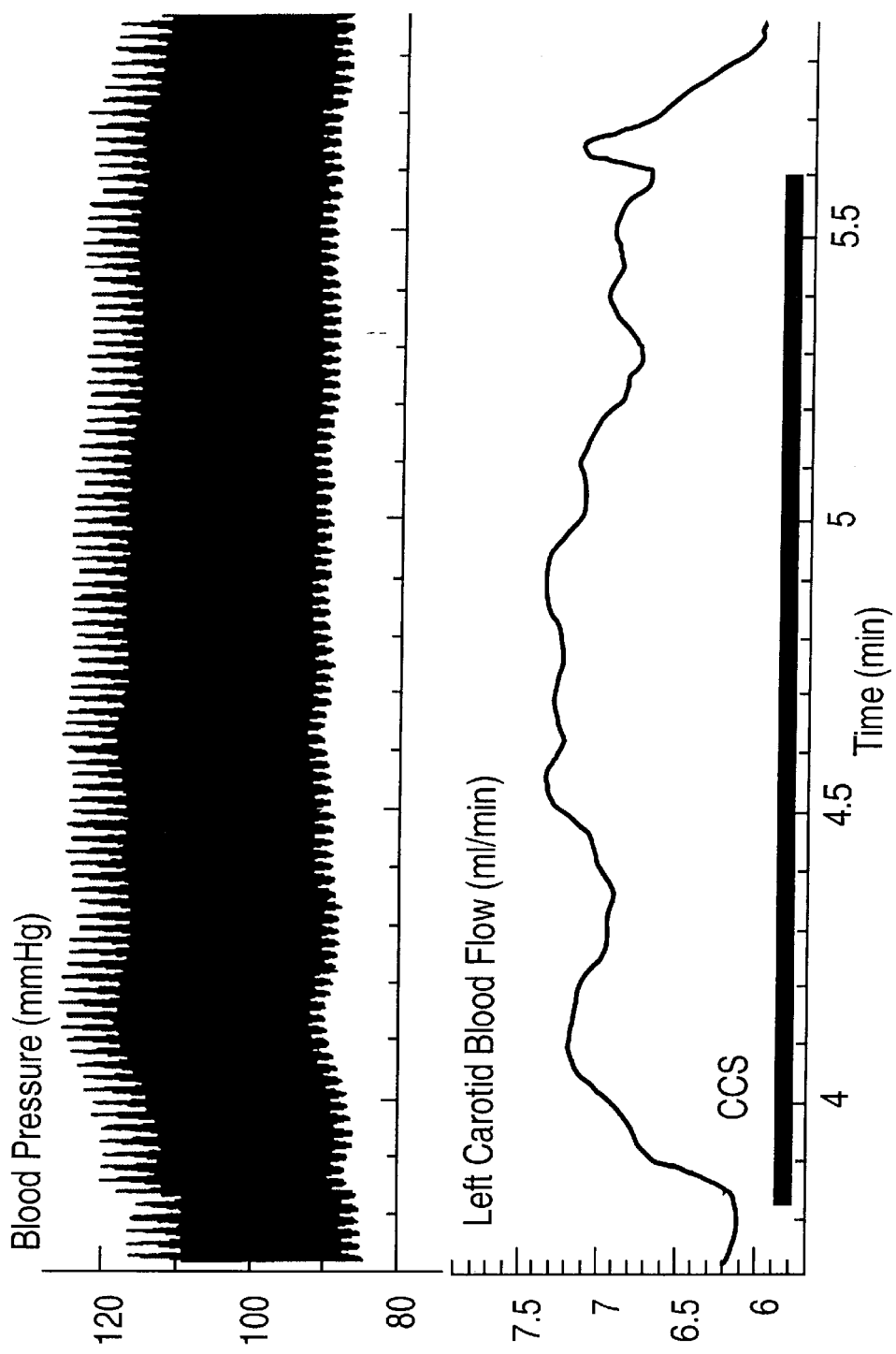

FIGS. 19 and 20 show the results of experiments performed on live animals on an in-vivo heart. In the experiment whose results are shown in FIG. 19, a live 2.5 Kg rabbit was anesthetized using a venous access in its pelvic region with its chest opened to expose the heart. The pericardium of the heart was removed to provide direct contact between the heart and electrodes. The heart was paced via the left ventricle using a pair of titanium electrodes and the controlling current was applied using a pair of carbon electrodes. As in previous experiments, the pacing was applied at the apex of the left ventricle and the controlling electrodes were applied one at the base and one at the apex of the left ventricle. The rabbit was artificially respirated and liquids were supplied through the venous access. A blood-pressure catheter was inserted into the left femoral artery to measure the arterial blood pressure. The right carotid artery was exposed and a magnetic flowmeter was placed thereon to measure the flow in the carotid artery. The flow in a carotid artery was measured rather than the flow in the aorta for reasons of convenience. However, it should be noted that the carotid arteries have a feedback mechanism by which they attempt to maintain a constant blood supply to the brain by contracting the artery if the flow is too high.

The controlling signal was a 40 msec pulse having a amplitude of 4 mA and applied 5 msec after the pacing signal. The pacing signal was a 2 msec, 2 mA pulse at 5 Hz. An increase in flow in the right carotid artery of between 54 and 72% was observed during the application of the controlling signal.

The experiment whose results are shown in FIG. 20 had a similar design to the experiment of FIG. 19, except that the flow was measured using an ultrasonic flowmeter. The controlling current was a 20 msec pulse having an amplitude of 2 mA and delayed 5 msec from the pacing signal (which was the same as in the experiment of FIG. 19). Both an increase in flow and in blood pressure were observed in this experiment.

Figure 21:
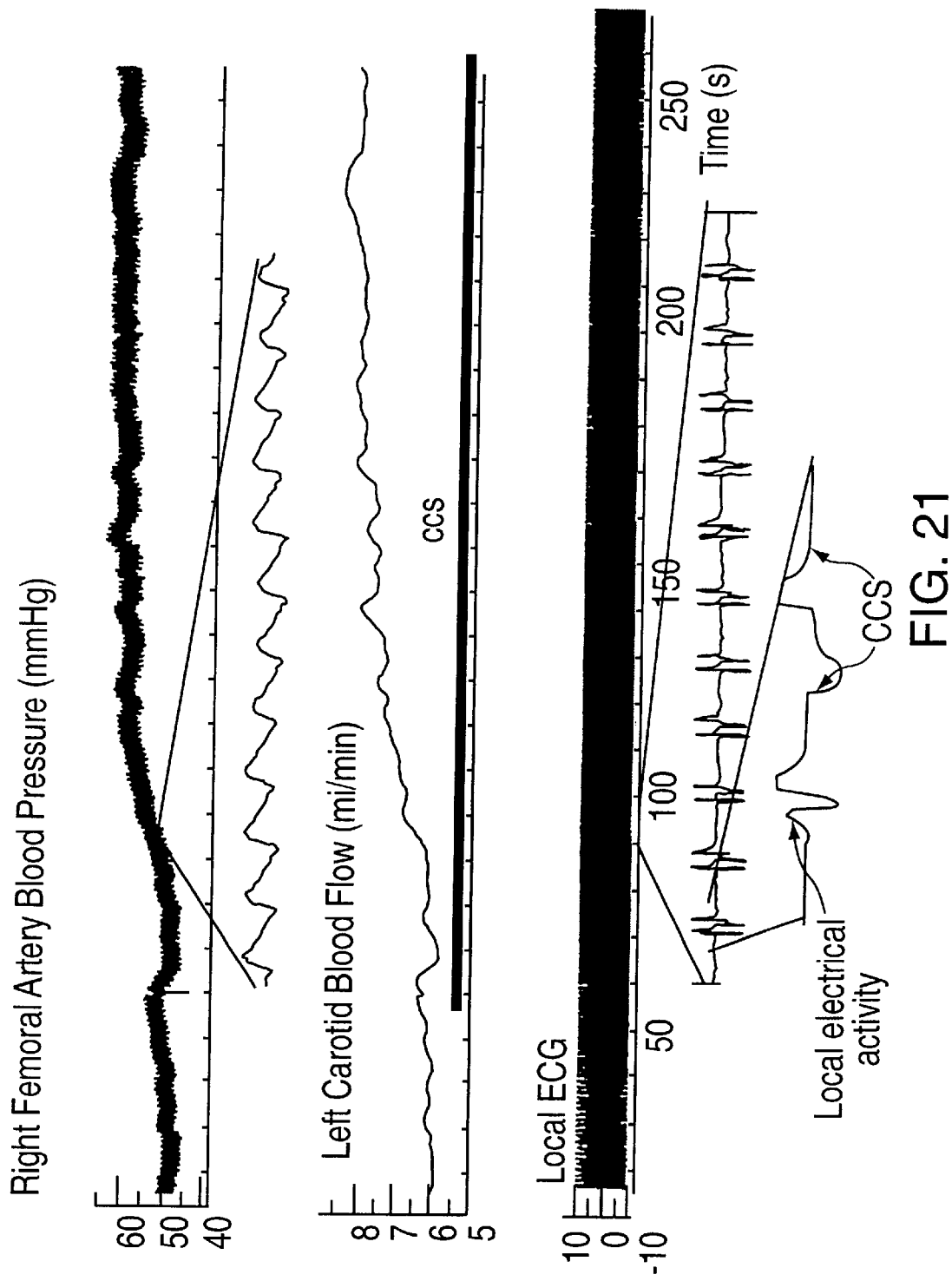

FIG. 21 shows the results of an experiment in an in-vivo heart in which the heart was not paced. It is similar to the experiments of FIGS. 19 and 20, in that blood pressure was measured in the right femoral artery and flow was measured, using an ultrasonic flowmeter, through the right carotid artery. The controlling pulse was applied using titanium-nitride electrodes, at the apex and at the base of the left ventricle. An iridium-platinum bi-polar electrode was placed at the apex of the left ventricle to sense the arrival of an activation front from the SA node of the heart. The controlling current was a 20 msec pulse, having an amplitude of 2 mA and applied 30 msec after the activation front was sensed. Increases in both the blood flow and the blood pressure were observed in this experiment.

Figure 22:
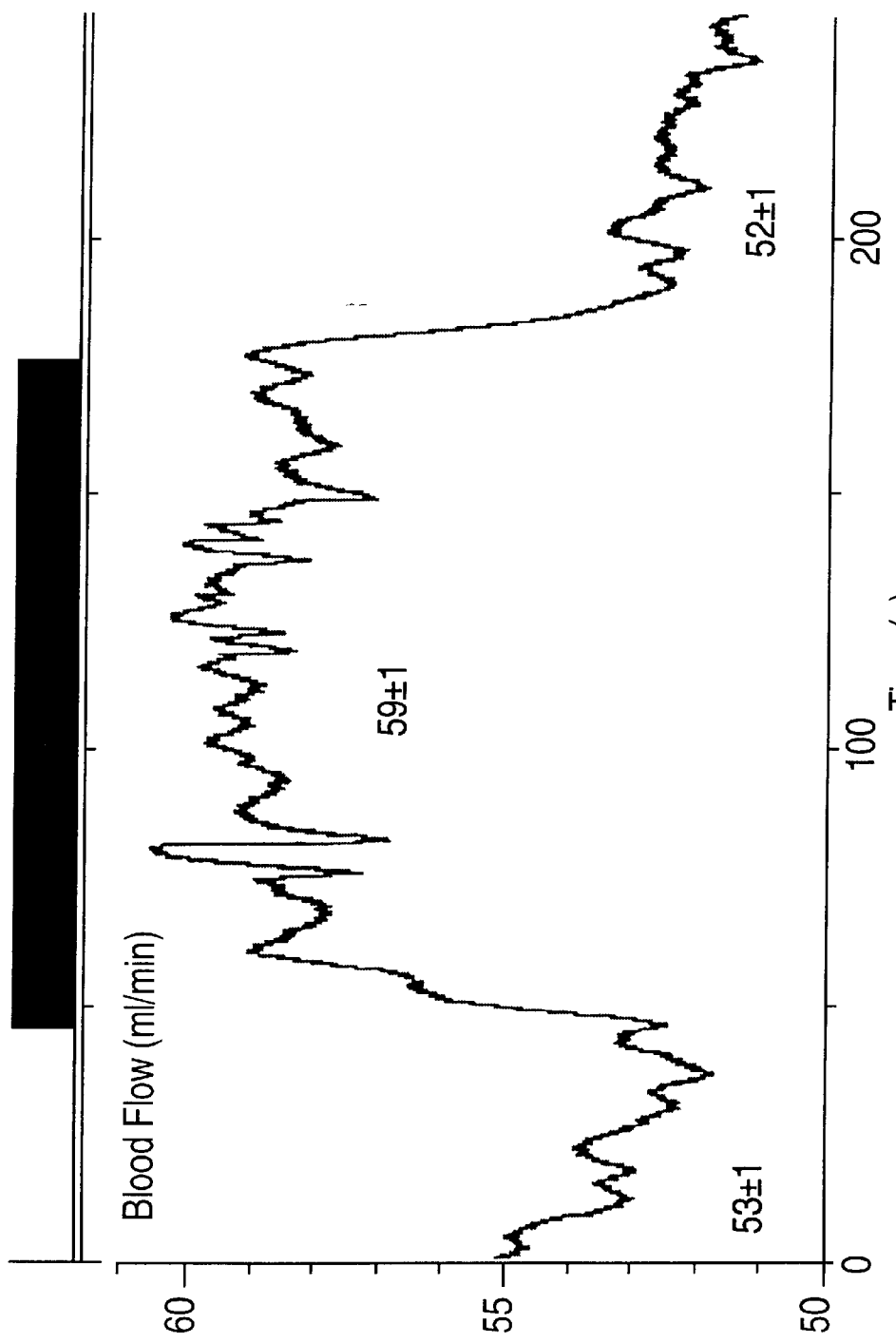
Figure 23:
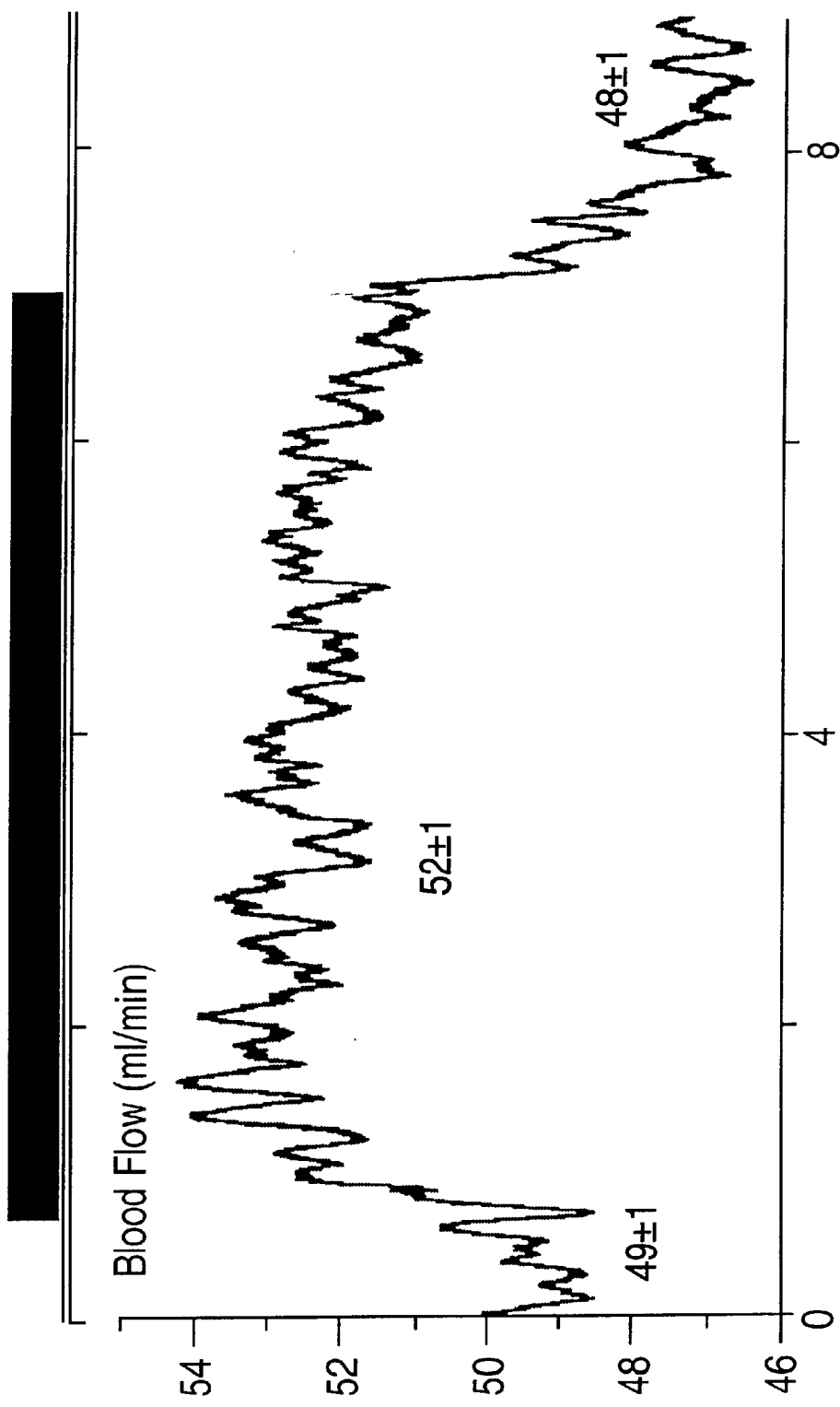

FIGS. 22 and 23 show the results of two experiments, similar to the experiment of FIG. 21, in which the flow parameter was measured on the ascending aorta. The heart of a 1.1 Kg rabbit was exposed and a sensing electrode (bipolar) was inserted, using a needle, into the apex of the heart. Two carbon electrodes were used to apply a controlling pulse to the heart, at the apex and the base of the left ventricle. The heart was not paced, it intrinsic pace was about 5 Hz. The control pulse was a 5 mA in amplitude and had a duration of 40 msec. There was no delay between the sensing of an activation front at the sensing electrodes and application of the pulse.

FIG. 22 shows an increase of about 11% in the aortic flow. FIG. 23, which shows the results of a repetition of the same experiment on the same animal at a later time, shows an increase of about 8%.

Although the present invention has been described mainly with reference to the heart, it should be appreciated that preferred embodiments of the present invention may be applied to other types of excitable tissue. In one example, skeletal muscle and smooth muscle can be controlled as described hereinabove. It should however be appreciated, that most muscles have different ion channels and different resting potentials than cardiac muscle, so that the general principles must be adapted to the individual physiology. In addition, the effects in a skeleton muscle may be due to recruitment of muscle fibers. Further, the present invention may be applied to neural tissue. For example, epileptic fits and tetanization may be controlled by damping the excitability of neural tissue, as described above. Alternatively, electrical control may be used in conjunction with electrical stimulation of denervated or atrophied muscles to increase the precision of stimulation. Additionally or alternatively, electrical control may be used to block or enhance conduction of stimuli along nervous pathways, for example, to control pain.

In a preferred embodiment of the invention, epileptic fits are controlled by suppressing Golgi cells, thus, reducing the excitability of associated neural tissues by reducing the amount of available calcium.

The above description of the present invention focuses on electrical control of cardiac tissue. However, since some aspect of the control may be related to calcium ion transport in the cardiac tissue, non-electrical control is also possible. One major advantage of non-electrical control is that even though incorrect synchronization of the control to the cardiac cycle may reduce the cardiac output, there is little or no danger of fibrillation. In one preferred embodiment of the present invention light is used to control calcium transport in portions of the heart. Laser light may be used to affect the calcium transport directly. Alternatively, a light activated chelator, which is introduced into at least some of the cells in a heart, may be activated by regular light to change the availability (increasing or reducing) of calcium in the illuminated cells. A controller in accordance with this embodiment of the invention, will include at least a light source and a light guide, preferably an optical fiber, which will convey the light to desired portions of the heart. Preferably, the optical fiber is a silicon-rubber optical fiber which is resistant to breakage. Alternatively, the controller comprises a plurality of light emitting elements, such as laser diodes, placed directly on the controlled tissue. Further alternatively, the light is provided by a catheter inserted into the heart and either floating in the heart or fixed to the heart wall. The controller preferably includes an ECG sensor for sensing local and/or global activation times, as described above.

One limitation of light over electrical current is that unless the body tissues are transparent to the particular wavelength used, light can only have a very localized effect, a global effect requires many light sources, which is invasive. One type of less invasive light source which may be useful is an optical fiber having a partially exposed sheath. Light will leak out of the fiber at the exposed portions, so a single fiber can illuminate a plurality of localities.

In an alternative embodiment of the invention, electromagnetic radiation at low and/or radio frequencies is used to affect calcium transport in the cardiac tissue. Several methods may be used to provide electromagnetic radiation. In one method, the entire heart is irradiated, preferably in synchrony with a sensed ECG of the heart. In another method, a phased array is used to aim the radiation at the heart. As noted above, the non-arrhythmic heart substantially repeats its position each cycle, so there is no problem of registration between an external source and a portion of the heart. In yet another method, an implanted device includes a plurality of antennas, each disposed adjacent to a portion of tissue to be controlled. The antennas may be powered by a central source. Alternatively, the antenna are concentrate externally applied radiation. Further alternatively, the antennas are coils which generate localized AC magnetic fields. It should be noted that electromagnetic radiation appears to be suitable for reducing calcium availability, which makes it suitable for reducing the oxygen demands of an infarcted tissue after a heart attack. In embodiments using electromagnetic-radiation as in light and electric current, there may be a long term reduction in the effectiveness of the controller due to adaptation mechanisms of the heart. Thus, in a preferred embodiment of the invention, the controller is not used continuously, with preferred rest periods between uses, being minutes, hours, days or weeks depending on the adaptation of the heart.

In a preferred embodiment of the invention, two or more control modalities are applied simultaneously, for example, applying both light radiation and electric fields. Alternatively, these modalities may be applied alternately, so as to cope with adaptation mechanisms. Preferably, each modality is applied until adaptation sets in, at which point the modality is switched.

Although the present invention has been described using a limited number of preferred embodiments, it should be appreciated that it is within the scope of the invention to combine various embodiments, for example, increasing the contractility of the left ventricle, while controlling the heart rate in the right atrium. It is also in the scope of the present invention to combine limitations from various embodiments, for example, limitations of pulse duration and pulse delay relative to an activation or limitations on electrode type and electrode size. Further, although not all the methods described herein are to be construed as being performed using dedicated or programmed controllers, the scope of the invention includes controllers which perform these methods. In some cases, limitations of preferred embodiments have been described using structural or functional language for clarity, however, the scope of the invention includes applying these limitations to both apparatus and methods.

It will be appreciated by a person skilled in the art that the present invention is not limited by what has thus far been particularly described. Rather, the present invention is limited only by the claims which follow.

What is claimed is:

1. A method of modifying the activity of the heart, or of a portion thereof, comprising applying to the Right Ventriculum of said heart a non-excitatory electric field of a magnitude, shape, duty cycle, phase, frequency and duration suitable to obtain a variation in cardiac muscle contraction, wherein said field is applied at a time at which it is unable to generate a propagating action potential.

2. A method according to claim 1, wherein the electric field is applied at the RV Septum.

3. A method according to claim 1 or 2, wherein the step of applying non-excitatory electric field comprises applying an alternated current electric field.

4. A method according to claim 1 or 2, wherein the step of applying non-excitatory electric field comprises applying an electric field that has a temporal envelope selected from the group consisting of exponential temporal envelope, sinusoidal temporal envelope, square temporal envelope, triangular temporal envelope, ramped temporal envelope, sawtooth temporal envelope and biphasic temporal envelope.

5. A method according to claim 1 or 2, wherein the variation in cardiac muscle contraction is an increase of the force of contraction of said heart, heart chamber or a portion thereof.

6. A method according to claim 1 or 2, wherein the variation in cardiac muscle contraction is followed by an increase of the stroke volume of a chamber of the heart.

7. A method according to claim 1 or 2, wherein the variation in cardiac muscle contraction is followed by an increase of the output flow of a chamber of the heart.

8. A method according to claim 1 or 2, wherein the variation in cardiac muscle contraction is followed by a change in pressure.

9. A method according to claim 8, wherein the pressure is end diastolic pressure or end systolic pressure of a chamber or aortic pressure.

10. A method according to claim 1 or 2, wherein the variation in cardiac muscle contraction is followed by a change of the heart rate.

11. A method according to claim 1 or 2, comprising sensing the activation of a portion of the heart at a suitable location, and thereafter calculating or estimating therefrom the activation time of the portion of the heart the activity of which it is desired to modify.

12. A method according to claim 11, further comprising determining the delay at which the non-excitatory electric field is to be applied from said activation time.

13. A method according to claim 11, wherein the activation is sensed by sensing a value of a parameter of an ECG, and wherein the activation time is estimated based on a delay value associated with the value of the parameter.

14. A method according to claim 1 or 2, wherein the activation of the Right Ventriculum is obtained by pacing, and wherein the application of the non-excitatory electric field is synchronized with the pacing signal and is effected with a timing relative to the pacing signal.

15. A method according to claim 1 or 2, wherein a defibrillating signal is provided to the heart, and wherein the application of the non-excitatory electric field is synchronized with said defibrillating signal.

16. A method according to claim 1 or 2, wherein the electric field is applied using electrodes selected from unipolar electrodes or bipolar electrodes.

17. A method according to, claim 1 or 2, wherein the application of the non-excitatory field is repeated during a plurality of heart beats, and wherein said repeated application is effected by skipping the application of the field to some of the beats in a train of consecutive heart beats.

18. A method according to claim 1 or 2, wherein the variation in cardiac muscle contraction comprises selectively and reversibly increasing or reducing the contractility of the Right Ventriculum of the heart relative to another portion or to the left ventricle.

19. A method according to claim 1 or 2, further comprising determining a desired range of values for at least one parameter of cardiac activity and controlling at least a local force of contraction of the heart to maintain said parameter within the desired range.

20. A method according to claim 1 or 2, wherein the application of the non-excitatory field is repeated during a plurality of heart beats, and wherein said repeated application is effected by reducing the frequency at which the beats are skipped is gradually reduced.

21. A method according to claim 1 or 2, wherein the application of the non-excitatory field is repeated during a plurality of heart beats, and wherein said repeated application is effected by changing between beats the size of the portion of the heart to which the field is applied.

22. A method of performing cardiac surgery comprising applying to the Right Ventriculum of the heart a non-excitatory electric field of a magnitude, shape, duty cycle, phase, frequency and duration suitable to control the electro-mechanical activity of the tissue in the area on which surgery is to be performed, wherein said field is inhibitory of a propagating action potential, and thereafter performing the required surgical procedure on said area.

23. A method of treating an abnormal activation of the heart, particularly fibrillation, comprising applying to the Right Ventriculum of said heart a non-excitatory electric field of a magnitude, shape and duration suitable to treat the abnormal activation condition, wherein said field is unable to generate a propagating action potential.

24. A method according to any of claims 22 to 23, wherein the electric field is applied at the RV Septum.

25. A method of performing cardio-vascular surgery comprising applying to the Right Ventriculum of the heart a non-excitatory electric field of a magnitude, shape, duty cycle, phase, frequency and duration suitable to reduce the output flow, contractility, or pressure thereof, when surgery is performed on tissue perfused by the flow of said chamber, wherein said field is unable to generate a propagating action potential, and thereafter performing the required surgical procedure on said area.

26. A method of reducing the output of the Right Ventriculum of a heart, comprising applying to a portion of said Right Ventriculum a non-excitatory electric field of a magnitude, shape, duty cycle, phase, frequency and duration suitable to obtain a desired change, wherein said field is applied at a time at which it is unable to generate a propagating action potential, and wherein reducing the output of the chamber is obtained by reducing the reactivity of said portion, or its sensitivity, to an activation signal, or by reversibly blocking its conduction pathway.

27. A method of modifying the electro-mechanical activation of the Right Ventriculum of a heart, comprising mapping the activation profile of the Right Ventriculum, determining a desired change in the activation, and modifying the conduction velocity in a non-arrhythmic segment of the Right Ventriculum using a non-excitatory electric field, wherein the non-excitatory electric field is of a magnitude, shape, duty cycle, phase, frequency and duration suitable to obtain the desired change.

28. A method of treating a segment of the Right Ventriculum of the heart which induces arrhythmias due to an abnormally low excitation threshold, comprising identifying the segment and applying thereto a desensitizing electric field such that said excitation threshold is increased to a normal range of values.

29. A method according to any of claims 27 to 28, wherein the electric field is applied at the RV Septum.

30. A method of modifying the activation profile of the Right Ventriculum of a heart, comprising mapping the activation profile of said Right Ventriculum, determining the desired change in the activation profile and changing the refractory period of at least a segment of the Right Ventriculum using a non-excitatory electric field, wherein the non-excitatory electric field is of a magnitude, shape, duty cycle, phase, frequency and duration suitable to obtain a desired change, and wherein said segment is selected from a segment that is not part of a reentry circuit or an arrhythmia focus in the heart, a segment that is a part of a reentry circuit or an arrhythmia focus in the heart, or an ischemic segment.

31. A method of modifying the activation profile of the Right Ventriculum of a heart, comprising mapping the activation profile of said Right Ventriculum, determining the desired change in the activation profile and reversibly blocking the activation of at least a segment of the Right Ventriculum using a non-excitatory electric field, wherein the non-excitatory electric field is of a magnitude, shape, duty cycle, phase, frequency and duration suitable to obtain a desired change, and wherein said segment is selected from a segment that is not part of a reentry circuit or an arrhythmia focus in the heart, a segment that is a part of a reentry circuit or an arrhythmia focus in the heart, or an ischemic segment.

32. A method of controlling a heart, comprising applying a non-excitatory electric field to a first portion of a the Right Ventriculum of said heart, such that a force of contraction of the first portion is lessened, and applying a non-excitatory electric field to a second portion of the Right Ventriculum, such that a force of contraction of the second portion is increased.

* * * * *

(12) INTER PARTES REEXAMINATION CERTIFICATE (0099th)
United States Patent
Ben-Haim et al.

(10) Number: US 6,330,476 C1
(45) Certificate Issued: *Sep. 8, 2009

(54) ELECTRICAL MUSCLE CONTROLLER USING A NON-EXCITATORY ELECTRIC FIELD

(75) Inventors: Shlomo Ben-Haim, Haifa (IL); Nissim Darvish, Haifa (IL); Maier Fenster, Petach Tikva (IL); Mike Yuval, Haifa (IL)

(73) Assignee: Impulse Dynamics N.V., Curacao (AN)

Reexamination Request:
No. 95/000,032, Dec. 31, 2003

Reexamination Certificate for:
Patent No.: 6,330,476
Issued: Dec. 11, 2001
Appl. No.: 09/723,989
Filed: Nov. 28, 2000

(*) Notice: This patent is subject to a terminal disclaimer.

Related U.S. Application Data

(63) Continuation of application No. 09/101,723, filed as application No. PCT/IL97/00012 on Jan. 8, 1997, now Pat. No. 6,317,631, and a continuation of application No. 08/595,365, filed on Feb. 1, 1996, now Pat. No. 5,738,096.
(60) Provisional application No. 60/009,769, filed on Jan. 11, 1996, provisional application No. 60/011,117, filed on Feb. 5, 1996, and provisional application No. 60/026,392, filed on Sep. 16, 1996.

(30) Foreign Application Priority Data

Jan. 8, 1996 (IL) .................................. 116699
Sep. 17, 1996 (IL) ............................... 119261

(51) Int. Cl.
*A61N 1/362* (2006.01)

(52) U.S. Cl. ............................................. 607/9; 607/14
(58) Field of Classification Search .................. None
See application file for complete search history.

(56) References Cited

U.S. PATENT DOCUMENTS

| | | |
|---|---|---|
| 3,572,345 A | 3/1971 | Auphan |
| 3,587,567 A | 6/1971 | Schiff |
| 3,651,805 A | 3/1972 | Breiling |
| 3,942,536 A | 3/1976 | Dahl et al. |
| 3,952,750 A | 4/1976 | Mower et al. |
| 4,030,509 A | 6/1977 | Heilman et al. |
| 4,106,494 A | 8/1978 | McEachern |
| 4,164,216 A | 8/1979 | Person |
| 4,184,493 A | 1/1980 | Mower et al. |
| 4,202,340 A | 5/1980 | Mower |

(Continued)

FOREIGN PATENT DOCUMENTS

| | | |
|---|---|---|
| EP | 148687 | 12/1984 |
| EP | 0314078 A1 | 5/1989 |
| EP | 072724 B1 | 8/1996 |
| JP | 04117967 A2 | 4/1992 |
| JP | 4365493 | 12/1992 |

(Continued)

OTHER PUBLICATIONS

Antman, E.M. et al. "Treatment of 150 Cases of Life–Threatening Digitalis Intoxication with Digoxin–Specific Fab Antibody Fragments," Jun. 1990 Circulation: vol. 81: No. 6: pp. 1744–1752.

(Continued)

*Primary Examiner*—Beverly M. Flanagan

(57) ABSTRACT

A method of modifying the force of contraction of at least a portion of a heart chamber, including providing a subject having a heart, comprising at least a portion having an activation, and applying a non-excitatory electric field having a given duration, at a delay after the activation, to the portion, which causes the force of contraction to be increased by at least 5%.

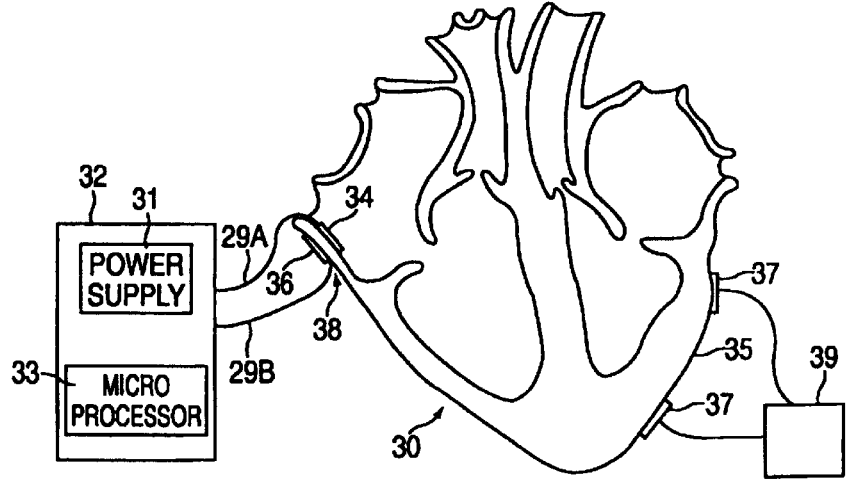

U.S. PATENT DOCUMENTS

| | | |
|---|---|---|
| 4,223,678 A | 9/1980 | Mower |
| 4,237,895 A | 12/1980 | Johnson |
| 4,273,114 A | 6/1981 | Berkalow et al. |
| 4,312,354 A | 1/1982 | Walters |
| 4,316,472 A | 2/1982 | Mower et al. |
| 4,384,585 A | 5/1983 | Zipes |
| 4,387,717 A | 6/1983 | Brownlee |
| 4,403,614 A | 9/1983 | Engle et al. |
| 4,407,288 A | 10/1983 | Mirowski et al. |
| 4,440,172 A | 4/1984 | Langer |
| 4,506,680 A | 3/1985 | Stokes |
| 4,543,956 A | 10/1985 | Herscovici |
| 4,547,831 A | 10/1985 | Hellman et al. |
| 4,554,922 A | 11/1985 | Prystowsky et al. |
| 4,559,846 A | 12/1985 | Mower |
| 4,566,456 A | 1/1986 | Koning |
| 4,572,191 A | 2/1986 | Langer et al. |
| 4,628,934 A | 12/1986 | Pohndorf et al. |
| 4,651,716 A | 3/1987 | Forester |
| 4,674,508 A | 6/1987 | DeCote |
| 4,679,572 A | 7/1987 | Baker, Jr. |
| 4,690,155 A | 9/1987 | Hess |
| 4,726,379 A | 2/1988 | Altman et al. |
| 4,765,341 A | 8/1988 | Mower et al. |
| 4,830,006 A | 5/1989 | Haluska et al. |
| 4,928,688 A | 5/1990 | Mower et al. |
| 4,979,507 A | 12/1990 | Heinz et al. |
| 4,998,531 A | 3/1991 | Bocchi et al. |
| 5,002,052 A * | 3/1991 | Haluska .................. 607/4 |
| 5,003,976 A | 4/1991 | Alt |
| 5,020,544 A | 6/1991 | Dahl et al. |
| 5,022,396 A | 6/1991 | Watanabe |
| 5,044,375 A | 9/1991 | Bach, Jr. et al. |
| 5,083,564 A | 1/1992 | Scherlag |
| 5,087,243 A | 2/1992 | Avitall |
| 5,097,832 A | 3/1992 | Buchanan |
| 5,111,815 A | 5/1992 | Mower |
| 5,129,394 A | 7/1992 | Mehra |
| 5,137,021 A | 8/1992 | Wayne et al. |
| 5,156,147 A | 10/1992 | Warren et al. |
| 5,156,149 A | 10/1992 | Hudrlik |
| 5,161,527 A | 11/1992 | Nappholz |
| 5,163,428 A | 11/1992 | Pless |
| 5,199,428 A | 4/1993 | Obel et al. |
| 5,205,284 A | 4/1993 | Freeman |
| 5,213,098 A | 5/1993 | Bennett et al. |
| 5,236,413 A | 8/1993 | Feiring |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,320,642 A | 6/1994 | Scherlag |
| 5,320,643 A | 6/1994 | Roline et al. |
| 5,327,887 A | 7/1994 | Nowakowski |
| 5,346,506 A | 9/1994 | Mower et al. |
| 5,353,800 A | 10/1994 | Pohndorf |
| 5,366,486 A | 11/1994 | Zipes et al. |
| 5,368,040 A | 11/1994 | Carney |
| 5,370,665 A | 12/1994 | Hudrlik |
| 5,386,837 A | 2/1995 | Sterzer |
| 5,387,419 A | 2/1995 | Levy |
| 5,391,192 A | 2/1995 | Lu |
| 5,391,199 A | 2/1995 | Ben-Haim |
| 5,398,683 A | 3/1995 | Edwards |
| 5,415,629 A | 5/1995 | Henley |
| 5,417,717 A | 5/1995 | Salo et al. |
| 5,419,763 A | 5/1995 | Hildebrand |
| 5,425,363 A | 6/1995 | Wang |
| 5,431,688 A | 7/1995 | Freeman |
| 5,443,485 A | 8/1995 | Housworth |
| 5,447,520 A | 9/1995 | Spano |
| 5,447,525 A | 9/1995 | Powell et al. |
| 5,458,568 A | 10/1995 | Racchini et al. |
| 5,464,020 A | 11/1995 | Lerner |
| 5,468,254 A | 11/1995 | Hahn |
| 5,472,453 A | 12/1995 | Alt |
| 5,476,484 A | 12/1995 | Hedberg |
| 5,476,485 A | 12/1995 | Weinberg et al. |
| 5,476,497 A | 12/1995 | Mower et al. |
| 5,482,052 A | 1/1996 | Lerner |
| 5,499,971 A | 3/1996 | Shapland et al. |
| 5,501,662 A | 3/1996 | Hofman |
| 5,514,162 A | 5/1996 | Bornzin et al. |
| 5,520,642 A | 5/1996 | Bigagli et al. |
| 5,531,764 A | 7/1996 | Adams et al. |
| 5,540,722 A | 7/1996 | Clare |
| 5,556,421 A | 9/1996 | Prutchi |
| 5,568,809 A | 10/1996 | Ben-Haim |
| 5,571,143 A | 11/1996 | Hoegnelid et al. |
| 5,584,803 A | 12/1996 | Stevens |
| 5,584,868 A | 12/1996 | Salo et al. |
| 5,587,200 A | 12/1996 | Lorenz |
| 5,601,609 A | 2/1997 | Duncan |
| 5,601,611 A | 2/1997 | Fayram et al. |
| 5,620,468 A | 4/1997 | Mongeon et al. |
| 5,626,622 A | 5/1997 | Cooper |
| 5,634,899 A | 6/1997 | Shapland et al. |
| 5,649,966 A | 7/1997 | Noren et al. |
| 5,651,378 A | 7/1997 | Matheny et al. |
| 5,662,687 A | 9/1997 | Hedberg et al. |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,697,953 A | 12/1997 | Kroll et al. |
| 5,713,935 A | 2/1998 | Prutchi et al. |
| 5,720,768 A | 2/1998 | Verboven-Nelissen |
| 5,735,876 A | 4/1998 | Kroll |
| 5,738,096 A | 4/1998 | Ben-Haim |
| 5,738,105 A | 4/1998 | Kroll |
| 5,749,906 A | 5/1998 | Kieval et al. |
| 5,755,740 A | 5/1998 | Nappholz |
| 5,779,661 A | 7/1998 | Stephen et al. |
| 5,782,876 A | 7/1998 | Flammang |
| 5,782,881 A | 7/1998 | Lu et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,865,787 A | 2/1999 | Shapland et al. |
| 5,871,605 A | 2/1999 | Bett |
| 5,906,607 A | 5/1999 | Taylor |
| 5,913,876 A | 6/1999 | Taylor |
| 5,927,284 A | 7/1999 | Borst |
| 6,032,074 A | 2/2000 | Collins |
| 6,032,672 A | 3/2000 | Taylor |
| 6,041,252 A | 3/2000 | Walker et al. |
| 6,057,374 A | 5/2000 | Huntington et al. |
| 6,067,470 A | 5/2000 | Mower |
| 6,071,305 A | 6/2000 | Brown et al. |
| 6,136,019 A | 10/2000 | Mower |
| 6,141,587 A | 10/2000 | Mower |
| 6,151,586 A | 11/2000 | Brown |
| 6,157,859 A | 12/2000 | Alt |
| 6,178,351 B1 | 1/2001 | Mower |
| 6,295,470 B1 | 9/2001 | Mower |
| 6,317,631 B1 * | 11/2001 | Ben-Haim et al. ............. 607/9 |

| | | |
|---|---|---|
| 6,337,995 B1 | 1/2002 | Mower |
| 6,341,235 B1 | 1/2002 | Mower |
| 6,343,232 B1 | 1/2002 | Mower |
| 6,411,847 B1 | 6/2002 | Mower |
| RE38,119 E | 5/2003 | Mower |

FOREIGN PATENT DOCUMENTS

| | | |
|---|---|---|
| JP | 7126600 | 5/1995 |
| JP | 8243176 A2 | 8/1996 |
| WO | WO 92/00716 | 1/1992 |
| WO | WO 95/08316 | 3/1995 |
| WO | WO 96/16696 | 6/1996 |
| WO | WO 97/25101 | 7/1997 |
| WO | WO 98/19719 | 5/1998 |

OTHER PUBLICATIONS

Antoni, H. et al. "Polarization Effects of Sinusoidal 50–Cycle Alternating Current on Membrane Potential of Mammalian Cardiac Fibers". Pfluegers Arch. 314, pp. 274–291 (1970).

Bakker, P.F., et al., "Beneficial Effects of Biventricular Pacing of Congestive Heart Failure", PACE, vol. 17, Apr. 1994, Part 11, p. 318.

Bakker, P.F., et al., "Biventricular Pacing Improves Functional Capacity in Patients with End–Stage Congestive Heart Failure" PACE, vol. 17. Apr. 1995, Part 11, p. 825.

Barghear K. et al., "Prolongation of Monophasic Action Potential Duration and the Refractory Period in the Human Heart by Tedisamil, a New Potassium–Blocking Agent", J. Eur Heart 15 (10), Oct. 1994, pp. 1409–1414.

Bers, D.M., Excitation–Contraction Coupling and Cardiac Contractile Force, Kluwer Academic Publishers, London, 1993.

Borst, et al., "Coronary Artery Bypass Grafting Without Cardiopulmonary Bypass and Without Interuption of Native Coronary Flow Using a Novel Anastomosis site restraining device ("Octupus")", Journal of the American College of Cardiology, 27 (6), May 1996, pp. 1356–1364.

Cano, N.J. et al. "Dose–Dependent Reversal of Digoxin–Inhibited Activity of an In–Vitro NA+K+ATPase Model by Digoxin–Specific Antibody," May 1996; pp. 107–1011; Toxicology Letters; vol. 85; No. 2, pp. 107–111.

Cazeau S. et al., "Multisite Pacing for End–Stage Heart Failure: Early Experience", Pacing and Clinical Electrophysiology vol. 19, Nov. 1996, Part 11, pp. 1748–1757.

Cooper, W., "Postaxtrasystolic Potentiation: Do We Really Know What It Means and How to Use It?" Circulation, vol. 88, No. 6. Dec. 1993, pp. 2962–2971.

Dillon, SM., "Optical Recordings in the Rabbit Heart Show that Defibrillation Strength Shocks Prolong the Duration of Depolarization and the Refractory Period" in Circ Res., 69(3), Sep. 1991, pp. 842–856.

Dillon, SM., abstract of "Synchronized Repolarization After Defibrillation Shocks, A Possible Component of the Defibrillation Process Demonstration By Optical Recordings in Rabbit Heart", Circulation, May 1992, vol. 85, No. 5, pp. 1865–1878.

Fain, E.S., et al. "Improved Internal Defibrillation Efficacy with a Biphasic Waveform", American Heart Journal 117 (2), Feb. 1989, pp. 358–364.

Fleg, J.L. et al., "Impact of Age on the Cardiovascular Response to Dynamic Upright Exercise in Healthy Men and Women", J. Appl. Physiol., vol. 78, 1995, pp. 890–900.

Foster, A.H, et al., "Acute Hemodynamic Effects of Atrio–Biventricular Pacing in Humans", 1995, The Society of Thoracic Surgeons vol. 59, pp. 294–299.

Franz, M.R., "Bridging the Gap Between Basic and Clinical Electrophysiology: What Can be Learned from Monophasic Action Potential Recordings?", J. Cardiovasc Electrophysiol 6(8), Aug. 1994, pp. 699–710.

Franz, M.R., "Method and Theory of Monophasic Action Potential Recording", Prog. Cardiovasc Dis 33 (6), May–Jun. 1991, pp. 347–368.

Franz, M.R., "Progress in Cardiovascular Disease: Monophasic Action Potential Symposium, I. Introduction", Prog. Cardiovasc Dis 33 (6), May–Jun. 1991 pp. 345–346.

Fromer et al., "Ultrarapid Subthreshold Stimulation for Termination of Atrioventricular Node Reentrant Tachycardia", Journal of the American College of Cardiology 20 (Oct. 1992), pp. 879–883.

Fu, P and B.J. Bardaljian, "System Identification of Electrically Coupled Smooth Muscle Cells: The Passive Electrically Coupled Smooth Muscle Cells: The Passive Electrical Properties", published in IEEE Transactions on Biomedical Engineering, 38(11), pp. 1130–1140, 1991.

Ham, Frederic M and Han, Soowhan, "Classification of Cardiac Arrhythmias Using Fuzzy Artmap"; IEEE Transactions on Biomedical Engineering, vol. 43, No. 4, Apr. 1996, pp. 425–430.

Hoffman, B.F. et al., "Effects of Postextrasystolic Potentiation on Normal & Failing Hearts", Bulletin of New York Academy of Medicine, 41 in 1965, pp. 498–534.

Josephson, M.E., Clinical Cardiac Electrophysiology: Techniques and Interpertations, 2nd. Edition, Lea & Febiger, Philadelphia, 1991.

King, A. et al., The Inotropic Action of Paired Pulse Stimulation in the Normal and Failing Heart: An Experimental Study. Cardiovascular Research, vol. 2, Apr. 1968, pp. 122–129.

Knisley et al., "Prolgongation and Shortening of Action Potentials by Electrical Shocks in Frog Ventricular Muscle", American Journal of Physiology 6 (Heart Circ. Physiol. 35, 1994) pp. H2348–H2358.

Koller, et al., "Relation Between Repolarization and Refractoriness During Programmed Electrical Stimulation in the Human Bigth Ventriole", Circulation 91(9), pp. 2378–2384, 1995.

Langberg, Jonathan J. et al., "Identification of Ventricular Tachycardia with Use of the Morphology of the Endocardial Electrogram", Circulation, vol. 77, No. 6, Jun. 1988, pp. 1363–1369.

McVeigh, E.R et al., "Noninvasive Measurement of Transmural Gradients in Myocardial Strain with MR Imaging", Radiology 180 (3), Sep. 1991, pp. 677–683.

Mercendo, A.D., et al., "Automated Detection of Tachardias by Antitachicardis Devices", Chapter 100, pp. 943–948, in Cardiac Electrophysiology from Cell to Bedside, Eds. Douglas P. Zipes and Jose Jalife, publishers W.B. Saunders Company (1990), pp. 943–948.

Moran, R.J. et al; "Digoxin–Specific Fab Fragments Impair Renal Function in the Rat" 1994; pp. 854–856; Journal of Pharmacy and Pharmacology, vol. 46: No. 10.

Morse, et al., "A Guide to Cardiac Pacemakers, Defibrillators and Related Products", Drooge Computing Services, Durham, NC.

Merck Manual. The, Section 3, the 16th Edition of the Merck Manual, Published in 1992.

Paul, VE., et al. "Automatic Recognition of Ventricular Arrythmias Using Temporal Electrogram Analysis" Pace, vol. 14, pp. 1265–1273, (1991).

Qiuzhen Xue et al., "Neural–Network–Based Adaptive Matched Filtering for QRS Detection", IEEE Transactions on Biomedical Engineering, vol. 39, No. 4, Apr. 1992, pp. 317–329.

Saksena et al., "Dual–site Atrial Pacing in Atrial Fibrillation", JACC, vol. 28, No. 3, Sep. 1998, pp. 687–694.

Shumaik, G.M. et al, "Oleander Poisoning: Treatment with Digoxin–Specific Fab Antibody Fragments;" Jul. 1988; pp. 732–735; Annals of Emergency Medicine; vol. 17; No. 7.

Sweeny RJ. et al., abstract of "Countershock Strength–Duration Relationship for Myocardial Refractory Period Extension", Acad Emerg. Med., Jan. 1995, vol. 2, No. 1, pp. 57–62.

Sweeny RJ, et al., abstract of "Refractory Interval After Transcardiac Shocks During Ventricular Fibrillation", Circulation, Dec. 1998, vol. 94, No. 11, pp. 2947–2952.

Sweeny RJ, et al., abstract of "Ventricular Refractory Period Extension Caused by Defibrillation Shocks", Circulation, Sep. 1990, vol. 82, No. 3, pp. 965–972.

Talit, U. et al., "The Effect of External Cardiac Pacing on Stroke Volume", Pace 13, May 1990. pp. 598–602.

Tsong, T.Y., "Electroportion of Cell Membranes" Aug. 1991; pp. 297–306; Biophysical Journal; vol. 60.

Verrier, et al/, "Electrophysiologic Basis for T Wave Altemans as an Indeax of Vulnerability to Ventricular Fibrillation" Journal of Cardiovascular Electrophysiology, vol. 5, pp. 445–461, 1994.

Webster, John G., ed., Design of Cardiac Pacemakers, IEEE Press, Piscataway, New Jersey, 1995.

Wessale, J.L. et al., "Stroke volume and Three Phase Cardiac Ouput Rate Relationship with Ventricular Pacing" Pace 13, May 1990, pp. 673–680.

Wirtzfeld, A. et al., "Physiological Pacing: Present Status and Future Developments", Pace 10 Jan.–Feb. 1987, Part I, pp. 41–57.

Zipes, D et al., Cardiac Electrophysiology from Cell to Bedside, 1990, W.B. Saunders Co., Philadelphia.

Guidant Product Catalogue, 2001, 2 pages.

"The Latest Tetralogy of Fallot Discussion with Graphical Support Including Video of Echocardiography and Catherization" Pediatric Electrophysiologypicu Book ("An On–Line Resource for Pediatric Critical Care").

* cited by examiner

US 6,330,476 C1

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 22, 25 and 27–32 is confirmed.

Claims 1, 2, 23 and 26 are cancelled.

Claims 3–8, 10, 11, 14–21 and 24 are determined to be patentable as amended.

Claims 9, 12 and 13, dependent on an amended claim, are determined to be patentable.

New claims 33–56 are added and determined to be patentable.

3. A method according to [claim 1 or 2] *any one of claims 1, 2, and 33 to 46*, wherein the step of applying non-excitatory electric field comprises applying an [alternated] *alternating* current electric field.

4. A method according to [claim 1 or 2] *any one of claims 33 to 46*, wherein the step of applying non-excitatory electric field comprises applying an electric field that has a [temporal envelope selected from the group consisting of exponential temporal envelope, sinusoidal temporal envelope,] square temporal envelope[, triangular temporal envelope, ramped temporal envelope, sawtooth temporal envelope and biphasic temporal envelope] *shorter than a heartbeat*.

5. A method according to [claim 1 or 2] *any one of claims 33 to 46*, wherein the variation in cardiac muscle contraction is an increase of the force of contraction of said heart, heart chamber or a portion thereof.

6. A method according to [claim 1 or 2] *any one of claims 33 to 46*, wherein the variation in cardiac muscle contraction is followed by an increase of the stroke volume of a chamber of the heart.

7. A method according to [claim 1 or 2] *any one of claims 33 to 46*, wherein the variation in cardiac muscle contraction is followed by an increase of the output flow of a chamber of the heart.

8. A method according to [claim 1 or 2] *any one of claims 33 to 46*, wherein the variation in cardiac muscle contraction is followed by a change in pressure.

10. A method according to [claim 1 or 2] *any one of claims 33 to 46*, wherein the variation in cardiac muscle contraction is followed by a change of the heart rate.

11. A method according to [claim 1 or 2] *any one of claims 33 to 46*, comprising sensing the activation of a portion of the heart at a suitable location, and thereafter calculating or estimating therefrom the activation time of the portion of the heart the activity of which it is desired to modify.

14. A method according to [claim 1 or 2] *any one of claims 33 to 46*, wherein the activation of the Right Ventriculum is obtained by pacing, and wherein the application of the non-excitatory electric field is synchronized with the pacing signal and is effected with a timing relative to the pacing signal.

15. A method according to [claim 1 or 2] *any one of claims 1, 2, and 33 to 46*, wherein a defibrillating signal is provided to the heart, and wherein the application of the non-excitatory electric field is synchronized with said defibrillating signal.

16. A method according to [claim 1 or 2] *any one of claims 33 to 46*, wherein the electric field is applied using electrodes selected from unipolar electrodes or bipolar electrodes.

17. A method according to[, claim 1 or 2] *any one of claims 33 to 46*, wherein the application of the non-excitatory field is repeated during a plurality of heart beats, and wherein said repeated application is effected by skipping the application of the field to some of the beats in a train of consecutive heart beats.

18. A method according to [claim 1 or 2] *any one of claims 33 to 46*, wherein the variation in cardiac muscle contraction comprises selectively and reversibly increasing [or reducing] the contractility of the Right Ventriculum of the heart relative to [another portion or to] the left ventricle.

19. A method according to [claim 1 or 2] *any one of claims 1, 2, and 33 to 46*, further comprising determining a desired range of values for at least one parameter of cardiac activity and controlling at least a local force of contraction of the heart to maintain said parameter within the desired range.

20. A method according to [claim 1 or 2] *any one of claims 1, 2, and 33 to 46*, wherein the application of the non-excitatory field is repeated during a plurality of heart beats, and wherein said repeated application is effected by reducing the frequency at which the beats are skipped is gradually reduced.

21. A method according to [claim 1 or 2] *any one of claims 33 to 46*, wherein the application of the non-excitatory field is repeated, *for therapeutic purposes*, during a plurality of heart beats, and wherein said repeated application is effected by changing between beats the size of the portion of the heart to which the field is applied.

24. A method according to [any of claims] *claim* 22 [to 23], wherein the electric field is applied at the RV Septum.

*33. A method of modifying the activity of the heart, or of a portion thereof, comprising applying to the Right Ventriculum of said heart a non-excitatory electric field of a magnitude, shape, duty cycle, phase, frequency and duration suitable to obtain a variation in the force of a cardiac muscle contraction, wherein said field is applied only at a time at which it is unable to generate a propagating action potential.*

*34. A method of modifying the activity of the heart, or of a portion thereof, comprising applying to the Right Ventriculum of said heart a non-excitatory electric field of a magni-* tude, shape, duty cycle, phase, frequency and duration suitable to obtain a variation in a cardiac muscle contraction, wherein said field is applied at a time at which it is unable to generate, cause or prevent a propagating action potential.

35. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, said field being capable of said effect on a sinus rhythm heart beat, wherein said field is applied at a time at which it is unable to generate a propagating action potential.

36. A method of modifying the activity of the heart, or of a portion thereof, comprising:
   determining a desired polarity of variation in heart muscle contraction; and
   applying to the Right Ventriculum of said heart a non-excitatory electric field of a magnitude, shape, duty cycle, phase, frequency and duration suitable to obtain a desired variation in a cardiac muscle contraction, wherein said field is applied at a time at which it is unable to generate a propagating action potential.

37. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, wherein said field is applied at a time at which it is unable to generate a propagating action potential and wherein said field affects the contraction of a portion of muscle to which it is applied.

38. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, wherein said field is applied at a time at which it is unable to generate a propagating action potential and wherein said field does not, by itself, affect an order of activation of the heart chambers.

39. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, wherein said field is applied at a time at which it is unable to generate a propagating action potential and wherein said field does not, by itself, affect a timing of activation of the heart chambers.

40. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, wherein said field is applied at a time at which it is unable to generate a propagating action potential and wherein said field does not, by itself, affect a conduction of a pacing signal from an SA node.

41. A method of modifying the activity of the heart, or of a portion thereof, comprising applying to the Right Ventriculum of said heart a non-excitatory electric field of a magnitude, shape, duty cycle, phase, frequency and duration suitable to obtain a variation in an existing cardiac muscle contraction, wherein said field is applied at a time at which it is unable to generate a propagating action potential.

42. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, wherein said field is applied at a time at which it is unable to generate a propagating action potential and wherein said field is applied and is effective also early in a refractory period.

43. A method of modifying the activity of the heart, or of a portion thereof, comprising:
   determining a desired variation in a cardiac muscle contraction;
   providing field parameters suitable for obtaining said desired variation in cardiac muscle contraction; and
   applying to the Right Ventriculum of said heart a non-excitatory electric field having said parameters, wherein said field is applied at a time at which it is unable to generate a propagating action potential.

44. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, wherein said field is applied at a time at which it is unable to generate a propagating action potential and wherein said field is applied to at least 1000 cardiac cycles during a period of 50,000 cycles.

45. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a later occurring cardiac muscle contraction, wherein said field is applied at a time at which it is unable to generate a propagating action potential.

46. A method of modifying the activity of the heart, or of a portion thereof, comprising applying to the Right Ventriculum of said heart a non-excitatory electric field of a magnitude, shape, duty cycle, phase, frequency and duration suitable to obtain a variation in a cardiac muscle contraction, by directly affecting said contraction, wherein said field is applied at a time at which it is unable to generate a propagating action potential.

47. A method according to any one of claims 1, 2, and 33 to 46, wherein the step of applying non-excitatory electric field comprises applying an electric field that has an exponential temporal envelope.

48. A method according to any one of claims 1, 2, and 33 to 46, wherein the step of applying non-excitatory electric field comprises applying an electric field that has a sinusoidal temporal envelope.

49. A method according to any one of claims 1, 2, and 33 to 46, wherein the step of applying non-excitatory electric field comprises applying an electric field that has a triangular temporal envelope.

50. A method according to any one of claims 1, 2, and 33 to 46, wherein the step of applying non-excitatory electric field comprises applying an electric field that has a ramped temporal envelope.

51. A method according to any one of claims 1, 2, and 33 to 46, wherein the step of applying non-excitatory electric field comprises applying an electric field that has a sawtooth temporal envelope.

52. A method according to any one of claims 1, 2, and 33 to 46, wherein the step of applying non-excitatory electric field comprises applying an electric field that has a biphasic temporal envelope.

53. A method according to any one of claims 1, 2, and 33 to 46, wherein the variation in cardiac muscle contraction comprises selectively and reversibly reducing the contractility of the Right Ventriculum of the heart relative to the left ventricle.

54. A method according to any one of claims 1, 2, and 33 to 46, wherein the variation in cardiac muscle contraction comprises selectively and reversibly reducing the contractility of the Right Ventriculum of the heart relative to another portion.

55. A method of reducing the output of the Right Ventriculum of a heart, comprising applying to a portion of said Right Ventriculum a non-excitatory electric field of a magnitude, shape, duty cycle, phase, frequency and duration suitable to obtain a desired change, wherein said field is applied at a time at which it is unable to generate a propagating action potential, and wherein reducing the output of the chamber is obtained by reducing the reactivity of said portion to an activation signal.

56. A method according to any one of claims 1, 2, and 33 to 46, wherein said field is applied at a location, within 70 ms of a local activation at the location.

* * * * *